(12) United States Patent
Marion et al.

(10) Patent No.: US 10,821,159 B2
(45) Date of Patent: Nov. 3, 2020

(54) TARGET FOR DIABETES TREATMENT AND PREVENTION

(71) Applicants: UNIVERSITE DE STRASBOURG, Strasbourg (FR); INSTITUT NATIONAL DE LA SANTE ET DE LA RECHERCHE MEDICALE, Paris (FR); VAXINE PTY LTD, Bedford Park (AU)

(72) Inventors: Vincent Marion, Schiltigheim (FR); Nikolai Petrovsky, Adelaide (AU)

(73) Assignees: UNIVERSITE DE STRASBOURG, Strasbourg (FR); INSTITUT NATIONAL DE LA SANTE ET DE LA RECHERCHE MEDICALE, Paris (FR); VAXINE PTY LTD, Bedford Park (AU)

( * ) Notice: Subject to any disclaimer, the term of this patent is extended or adjusted under 35 U.S.C. 154(b) by 0 days.

(21) Appl. No.: 15/114,080

(22) PCT Filed: Jan. 29, 2015

(86) PCT No.: PCT/EP2015/051856
§ 371 (c)(1),
(2) Date: Jul. 26, 2016

(87) PCT Pub. No.: WO2015/114062
PCT Pub. Date: Aug. 6, 2015

(65) Prior Publication Data
US 2017/0000857 A1    Jan. 5, 2017

(30) Foreign Application Priority Data

Jan. 29, 2014    (EP) .................................. 14153017

(51) Int. Cl.
| A61K 38/45 | (2006.01) |
| A61K 38/03 | (2006.01) |
| A61K 38/17 | (2006.01) |
| G01N 33/50 | (2006.01) |

(52) U.S. Cl.
CPC .............. *A61K 38/45* (2013.01); *A61K 38/03* (2013.01); *A61K 38/1709* (2013.01); *G01N 33/5064* (2013.01); *G01N 2333/91205* (2013.01); *G01N 2500/04* (2013.01)

(58) Field of Classification Search
CPC ..................................................... A61K 38/45
See application file for complete search history.

(56) References Cited

U.S. PATENT DOCUMENTS

| 4,946,778 | A | 8/1990 | Ladner et al. | |
| 6,225,120 | B1* | 5/2001 | Ruvkun | A61K 49/0004 435/320.1 |
| 7,727,958 | B2* | 6/2010 | Li | A61K 38/08 424/1.73 |
| 8,686,115 | B2* | 4/2014 | Cho | G01N 33/582 530/350 |
| 2002/0162127 | A1* | 10/2002 | Gu | C07K 14/4748 800/8 |
| 2005/0214757 | A1* | 9/2005 | Wilson | C07K 14/47 435/6.13 |
| 2005/0250719 | A1* | 11/2005 | Menne | A61K 31/235 514/44 R |
| 2006/0067926 | A1* | 3/2006 | Boylan | C12N 9/1205 424/94.5 |
| 2008/0009025 | A1* | 1/2008 | Alessi | C12N 9/1205 435/15 |
| 2009/0081786 | A1* | 3/2009 | Kheifets | C07K 14/4721 435/375 |
| 2009/0191194 | A1 | 7/2009 | Menne et al. | |
| 2010/0216701 | A1* | 8/2010 | Shafrir | C07K 14/81 514/6.9 |
| 2012/0225447 | A1* | 9/2012 | Cho | G01N 33/582 435/29 |
| 2012/0232037 | A1* | 9/2012 | Farese | A61K 31/4164 514/94 |
| 2013/0331374 | A1* | 12/2013 | Singh | C07D 471/04 514/210.21 |

(Continued)

FOREIGN PATENT DOCUMENTS

| WO | WO-98/08856 A2 | 3/1998 |
| WO | WO 03/034072 | 4/2003 |
| WO | WO 2004/028516 | 4/2004 |

(Continued)

OTHER PUBLICATIONS

Medkova et al., 1999, Interplay of C1 and C2 Domains of Protein Kinase C-alpha in Its Membrane Binding and Activation, the Journal of Biological Chemistry, 274(28): 19852-19861.*
Verdine et al., 2012, Stapled Peptide for Intracellular Drug Targets, Methods in Enzymology, 503: 3-33.*
Collin,G.B. et al. "Mutations in ALMS1 cause obesity, type 2 diabetes and neurosensory degeneration in Alström syndrome" *Nature Genetics*, May 1, 2002, pp. 74-78, vol. 31, No. 1.

(Continued)

*Primary Examiner* — Amber D Steele
(74) *Attorney, Agent, or Firm* — Saliwanchik, Lloyd & Eisenschenk

(57) ABSTRACT

The present invention relates to the identification of ALMS1 as the missing player involved in the regulation of the insulin-mediated glucose uptake through GLUT4 sorting vesicles, and to the down-regulation of ALMS1 by αPKC. Accordingly, the present invention relates to a molecule capable of preventing the binding of αPKC on ALMS1 for use for treating or preventing diabetes, in particular type 2 diabetes. In addition, the present invention relates to a method for identifying molecule capable of preventing the binding of αPKC on ALMS1.

8 Claims, 13 Drawing Sheets
Specification includes a Sequence Listing.

(56) References Cited

U.S. PATENT DOCUMENTS

2013/0336952 A1* 12/2013 Braiman-Wiksman ............ A61K 38/08
424/94.5

FOREIGN PATENT DOCUMENTS

| WO | WO 2005/079300 | 9/2005 |
|---|---|---|
| WO | WO 2007/146981 | 12/2007 |
| WO | WO-2010/011313 A2 | 1/2010 |
| WO | WO-2010/033617 A2 | 3/2010 |
| WO | WO-2012/117245 A1 | 9/2012 |
| WO | WO-2012/174489 A2 | 12/2012 |

OTHER PUBLICATIONS

Written Opinion in International Application No. PCT/EP2015/051856, dated May 29, 2015, pp. 1-10.

Colas, et al., "Genetic selection of peptide aptamers that recognize and inhibit cyclin-dependent kinase 2," Nature, Apr. 11, 1996, pp. 548-550, vol. 380.

Cole, et al., "The EBV-hybridoma technique and its application to human lung cancer," Monoclonal Antibodies and Cancer Therapy, Jan. 1985, pp. 77-96, vol. 27.

International Preliminary Report on Patentability in International Application No. PCT/EP2015/051856 dated Aug. 2, 2016 (11 pages).

International Search Report and Written Opinion in International Application No. PCT/EP/051856 dated May 29, 2015 (15 pages).

Jayasena, et al., "Aptamers: An Emerging Class of Molecules That Rival Antibodies in Diagnostics," Clinical Chemistry, 1999, pp. 1628-1650, vol. 45, No. 9.

Kohler, et al., "Continuous cultures of fused cells secreting antibody of predefined specificity," Nature, Aug. 7, 1975, pp. 495-497, vol. 256.

Kozbor, et al., "The production of monoclonal antibodies from human lymphocytes." Immunology Today, Mar. 1983, pp. 72-79, vol. 4, Issue 3.

Marks, et al., "By-Passing Immunization: Building High Affinity Human Antibodies by Chain Shuffling," Nature Biotechnology, Jul. 1992, pp. 779-783, vol. 10.

Matsushita, et al., "Protein transduction technology," Journal of Molecular Medicine, May 2005, pp. 324-328, vol. 83, Issue 5.

McCafferty, et al., "Phage antibodies: filamentous phage displaying antibody variable domains," Nature, Dec. 6, 1990, pp. 552-554, vol. 348.

Official Notification in EAPO Application No. 201691498 (PCT/EP2015/051856) dated Mar. 7, 2018 (with English translation) (7 pages).

Tuerk, et al., "Systematic evolution of ligands by exponential enrichment: RNA ligands to bacteriophage T4 DNA polymerase," Science, Aug. 3, 1990, pp. 505-510, vol. 249, Issue 4968.

Verdine, et al., "Chapter one—Stapled Peptides for Intracellular Drug Targets," Methods in Enzymology, 2012, pp. 3-33, vol. 503.

Vives, et al., "Cell-penetrating and cell-targeting peptides in drug delivery," Biochimic et Biophysica Acta—Reviews on Cancer, Dec. 2008, pp. 126-138, vol. 1786, Issue 2.

Claims pending in U.S. Appl. No. 16/627,389, filed Dec. 30, 2019, pp. 1-6.

* cited by examiner

FIGURE 2 (following)
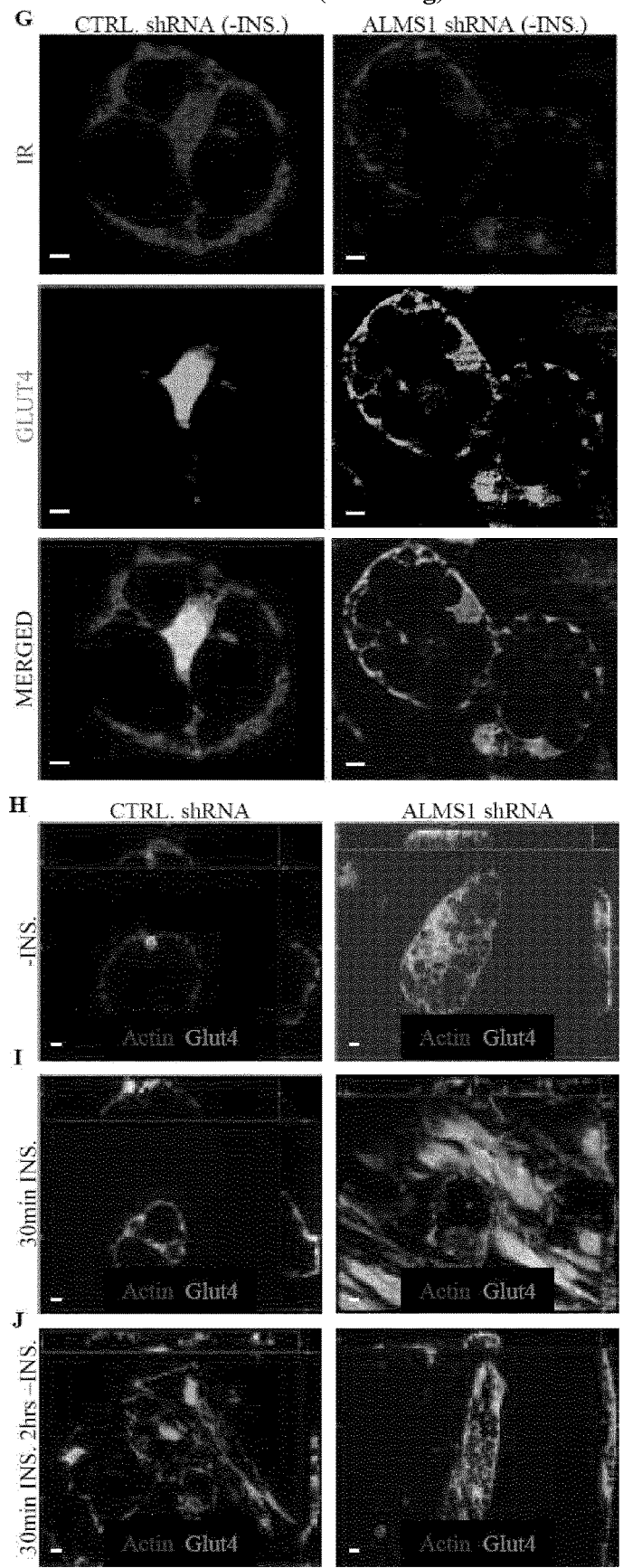

FIGURE 4
A
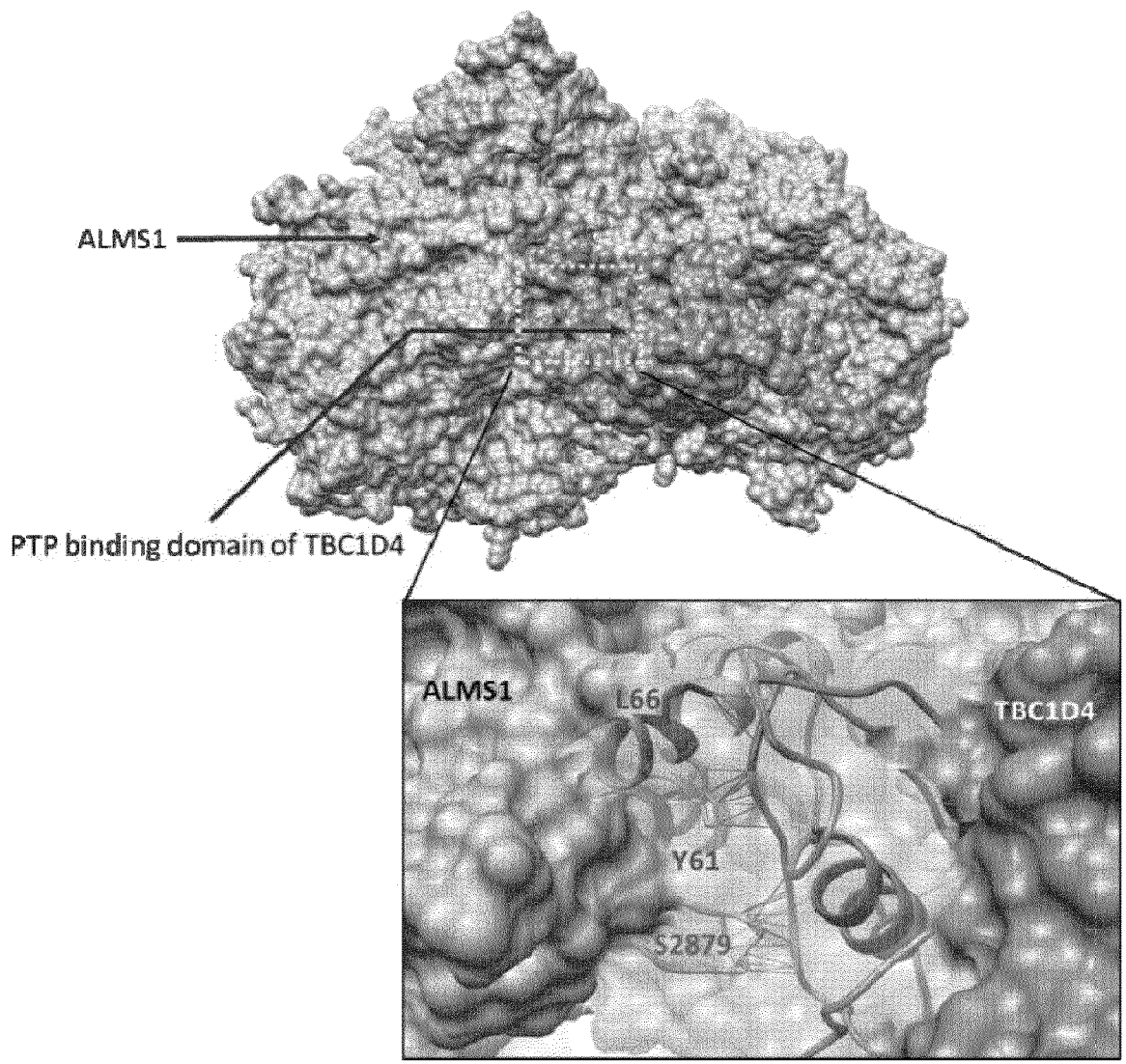
B Mature adipocyte (3D image)
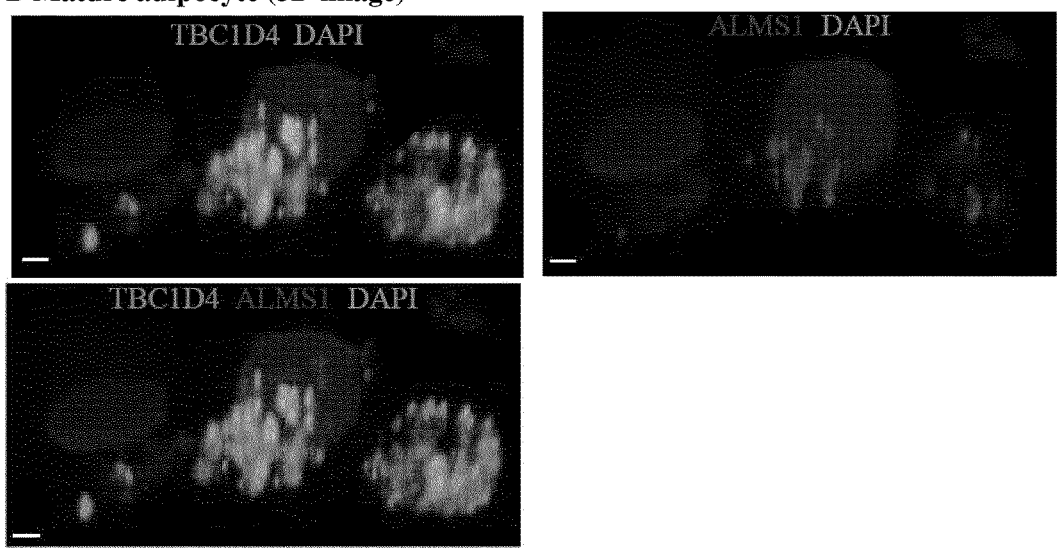

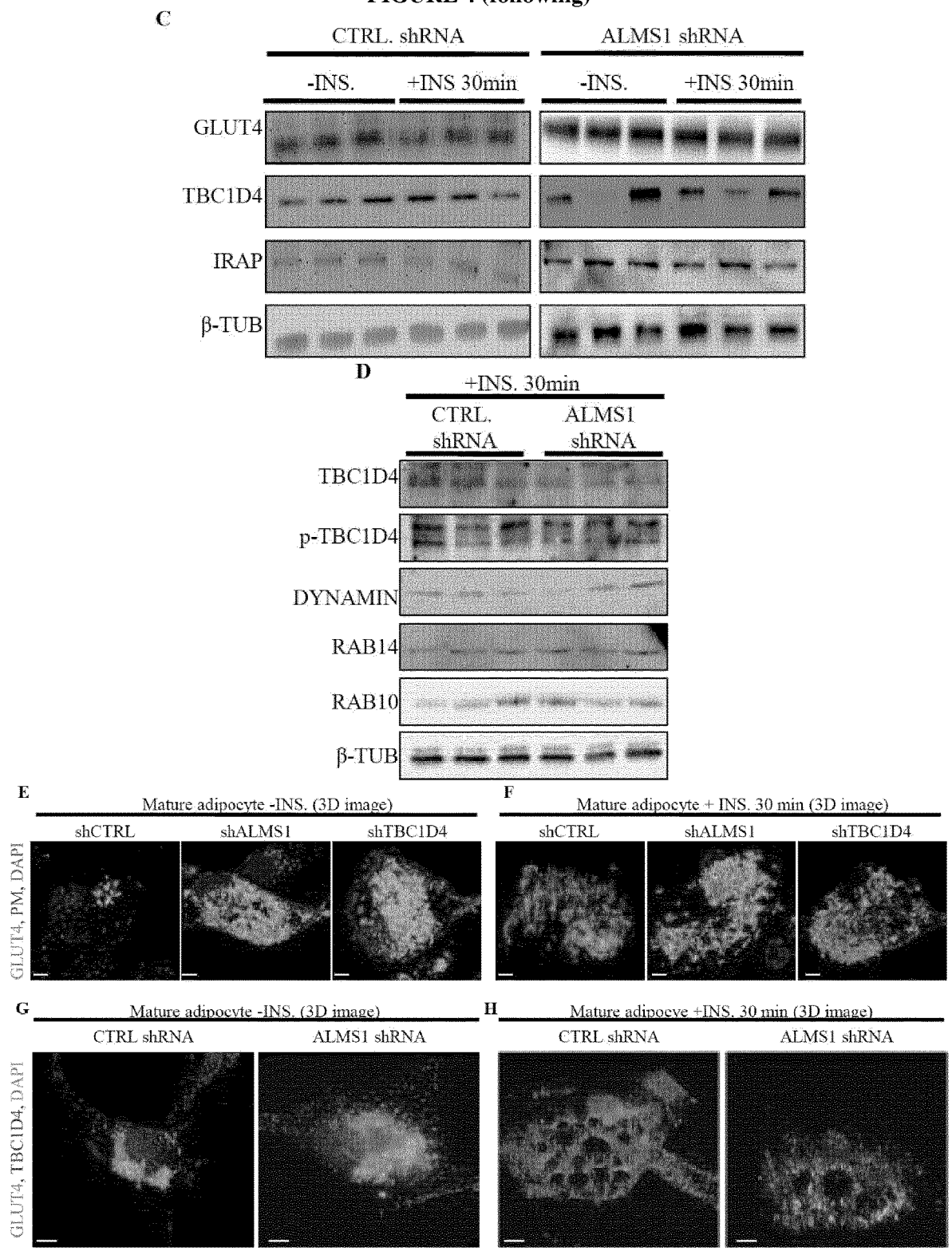

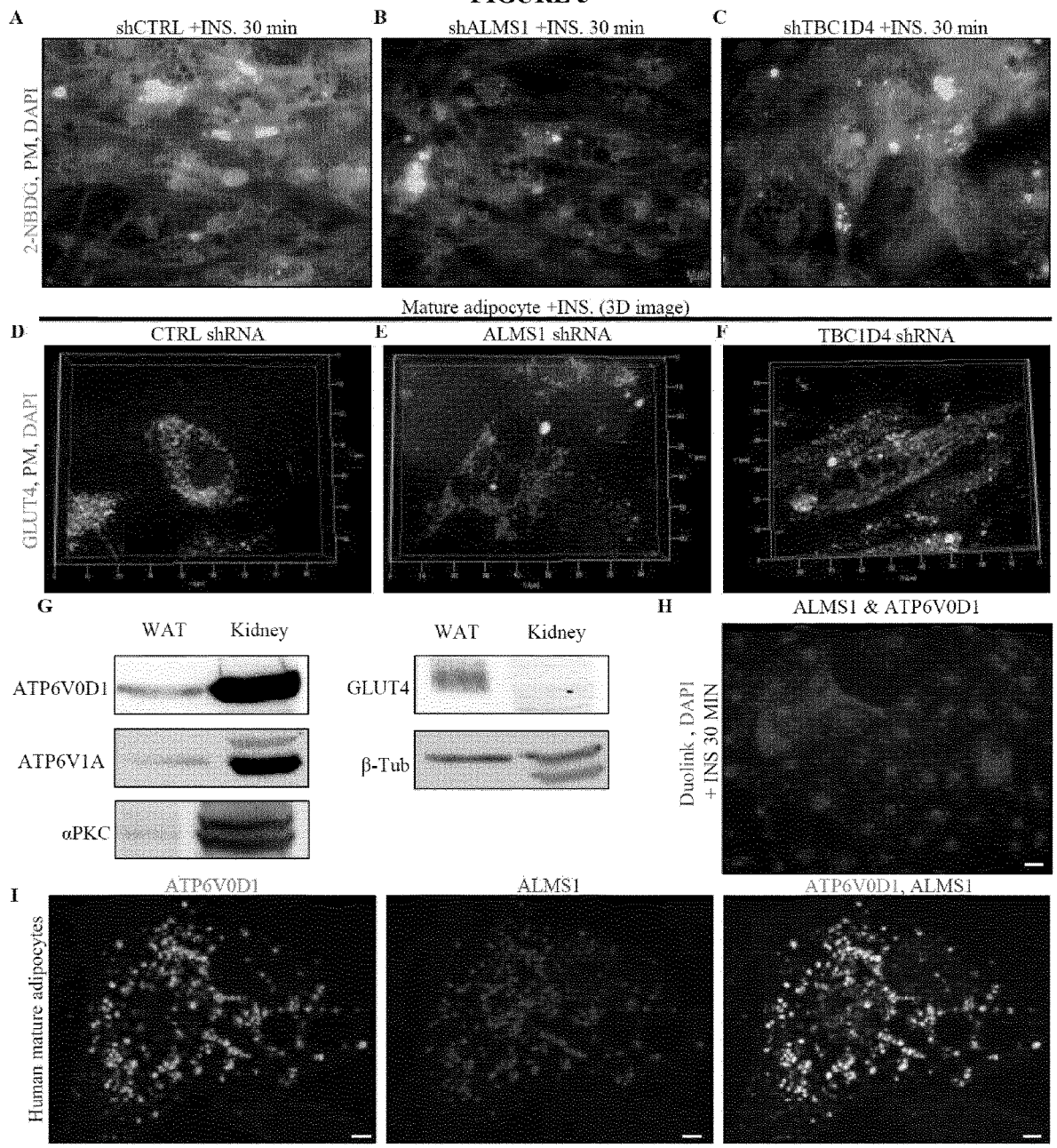

FIGURE 5 (following)
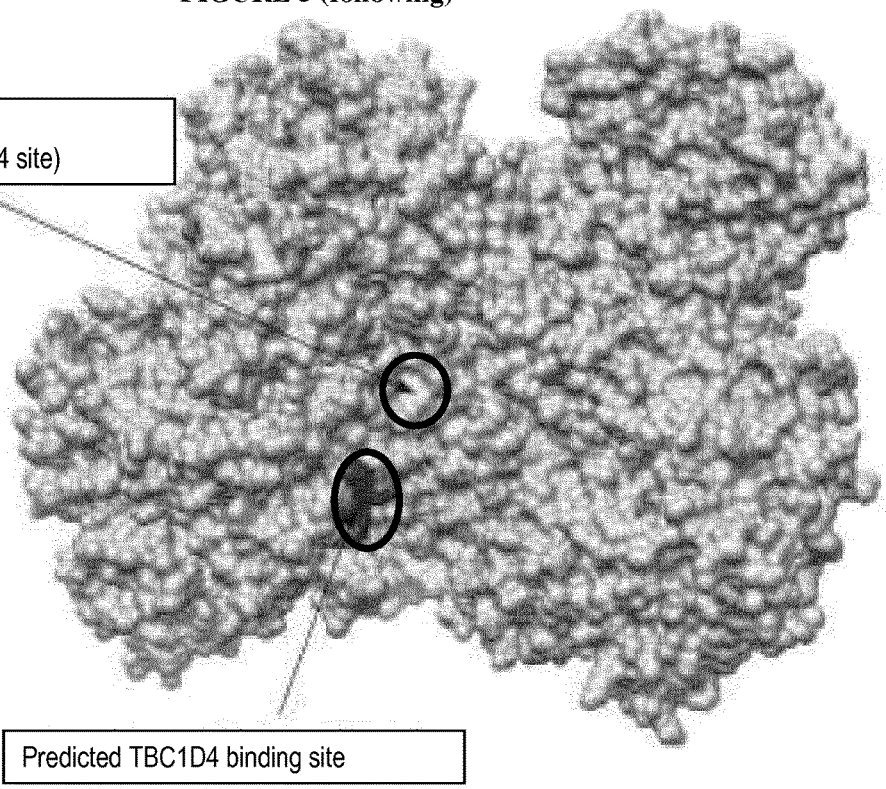

FIGURE 7
Mature adipocyte +30 min. NIG. (3D image)
A
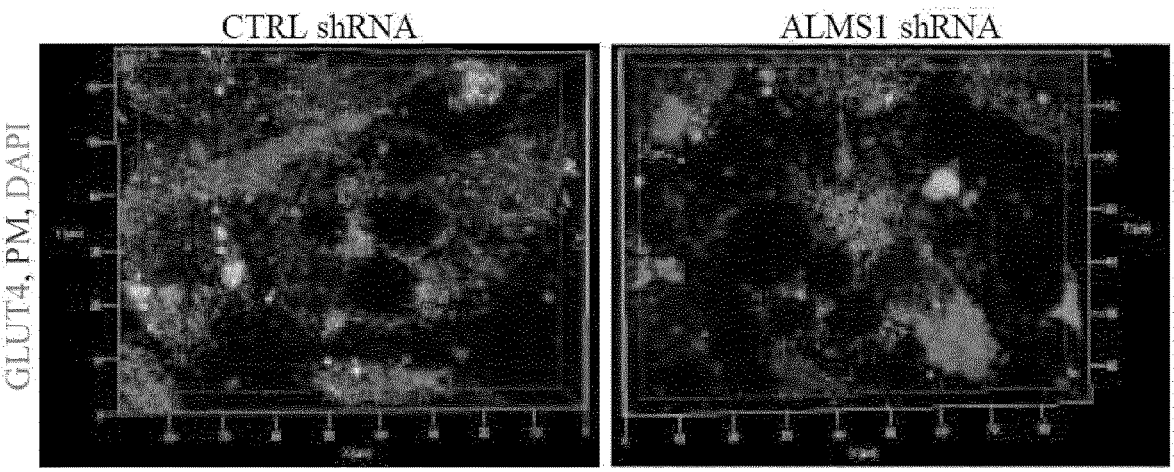
B  24 hours post-NIG
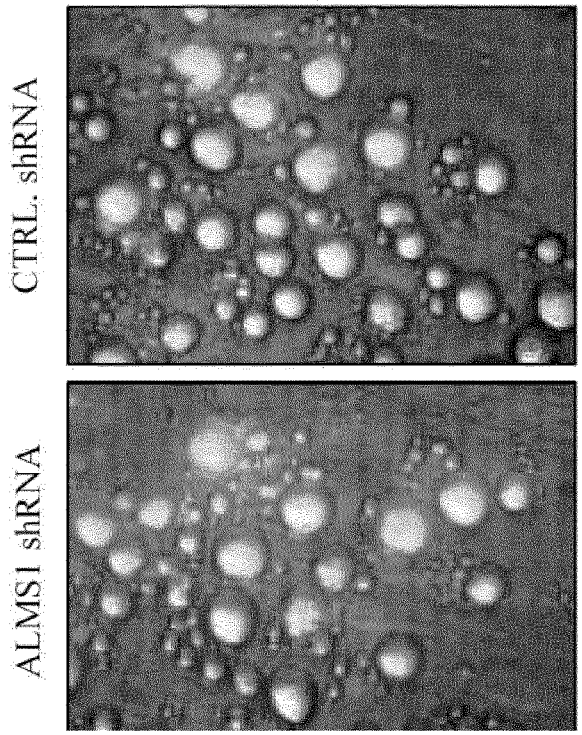

FIGURE 7 (following)
C
In absence of Insulin
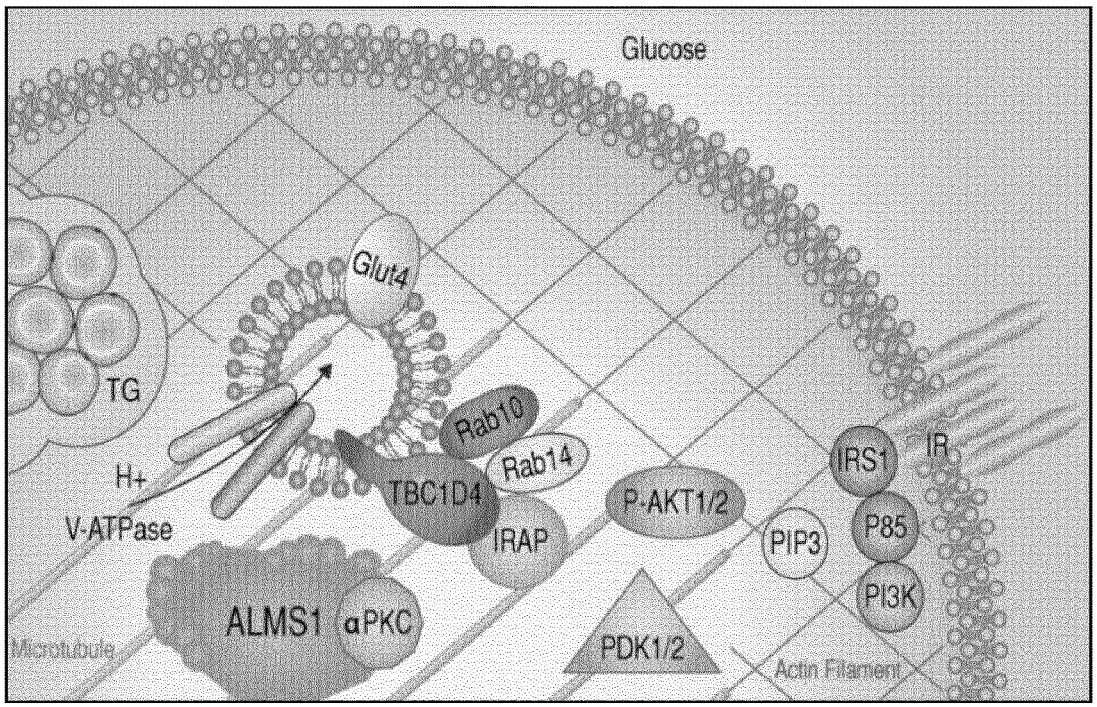
D
In presence of Insulin
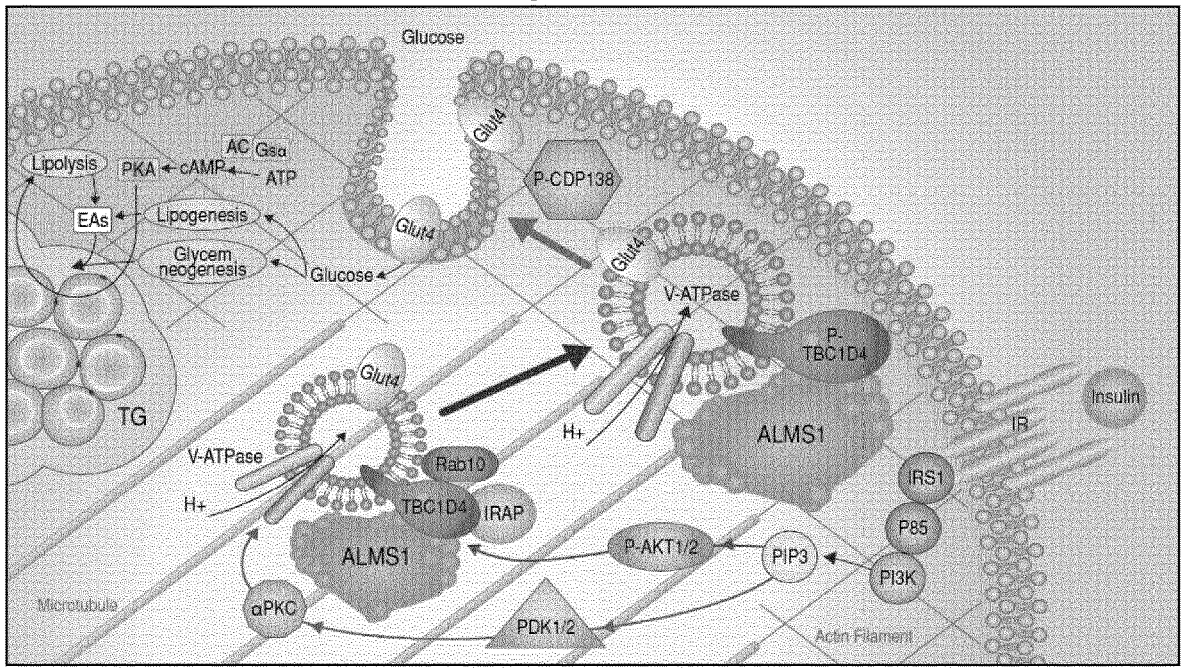

SEQUENCE LISTING

<160> NUMBER OF SEQ ID NOS: 21

<210> SEQ ID NO 1
<211> LENGTH: 4169
<212> TYPE: PRT
<213> ORGANISM: homo sapiens

<400> SEQUENCE: 1

```
Met Glu Pro Glu Asp Leu Pro Trp Pro Gly Glu Leu Glu Glu Glu Glu
1               5                   10                  15

Glu Glu Glu Glu Glu Glu Glu Glu Glu Glu Glu Glu Glu Ala Ala Ala
                20                  25                  30

Ala Ala Ala Ala Asn Val Asp Val Val Val Glu Glu Val Glu
            35                  40                  45

Glu Glu Ala Gly Arg Glu Leu Asp Ser Asp Ser His Tyr Gly Pro Gln
50                  55                  60

His Leu Glu Ser Ile Asp Asp Glu Glu Asp Glu Glu Ala Lys Ala Trp
65                  70                  75                  80

Leu Gln Ala His Pro Gly Arg Ile Leu Pro Leu Ser Pro Pro Gln
                85                  90                  95

His Arg Tyr Ser Glu Gly Glu Arg Thr Ser Leu Glu Lys Ile Val Pro
                100                 105                 110

Leu Thr Cys His Val Trp Gln Gln Ile Val Tyr Gln Gly Asn Ser Arg
                115                 120                 125

Thr Gln Ile Ser Asp Thr Asn Val Val Cys Leu Glu Thr Thr Ala Gln
                130                 135                 140

Arg Gly Ser Gly Asp Asp Gln Lys Thr Glu Ser Trp His Cys Leu Pro
145                 150                 155                 160

Gln Glu Met Asp Ser Ser Gln Thr Leu Asp Thr Ser Gln Thr Arg Phe
                165                 170                 175

Asn Val Arg Thr Glu Asp Thr Glu Val Thr Asp Phe Pro Ser Leu Glu
                180                 185                 190

Glu Gly Ile Leu Thr Gln Ser Glu Asn Gln Val Lys Glu Pro Asn Arg
                195                 200                 205

Asp Leu Phe Cys Ser Pro Leu Leu Val Ile Gln Asp Ser Phe Ala Ser
                210                 215                 220

Pro Asp Leu Pro Leu Leu Thr Cys Leu Thr Gln Asp Gln Glu Phe Ala
225                 230                 235                 240

Pro Asp Ser Leu Phe His Gln Ser Glu Leu Ser Phe Ala Pro Leu Arg
                245                 250                 255

Gly Ile Pro Asp Lys Ser Glu Asp Thr Glu Trp Ser Ser Arg Pro Ser
                260                 265                 270

Glu Val Ser Glu Ala Leu Phe Gln Ala Thr Ala Glu Val Ala Ser Asp
                275                 280                 285

Leu Ala Ser Ser Arg Phe Ser Val Ser Gln His Pro Leu Ile Gly Ser
                290                 295                 300

Thr Ala Val Gly Ser Gln Cys Pro Phe Leu Pro Ser Glu Gln Gly Asn
305                 310                 315                 320

Asn Glu Glu Thr Ile Ser Ser Val Asp Glu Leu Lys Ile Pro Lys Asp
                325                 330                 335

Cys Asp Arg Tyr Asp Asp Leu Cys Ser Tyr Met Ser Trp Lys Thr Arg
                340                 345                 350

Lys Asp Thr Gln Trp Pro Glu Asn Asn Leu Ala Asp Lys Asp Gln Val
                355                 360                 365
```

-continued

```
Ser Val Ala Thr Ser Phe Asp Ile Thr Asp Glu Asn Ile Ala Thr Lys
    370                 375                 380

Arg Ser Asp His Phe Asp Ala Arg Ser Tyr Gly Gln Tyr Trp Thr
385                 390                 395                 400

Gln Glu Asp Ser Ser Lys Gln Ala Glu Thr Tyr Leu Thr Lys Gly Leu
                405                 410                 415

Gln Gly Lys Val Glu Ser Asp Val Ile Thr Leu Asp Gly Leu Asn Glu
            420                 425                 430

Asn Ala Val Val Cys Ser Glu Arg Val Ala Glu Leu Gln Arg Lys Pro
        435                 440                 445

Thr Arg Glu Ser Glu Tyr His Ser Ser Asp Leu Arg Met Leu Arg Met
450                 455                 460

Ser Pro Asp Thr Val Pro Lys Ala Pro Lys His Leu Lys Ala Gly Asp
465                 470                 475                 480

Thr Ser Lys Gly Gly Ile Ala Lys Val Thr Gln Ser Asn Leu Lys Ser
                485                 490                 495

Gly Ile Thr Thr Thr Pro Val Asp Ser Asp Ile Gly Ser His Leu Ser
            500                 505                 510

Leu Ser Leu Glu Asp Leu Ser Gln Leu Ala Val Ser Ser Pro Leu Glu
        515                 520                 525

Thr Thr Thr Gly Gln His Thr Asp Thr Leu Asn Gln Lys Thr Leu Ala
530                 535                 540

Asp Thr His Leu Thr Glu Glu Thr Leu Lys Val Thr Ala Ile Pro Glu
545                 550                 555                 560

Pro Ala Asp Gln Lys Thr Ala Thr Pro Thr Val Leu Ser Ser Ser His
                565                 570                 575

Ser His Arg Gly Lys Pro Ser Ile Phe Tyr Gln Gln Gly Leu Pro Asp
            580                 585                 590

Ser His Leu Thr Glu Glu Ala Leu Lys Val Ser Ala Ala Pro Gly Leu
        595                 600                 605

Ala Asp Gln Thr Thr Gly Met Ser Thr Leu Thr Ser Thr Ser Tyr Ser
610                 615                 620

His Arg Glu Lys Pro Gly Thr Phe Tyr Gln Gln Glu Leu Pro Glu Ser
625                 630                 635                 640

Asn Leu Thr Glu Glu Pro Leu Glu Val Ser Ala Ala Pro Gly Pro Val
                645                 650                 655

Glu Gln Lys Thr Gly Ile Pro Thr Val Ser Ser Thr Ser His Ser His
            660                 665                 670

Val Glu Asp Leu Leu Phe Phe Tyr Arg Gln Thr Leu Pro Asp Gly His
        675                 680                 685

Leu Thr Asp Gln Ala Leu Lys Val Ser Ala Val Ser Gly Pro Ala Asp
690                 695                 700

Gln Lys Thr Gly Thr Ala Thr Val Leu Ser Thr Pro His Ser His Arg
705                 710                 715                 720

Glu Lys Pro Gly Ile Phe Tyr Gln Gln Glu Phe Ala Asp Ser His Gln
                725                 730                 735

Thr Glu Glu Thr Leu Thr Lys Val Ser Ala Thr Pro Gly Pro Ala Asp
            740                 745                 750

Gln Lys Thr Glu Ile Pro Ala Val Gln Ser Ser Ser Tyr Ser Gln Arg
        755                 760                 765

Glu Lys Pro Ser Ile Leu Tyr Pro Gln Asp Leu Ala Asp Ser His Leu
770                 775                 780

Pro Glu Glu Gly Leu Lys Val Ser Ala Val Ala Gly Pro Ala Asp Gln
```

-continued

```
                785                 790                 795                 800
Lys Thr Gly Leu Pro Thr Val Pro Ser Ser Ala Tyr Ser His Arg Glu
                    805                 810                 815
Lys Leu Leu Val Phe Tyr Gln Gln Ala Leu Leu Asp Ser His Leu Pro
                    820                 825                 830
Glu Glu Ala Leu Lys Val Ser Ala Val Ser Gly Pro Ala Asp Gly Lys
                    835                 840                 845
Thr Gly Thr Pro Ala Val Thr Ser Thr Ser Ser Ala Ser Ser Ser Leu
                    850                 855                 860
Gly Glu Lys Pro Ser Ala Phe Tyr Gln Gln Thr Leu Pro Asn Ser His
865                 870                 875                 880
Leu Thr Glu Glu Ala Leu Lys Val Ser Ile Val Pro Gly Pro Gly Asp
                    885                 890                 895
Gln Lys Thr Gly Ile Pro Ser Ala Pro Ser Ser Phe Tyr Ser His Arg
                    900                 905                 910
Glu Lys Pro Ile Ile Phe Ser Gln Gln Thr Leu Pro Asp Phe Leu Phe
                    915                 920                 925
Pro Glu Glu Ala Leu Lys Val Ser Ala Val Ser Val Leu Ala Ala Gln
                    930                 935                 940
Lys Thr Gly Thr Pro Thr Val Ser Ser Asn Ser His Ser His Ser Glu
945                 950                 955                 960
Lys Ser Ser Val Phe Tyr Gln Gln Glu Leu Pro Asp Ser Asp Leu Pro
                    965                 970                 975
Arg Glu Ser Leu Lys Met Ser Ala Ile Pro Gly Leu Thr Asp Gln Lys
                    980                 985                 990
Thr Val Pro Thr Pro Thr Val Pro Ser Gly Ser Phe Ser His Arg Glu
                    995                 1000                1005
Lys Pro Ser Ile Phe Tyr Gln Gln Glu Trp Pro Asp Ser Tyr Ala
                    1010                1015                1020
Thr Glu Lys Ala Leu Lys Val Ser Thr Gly Pro Gly Pro Ala Asp
                    1025                1030                1035
Gln Lys Thr Glu Ile Pro Ala Val Gln Ser Ser Ser Tyr Pro Gln
                    1040                1045                1050
Arg Glu Lys Pro Ser Val Leu Tyr Pro Gln Val Leu Ser Asp Ser
                    1055                1060                1065
His Leu Pro Glu Glu Ser Leu Lys Val Ser Ala Phe Pro Gly Pro
                    1070                1075                1080
Ala Asp Gln Met Thr Asp Thr Pro Ala Val Pro Ser Thr Phe Tyr
                    1085                1090                1095
Ser Gln Arg Glu Lys Pro Gly Ile Phe Tyr Gln Gln Thr Leu Pro
                    1100                1105                1110
Glu Ser His Leu Pro Lys Glu Ala Leu Lys Ile Ser Val Ala Pro
                    1115                1120                1125
Gly Leu Ala Asp Gln Lys Thr Gly Thr Pro Thr Val Thr Ser Thr
                    1130                1135                1140
Ser Tyr Ser Gln His Arg Glu Lys Pro Ser Ile Phe His Gln Gln
                    1145                1150                1155
Ala Leu Pro Gly Thr His Ile Pro Glu Glu Ala Gln Lys Val Ser
                    1160                1165                1170
Ala Val Thr Gly Pro Gly Asn Gln Lys Thr Trp Ile Pro Arg Val
                    1175                1180                1185
Leu Ser Thr Phe Tyr Ser Gln Arg Glu Lys Pro Gly Ile Phe Tyr
                    1190                1195                1200
```

```
Gln Gln Thr Leu Pro Gly Ser His Ile Pro Glu Glu Ala Gln Lys
    1205                1210                1215

Val Ser Pro Val Leu Gly Pro Ala Asp Gln Lys Thr Gly Thr Pro
    1220                1225                1230

Thr Pro Thr Ser Ala Ser Tyr Ser His Thr Glu Lys Pro Gly Ile
    1235                1240                1245

Phe Tyr Gln Gln Val Leu Pro Asp Asn His Pro Thr Glu Glu Ala
    1250                1255                1260

Leu Lys Ile Ser Val Ala Ser Glu Pro Val Asp Gln Thr Thr Gly
    1265                1270                1275

Thr Pro Ala Val Thr Ser Thr Ser Tyr Ser Gln Tyr Arg Glu Lys
    1280                1285                1290

Pro Ser Ile Phe Tyr Gln Gln Ser Leu Pro Ser Ser His Leu Thr
    1295                1300                1305

Glu Glu Ala Lys Asn Val Ser Ala Val Pro Gly Pro Ala Asp Gln
    1310                1315                1320

Lys Thr Val Ile Pro Ile Leu Pro Ser Thr Phe Tyr Ser His Thr
    1325                1330                1335

Glu Lys Pro Gly Val Phe Tyr Gln Gln Val Leu Pro His Ser His
    1340                1345                1350

Pro Thr Glu Glu Ala Leu Lys Ile Ser Val Ala Ser Glu Pro Val
    1355                1360                1365

Asp Gln Thr Thr Gly Thr Pro Thr Val Thr Ser Thr Ser Tyr Ser
    1370                1375                1380

Gln His Thr Glu Lys Pro Ser Ile Phe Tyr Gln Gln Ser Leu Pro
    1385                1390                1395

Gly Ser His Leu Thr Glu Glu Ala Lys Asn Val Ser Ala Val Pro
    1400                1405                1410

Gly Pro Gly Asp Arg Lys Thr Gly Ile Pro Thr Leu Pro Ser Thr
    1415                1420                1425

Phe Tyr Ser His Thr Glu Lys Pro Gly Ser Phe Tyr Gln Gln Val
    1430                1435                1440

Leu Pro His Ser His Leu Pro Glu Glu Ala Leu Glu Val Ser Val
    1445                1450                1455

Ala Pro Gly Pro Val Asp Gln Thr Ile Gly Thr Pro Thr Val Thr
    1460                1465                1470

Ser Pro Ser Ser Ser Phe Gly Glu Lys Pro Ile Val Ile Tyr Lys
    1475                1480                1485

Gln Ala Phe Pro Glu Gly His Leu Pro Glu Glu Ser Leu Lys Val
    1490                1495                1500

Ser Val Ala Pro Gly Pro Val Gly Gln Thr Thr Gly Ala Pro Thr
    1505                1510                1515

Ile Thr Ser Pro Ser Tyr Ser Gln His Arg Ala Lys Ser Gly Ser
    1520                1525                1530

Phe Tyr Gln Leu Ala Leu Leu Gly Ser Gln Ile Pro Glu Glu Ala
    1535                1540                1545

Leu Arg Val Ser Ser Ala Pro Gly Pro Ala Asp Gln Thr Thr Gly
    1550                1555                1560

Ile Pro Thr Ile Thr Ser Thr Ser Tyr Ser Phe Gly Glu Lys Pro
    1565                1570                1575

Ile Val Asn Tyr Lys Gln Ala Phe Pro Asp Gly His Leu Pro Glu
    1580                1585                1590
```

```
Glu Ala Leu Lys Val Ser Ile Val Ser Gly Pro Thr Glu Lys Lys
1595                1600                1605

Thr Asp Ile Pro Ala Gly Pro Leu Gly Ser Ser Ala Leu Gly Glu
1610                1615                1620

Lys Pro Ile Thr Phe Tyr Arg Gln Ala Leu Leu Asp Ser Pro Leu
1625                1630                1635

Asn Lys Glu Val Val Lys Val Ser Ala Ala Pro Gly Pro Ala Asp
1640                1645                1650

Gln Lys Thr Glu Thr Leu Pro Val His Ser Thr Ser Tyr Ser Asn
1655                1660                1665

Arg Gly Lys Pro Val Ile Phe Tyr Gln Gln Thr Leu Ser Asp Ser
1670                1675                1680

His Leu Pro Glu Glu Ala Leu Lys Val Pro Pro Val Pro Gly Pro
1685                1690                1695

Asp Ala Gln Lys Thr Glu Thr Pro Ser Val Ser Ser Ser Leu Tyr
1700                1705                1710

Ser Tyr Arg Glu Lys Pro Ile Val Phe Tyr Gln Gln Ala Leu Pro
1715                1720                1725

Asp Ser Glu Leu Thr Gln Glu Ala Leu Lys Val Ser Ala Val Pro
1730                1735                1740

Gln Pro Ala Asp Gln Lys Thr Gly Leu Ser Thr Val Thr Ser Ser
1745                1750                1755

Phe Tyr Ser His Thr Glu Lys Pro Asn Ile Ser Tyr Gln Gln Glu
1760                1765                1770

Leu Pro Asp Ser His Leu Thr Glu Glu Ala Leu Lys Val Ser Asn
1775                1780                1785

Val Pro Gly Pro Ala Asp Gln Lys Thr Gly Val Ser Thr Val Thr
1790                1795                1800

Ser Thr Ser Tyr Ser His Arg Glu Lys Pro Ile Val Ser Tyr Gln
1805                1810                1815

Arg Glu Leu Pro His Phe Thr Glu Ala Gly Leu Lys Ile Leu Arg
1820                1825                1830

Val Pro Gly Pro Ala Asp Gln Lys Thr Gly Ile Asn Ile Leu Pro
1835                1840                1845

Ser Asn Ser Tyr Pro Gln Arg Glu His Ser Val Ile Ser Tyr Glu
1850                1855                1860

Gln Glu Leu Pro Asp Leu Thr Glu Val Thr Leu Lys Ala Ile Gly
1865                1870                1875

Val Pro Gly Pro Ala Asp Gln Lys Thr Gly Ile Gln Ile Ala Ser
1880                1885                1890

Ser Ser Ser Tyr Ser Asn Arg Glu Lys Ala Ser Ile Phe His Gln
1895                1900                1905

Gln Glu Leu Pro Asp Val Thr Glu Ala Leu Asn Val Phe Val
1910                1915                1920

Val Pro Gly Gln Gly Asp Arg Lys Thr Glu Ile Pro Thr Val Pro
1925                1930                1935

Leu Ser Tyr Tyr Ser Arg Arg Glu Lys Pro Ser Val Ile Ser Gln
1940                1945                1950

Gln Glu Leu Pro Asp Ser His Leu Thr Glu Glu Ala Leu Lys Val
1955                1960                1965

Ser Pro Val Ser Ile Pro Ala Glu Gln Lys Thr Gly Ile Pro Ile
1970                1975                1980

Gly Leu Ser Ser Ser Tyr Ser His Ser His Lys Glu Lys Leu Lys
```

-continued

```
            1985                1990                1995
Ile Ser Thr Val His Ile Pro Asp Asp Gln Lys Thr Glu Phe Pro
    2000                2005                2010

Ala Ala Thr Leu Ser Ser Tyr Ser Gln Ile Glu Lys Pro Lys Ile
    2015                2020                2025

Ser Thr Val Ile Gly Pro Asn Asp Gln Lys Thr Pro Ser Gln Thr
    2030                2035                2040

Ala Phe His Ser Ser Tyr Ser Gln Thr Val Lys Pro Asn Ile Leu
    2045                2050                2055

Phe Gln Gln Gln Leu Pro Asp Arg Asp Gln Ser Lys Gly Ile Leu
    2060                2065                2070

Lys Ile Ser Ala Val Pro Glu Leu Thr Asp Val Asn Thr Gly Lys
    2075                2080                2085

Pro Val Ser Leu Ser Ser Ser Tyr Phe His Arg Glu Lys Ser Asn
    2090                2095                2100

Ile Phe Ser Pro Gln Glu Leu Pro Gly Ser His Val Thr Glu Asp
    2105                2110                2115

Val Leu Lys Val Ser Thr Ile Pro Gly Pro Ala Gly Gln Lys Thr
    2120                2125                2130

Val Leu Pro Thr Ala Leu Pro Ser Ser Phe Ser His Arg Glu Lys
    2135                2140                2145

Pro Asp Ile Phe Tyr Gln Lys Asp Leu Pro Asp Arg His Leu Thr
    2150                2155                2160

Glu Asp Ala Leu Lys Ile Ser Ser Ala Leu Gly Gln Ala Asp Gln
    2165                2170                2175

Ile Thr Gly Leu Gln Thr Val Pro Ser Gly Thr Tyr Ser His Gly
    2180                2185                2190

Glu Asn His Lys Leu Val Ser Glu His Val Gln Arg Leu Ile Asp
    2195                2200                2205

Asn Leu Asn Ser Ser Asp Ser Ser Val Ser Ser Asn Asn Val Leu
    2210                2215                2220

Leu Asn Ser Gln Ala Asp Asp Arg Val Val Ile Asn Lys Pro Glu
    2225                2230                2235

Ser Ala Gly Phe Arg Asp Val Gly Ser Glu Glu Ile Gln Asp Ala
    2240                2245                2250

Glu Asn Ser Ala Lys Thr Leu Lys Glu Ile Arg Thr Leu Leu Met
    2255                2260                2265

Glu Ala Glu Asn Met Ala Leu Lys Arg Cys Asn Phe Pro Ala Pro
    2270                2275                2280

Leu Ala Arg Phe Arg Asp Ile Ser Asp Ile Ser Phe Ile Gln Ser
    2285                2290                2295

Lys Lys Val Val Cys Phe Lys Glu Pro Ser Ser Thr Gly Val Ser
    2300                2305                2310

Asn Gly Asp Leu Leu His Arg Gln Pro Phe Thr Glu Glu Ser Pro
    2315                2320                2325

Ser Ser Arg Cys Ile Gln Lys Asp Ile Gly Thr Gln Thr Asn Leu
    2330                2335                2340

Lys Cys Arg Arg Gly Ile Glu Asn Trp Glu Phe Ile Ser Ser Thr
    2345                2350                2355

Thr Val Arg Ser Pro Leu Gln Glu Ala Glu Ser Lys Val Ser Met
    2360                2365                2370

Ala Leu Glu Glu Thr Leu Arg Gln Tyr Gln Ala Ala Lys Ser Val
    2375                2380                2385
```

```
Met Arg Ser Glu Pro Glu Gly Cys Ser Gly Thr Ile Gly Asn Lys
2390                2395                2400

Ile Ile Ile Pro Met Met Thr Val Ile Lys Ser Asp Ser Ser Ser
2405                2410                2415

Asp Ala Ser Asp Gly Asn Gly Ser Cys Ser Trp Asp Ser Asn Leu
2420                2425                2430

Pro Glu Ser Leu Glu Ser Val Ser Asp Val Leu Leu Asn Phe Phe
2435                2440                2445

Pro Tyr Val Ser Pro Lys Thr Ser Ile Thr Asp Ser Arg Glu Glu
2450                2455                2460

Glu Gly Val Ser Glu Ser Gly Asp Gly Gly Ser Ser Val Asp
2465                2470                2475

Ser Leu Ala Ala His Val Lys Asn Leu Leu Gln Cys Glu Ser Ser
2480                2485                2490

Leu Asn His Ala Lys Glu Ile Leu Arg Asn Ala Glu Glu Glu Glu
2495                2500                2505

Ser Arg Val Arg Ala His Ala Trp Asn Met Lys Phe Asn Leu Ala
2510                2515                2520

His Asp Cys Gly Tyr Ser Ile Ser Glu Leu Asn Glu Asp Asp Arg
2525                2530                2535

Arg Lys Val Glu Glu Ile Lys Ala Glu Leu Phe Gly His Gly Arg
2540                2545                2550

Thr Thr Asp Leu Ser Lys Gly Leu Gln Ser Pro Arg Gly Met Gly
2555                2560                2565

Cys Lys Pro Glu Ala Val Cys Ser His Ile Ile Ile Glu Ser His
2570                2575                2580

Glu Lys Gly Cys Phe Arg Thr Leu Thr Ser Glu His Pro Gln Leu
2585                2590                2595

Asp Arg His Pro Cys Ala Phe Arg Ser Ala Gly Pro Ser Glu Met
2600                2605                2610

Thr Arg Gly Arg Gln Asn Pro Ser Ser Cys Arg Ala Lys His Val
2615                2620                2625

Asn Leu Ser Ala Ser Leu Asp Gln Asn Asn Ser His Phe Lys Val
2630                2635                2640

Trp Asn Ser Leu Gln Leu Lys Ser His Ser Pro Phe Gln Asn Phe
2645                2650                2655

Ile Pro Asp Glu Phe Lys Ile Ser Lys Gly Leu Arg Met Pro Phe
2660                2665                2670

Asp Glu Lys Met Asp Pro Trp Leu Ser Glu Leu Val Glu Pro Ala
2675                2680                2685

Phe Val Pro Pro Lys Glu Val Asp Phe His Ser Ser Ser Gln Met
2690                2695                2700

Pro Ser Pro Glu Pro Met Lys Lys Phe Thr Thr Ser Ile Thr Phe
2705                2710                2715

Ser Ser His Arg His Ser Lys Cys Ile Ser Asn Ser Ser Val Val
2720                2725                2730

Lys Val Gly Val Thr Glu Gly Ser Gln Cys Thr Gly Ala Ser Val
2735                2740                2745

Gly Val Phe Asn Ser His Phe Thr Glu Glu Gln Asn Pro Pro Arg
2750                2755                2760

Asp Leu Lys Gln Lys Thr Ser Ser Pro Ser Ser Phe Lys Met His
2765                2770                2775
```

```
Ser  Asn  Ser  Gln  Asp  Lys  Glu  Val  Thr  Ile  Leu  Ala  Glu  Gly  Arg
2780                2785                          2790

Arg  Gln  Ser  Gln  Lys  Leu  Pro  Val  Asp  Phe  Glu  Arg  Ser  Phe  Gln
     2795                2800                          2805

Glu  Glu  Lys  Pro  Leu  Glu  Arg  Ser  Asp  Phe  Thr  Gly  Ser  His  Ser
2810                2815                          2820

Glu  Pro  Ser  Thr  Arg  Ala  Asn  Cys  Ser  Asn  Phe  Lys  Glu  Ile  Gln
2825                2830                          2835

Ile  Ser  Asp  Asn  His  Thr  Leu  Ile  Ser  Met  Gly  Arg  Pro  Ser  Ser
2840                2845                          2850

Thr  Leu  Gly  Val  Asn  Arg  Ser  Ser  Ser  Arg  Leu  Gly  Val  Lys  Glu
2855                2860                          2865

Lys  Asn  Val  Thr  Ile  Thr  Pro  Asp  Leu  Pro  Ser  Cys  Ile  Phe  Leu
2870                2875                          2880

Glu  Gln  Arg  Glu  Leu  Phe  Glu  Gln  Ser  Lys  Ala  Pro  Arg  Ala  Asp
2885                2890                          2895

Asp  His  Val  Arg  Lys  His  His  Ser  Pro  Ser  Pro  Gln  His  Gln  Asp
2900                2905                          2910

Tyr  Val  Ala  Pro  Asp  Leu  Pro  Ser  Cys  Ile  Phe  Leu  Glu  Gln  Arg
2915                2920                          2925

Glu  Leu  Phe  Glu  Gln  Cys  Lys  Ala  Pro  Tyr  Val  Asp  His  Gln  Met
2930                2935                          2940

Arg  Glu  Asn  His  Ser  Pro  Leu  Pro  Gln  Gly  Gln  Asp  Ser  Ile  Ala
2945                2950                          2955

Ser  Asp  Leu  Pro  Ser  Pro  Ile  Ser  Leu  Glu  Gln  Cys  Gln  Ser  Lys
2960                2965                          2970

Ala  Pro  Gly  Val  Asp  Asp  Gln  Met  Asn  Lys  His  His  Phe  Pro  Leu
2975                2980                          2985

Pro  Gln  Gly  Gln  Asp  Cys  Val  Val  Glu  Lys  Asn  Asn  Gln  His  Lys
2990                2995                          3000

Pro  Lys  Ser  His  Ile  Ser  Asn  Ile  Asn  Val  Glu  Ala  Lys  Phe  Asn
3005                3010                          3015

Thr  Val  Val  Ser  Gln  Ser  Ala  Pro  Asn  His  Cys  Thr  Leu  Ala  Ala
3020                3025                          3030

Ser  Ala  Ser  Thr  Pro  Pro  Ser  Asn  Arg  Lys  Ala  Leu  Ser  Cys  Val
3035                3040                          3045

His  Ile  Thr  Leu  Cys  Pro  Lys  Thr  Ser  Ser  Lys  Leu  Asp  Ser  Gly
3050                3055                          3060

Thr  Leu  Asp  Glu  Arg  Phe  His  Ser  Leu  Asp  Ala  Ala  Ser  Lys  Ala
3065                3070                          3075

Arg  Met  Asn  Ser  Glu  Phe  Asn  Phe  Asp  Leu  His  Thr  Val  Ser  Ser
3080                3085                          3090

Arg  Ser  Leu  Glu  Pro  Thr  Ser  Lys  Leu  Leu  Thr  Ser  Lys  Pro  Val
3095                3100                         3105

Ala  Gln  Asp  Gln  Glu  Ser  Leu  Gly  Phe  Leu  Gly  Pro  Lys  Ser  Ser
3110                3115                         3120

Leu  Asp  Phe  Gln  Val  Val  Gln  Pro  Ser  Leu  Pro  Asp  Ser  Asn  Thr
3125                3130                         3135

Ile  Thr  Gln  Asp  Leu  Lys  Thr  Ile  Pro  Ser  Gln  Asn  Ser  Gln  Ile
3140                3145                         3150

Val  Thr  Ser  Arg  Gln  Ile  Gln  Val  Asn  Ile  Ser  Asp  Phe  Glu  Gly
3155                3160                         3165

His  Ser  Asn  Pro  Glu  Gly  Thr  Pro  Val  Phe  Ala  Asp  Arg  Leu  Pro
```

-continued

|   |   |   |   |   |   |   |   |   |   |   |
|---|---|---|---|---|---|---|---|---|---|---|
|   | 3170 |   |   | 3175 |   |   | 3180 |   |   |   |
| Glu | Lys | Met | Lys | Thr | Pro | Leu | Ser | Ala | Phe | Ser | Glu | Lys | Leu | Ser |
|   | 3185 |   |   | 3190 |   |   | 3195 |   |   |   |
| Ser | Asp | Ala | Val | Thr | Gln | Ile | Thr | Thr | Glu | Ser | Pro | Glu | Lys | Thr |
|   | 3200 |   |   | 3205 |   |   | 3210 |   |   |   |
| Leu | Phe | Ser | Ser | Glu | Ile | Phe | Ile | Asn | Ala | Glu | Asp | Arg | Gly | His |
|   | 3215 |   |   | 3220 |   |   | 3225 |   |   |   |
| Glu | Ile | Ile | Glu | Pro | Gly | Asn | Gln | Lys | Leu | Arg | Lys | Ala | Pro | Val |
|   | 3230 |   |   | 3235 |   |   | 3240 |   |   |   |
| Lys | Phe | Ala | Ser | Ser | Ser | Val | Gln | Gln | Val | Thr | Phe | Ser | Arg |
|   | 3245 |   |   | 3250 |   |   | 3255 |   |   |   |
| Gly | Thr | Asp | Gly | Gln | Pro | Leu | Leu | Leu | Pro | Tyr | Lys | Pro | Ser | Gly |
|   | 3260 |   |   | 3265 |   |   | 3270 |   |   |   |
| Ser | Thr | Lys | Met | Tyr | Tyr | Val | Pro | Gln | Leu | Arg | Gln | Ile | Pro | Pro |
|   | 3275 |   |   | 3280 |   |   | 3285 |   |   |   |
| Ser | Pro | Asp | Ser | Lys | Ser | Asp | Thr | Thr | Val | Glu | Ser | Ser | His | Ser |
|   | 3290 |   |   | 3295 |   |   | 3300 |   |   |   |
| Gly | Ser | Asn | Asp | Ala | Ile | Ala | Pro | Asp | Phe | Pro | Ala | Gln | Val | Leu |
|   | 3305 |   |   | 3310 |   |   | 3315 |   |   |   |
| Gly | Thr | Arg | Asp | Asp | Asp | Leu | Ser | Ala | Thr | Val | Asn | Ile | Lys | His |
|   | 3320 |   |   | 3325 |   |   | 3330 |   |   |   |
| Lys | Glu | Gly | Ile | Tyr | Ser | Lys | Arg | Val | Val | Thr | Lys | Ala | Ser | Leu |
|   | 3335 |   |   | 3340 |   |   | 3345 |   |   |   |
| Pro | Val | Gly | Glu | Lys | Pro | Leu | Gln | Asn | Glu | Asn | Ala | Asp | Ala | Ser |
|   | 3350 |   |   | 3355 |   |   | 3360 |   |   |   |
| Val | Gln | Val | Leu | Ile | Thr | Gly | Asp | Glu | Asn | Leu | Ser | Asp | Lys | Lys |
|   | 3365 |   |   | 3370 |   |   | 3375 |   |   |   |
| Gln | Gln | Glu | Ile | His | Ser | Thr | Arg | Ala | Val | Thr | Glu | Ala | Ala | Gln |
|   | 3380 |   |   | 3385 |   |   | 3390 |   |   |   |
| Ala | Lys | Glu | Lys | Glu | Ser | Leu | Gln | Lys | Asp | Thr | Ala | Asp | Ser | Ser |
|   | 3395 |   |   | 3400 |   |   | 3405 |   |   |   |
| Ala | Ala | Ala | Ala | Ala | Glu | His | Ser | Ala | Gln | Val | Gly | Asp | Pro | Glu |
|   | 3410 |   |   | 3415 |   |   | 3420 |   |   |   |
| Met | Lys | Asn | Leu | Pro | Asp | Thr | Lys | Ala | Ile | Thr | Gln | Lys | Glu | Glu |
|   | 3425 |   |   | 3430 |   |   | 3435 |   |   |   |
| Ile | His | Arg | Lys | Lys | Thr | Val | Pro | Glu | Glu | Ala | Trp | Pro | Asn | Asn |
|   | 3440 |   |   | 3445 |   |   | 3450 |   |   |   |
| Lys | Glu | Ser | Leu | Gln | Ile | Asn | Ile | Glu | Glu | Ser | Glu | Cys | His | Ser |
|   | 3455 |   |   | 3460 |   |   | 3465 |   |   |   |
| Glu | Phe | Glu | Asn | Thr | Thr | Arg | Ser | Val | Phe | Arg | Ser | Ala | Lys | Phe |
|   | 3470 |   |   | 3475 |   |   | 3480 |   |   |   |
| Tyr | Ile | His | His | Pro | Val | His | Leu | Pro | Ser | Asp | Gln | Asp | Ile | Cys |
|   | 3485 |   |   | 3490 |   |   | 3495 |   |   |   |
| His | Glu | Ser | Leu | Gly | Lys | Ser | Val | Phe | Met | Arg | His | Ser | Trp | Lys |
|   | 3500 |   |   | 3505 |   |   | 3510 |   |   |   |
| Asp | Phe | Phe | Gln | His | His | Pro | Asp | Lys | His | Arg | Glu | His | Met | Cys |
|   | 3515 |   |   | 3520 |   |   | 3525 |   |   |   |
| Leu | Pro | Leu | Pro | Tyr | Gln | Asn | Met | Asp | Lys | Thr | Lys | Thr | Asp | Tyr |
|   | 3530 |   |   | 3535 |   |   | 3540 |   |   |   |
| Thr | Arg | Ile | Lys | Ser | Leu | Ser | Ile | Asn | Val | Asn | Leu | Gly | Asn | Lys |
|   | 3545 |   |   | 3550 |   |   | 3555 |   |   |   |
| Glu | Val | Met | Asp | Thr | Thr | Lys | Ser | Gln | Val | Arg | Asp | Tyr | Pro | Lys |
|   | 3560 |   |   | 3565 |   |   | 3570 |   |   |   |

```
His Asn Gly Gln Ile Ser Asp Pro Gln Arg Asp Gln Lys Val Thr
3575                3580                3585
Pro Glu Gln Thr Thr Gln His Thr Val Ser Leu Asn Glu Leu Trp
3590                3595                3600
Asn Lys Tyr Arg Glu Arg Gln Arg Gln Gln Arg Gln Pro Glu Leu
3605                3610                3615
Gly Asp Arg Lys Glu Leu Ser Leu Val Asp Arg Leu Asp Arg Leu
3620                3625                3630
Ala Lys Ile Leu Gln Asn Pro Ile Thr His Ser Leu Gln Val Ser
3635                3640                3645
Glu Ser Thr His Asp Asp Ser Arg Gly Glu Arg Ser Val Lys Glu
3650                3655                3660
Trp Ser Gly Arg Gln Gln Gln Arg Asn Lys Leu Gln Lys Lys Lys
3665                3670                3675
Arg Phe Lys Ser Leu Glu Lys Ser His Lys Asn Thr Gly Glu Leu
3680                3685                3690
Lys Lys Ser Lys Val Leu Ser His His Arg Ala Gly Arg Ser Asn
3695                3700                3705
Gln Ile Lys Ile Glu Gln Ile Lys Phe Asp Lys Tyr Ile Leu Ser
3710                3715                3720
Lys Gln Pro Gly Phe Asn Tyr Ile Ser Asn Thr Ser Ser Asp Cys
3725                3730                3735
Arg Pro Ser Glu Glu Ser Glu Leu Leu Thr Asp Thr Thr Thr Asn
3740                3745                3750
Ile Leu Ser Gly Thr Thr Ser Thr Val Glu Ser Asp Ile Leu Thr
3755                3760                3765
Gln Thr Asp Arg Glu Val Ala Leu His Glu Arg Ser Ser Ser Val
3770                3775                3780
Ser Thr Ile Asp Thr Ala Arg Leu Ile Gln Ala Phe Gly His Glu
3785                3790                3795
Arg Val Cys Leu Ser Pro Arg Arg Ile Lys Leu Tyr Ser Ser Ile
3800                3805                3810
Thr Asn Gln Gln Arg Arg Tyr Leu Glu Lys Arg Ser Lys His Ser
3815                3820                3825
Lys Lys Val Leu Asn Thr Gly His Pro Leu Val Thr Ser Glu His
3830                3835                3840
Thr Arg Arg Arg His Ile Gln Val Ala Asn His Val Ile Ser Ser
3845                3850                3855
Asp Ser Ile Ser Ser Ser Ala Ser Ser Phe Leu Ser Ser Asn Ser
3860                3865                3870
Thr Phe Cys Asn Lys Gln Asn Val His Met Leu Asn Lys Gly Ile
3875                3880                3885
Gln Ala Gly Asn Leu Glu Ile Val Asn Gly Ala Lys Lys His Thr
3890                3895                3900
Arg Asp Val Gly Ile Thr Phe Pro Thr Pro Ser Ser Ser Glu Ala
3905                3910                3915
Lys Leu Glu Glu Asn Ser Asp Val Thr Ser Trp Ser Glu Glu Lys
3920                3925                3930
Arg Glu Glu Lys Met Leu Phe Thr Gly Tyr Pro Glu Asp Arg Lys
3935                3940                3945
Leu Lys Lys Asn Lys Lys Asn Ser His Glu Gly Val Ser Trp Phe
3950                3955                3960
```

Val Pro Val Glu Asn Val Glu Ser Arg Ser Lys Lys Glu Asn Val
    3965                3970                3975

Pro Asn Thr Cys Gly Pro Gly Ile Ser Trp Phe Glu Pro Ile Thr
    3980                3985                3990

Lys Thr Arg Pro Trp Arg Glu Pro Leu Arg Glu Gln Asn Cys Gln
    3995                4000                4005

Gly Gln His Leu Asp Gly Arg Gly Tyr Leu Ala Gly Pro Gly Arg
    4010                4015                4020

Glu Ala Gly Arg Asp Leu Leu Arg Pro Phe Val Arg Ala Thr Leu
    4025                4030                4035

Gln Glu Ser Leu Gln Phe His Arg Pro Asp Phe Ile Ser Arg Ser
    4040                4045                4050

Gly Glu Arg Ile Lys Arg Leu Lys Leu Ile Val Gln Glu Arg Lys
    4055                4060                4065

Leu Gln Ser Met Leu Gln Thr Glu Arg Asp Ala Leu Phe Asn Ile
    4070                4075                4080

Asp Arg Glu Arg Gln Gly His Gln Asn Arg Met Cys Pro Leu Pro
    4085                4090                4095

Lys Arg Val Phe Leu Ala Ile Gln Lys Asn Lys Pro Ile Ser Lys
    4100                4105                4110

Lys Glu Met Ile Gln Arg Ser Lys Arg Ile Tyr Glu Gln Leu Pro
    4115                4120                4125

Glu Val Gln Lys Lys Arg Glu Glu Lys Arg Lys Ser Glu Tyr
    4130                4135                4140

Lys Ser Tyr Arg Leu Arg Ala Gln Leu Tyr Lys Lys Arg Val Thr
    4145                4150                4155

Asn Gln Leu Leu Gly Arg Lys Val Pro Trp Asp
    4160                4165

<210> SEQ ID NO 2
<211> LENGTH: 1298
<212> TYPE: PRT
<213> ORGANISM: homo sapiens

<400> SEQUENCE: 2

Met Glu Pro Pro Ser Cys Ile Gln Asp Glu Pro Phe Pro His Pro Leu
1               5                   10                  15

Glu Pro Glu Pro Gly Val Ser Ala Gln Pro Gly Pro Gly Lys Pro Ser
                20                  25                  30

Asp Lys Arg Phe Arg Leu Trp Tyr Val Gly Gly Ser Cys Leu Asp His
            35                  40                  45

Arg Thr Thr Leu Pro Met Leu Pro Trp Leu Met Ala Glu Ile Arg Arg
        50                  55                  60

Arg Ser Gln Lys Pro Glu Ala Gly Gly Cys Gly Ala Pro Ala Ala Arg
65                  70                  75                  80

Glu Val Ile Leu Val Leu Ser Ala Pro Phe Leu Arg Cys Val Pro Ala
                85                  90                  95

Pro Gly Ala Gly Ala Ser Gly Gly Thr Ser Pro Ser Ala Thr Gln Pro
            100                 105                 110

Asn Pro Ala Val Phe Ile Phe Glu His Lys Ala Gln His Ile Ser Arg
        115                 120                 125

Phe Ile His Asn Ser His Asp Leu Thr Tyr Phe Ala Tyr Leu Ile Lys
    130                 135                 140

Ala Gln Pro Asp Asp Pro Glu Ser Gln Met Ala Cys His Val Phe Arg
145                 150                 155                 160

```
Ala Thr Asp Pro Ser Gln Val Pro Asp Val Ile Ser Ser Ile Arg Gln
                165                 170                 175

Leu Ser Lys Ala Ala Met Lys Glu Asp Ala Lys Pro Ser Lys Asp Asn
            180                 185                 190

Glu Asp Ala Phe Tyr Asn Ser Gln Lys Phe Glu Val Leu Tyr Cys Gly
        195                 200                 205

Lys Val Thr Val Thr His Lys Lys Ala Pro Ser Ser Leu Ile Asp Asp
    210                 215                 220

Cys Met Glu Lys Phe Ser Leu His Glu Gln Gln Arg Leu Lys Ile Gln
225                 230                 235                 240

Gly Glu Gln Arg Gly Pro Asp Pro Gly Glu Asp Leu Ala Asp Leu Glu
                245                 250                 255

Val Val Val Pro Gly Ser Pro Gly Asp Cys Leu Pro Glu Glu Ala Asp
            260                 265                 270

Gly Thr Asp Thr His Leu Gly Leu Pro Ala Gly Ala Ser Gln Pro Ala
        275                 280                 285

Leu Thr Ser Ser Arg Val Cys Phe Pro Glu Arg Ile Leu Glu Asp Ser
    290                 295                 300

Gly Phe Asp Glu Gln Gln Glu Phe Arg Ser Arg Cys Ser Ser Val Thr
305                 310                 315                 320

Gly Val Gln Arg Arg Val His Glu Gly Ser Gln Lys Ser Gln Pro Arg
                325                 330                 335

Arg His Ala Ser Ala Pro Ser His Val Gln Pro Ser Asp Ser Glu
            340                 345                 350

Lys Asn Arg Thr Met Leu Phe Gln Val Gly Arg Phe Glu Ile Asn Leu
        355                 360                 365

Ile Ser Pro Asp Thr Lys Ser Val Val Leu Glu Lys Asn Phe Lys Asp
    370                 375                 380

Ile Ser Ser Cys Ser Gln Gly Ile Lys His Val Asp His Phe Gly Phe
385                 390                 395                 400

Ile Cys Arg Glu Ser Pro Glu Pro Gly Leu Ser Gln Tyr Ile Cys Tyr
                405                 410                 415

Val Phe Gln Cys Ala Ser Glu Ser Leu Val Asp Glu Val Met Leu Thr
            420                 425                 430

Leu Lys Gln Ala Phe Ser Thr Ala Ala Ala Leu Gln Ser Ala Lys Thr
        435                 440                 445

Gln Ile Lys Leu Cys Glu Ala Cys Pro Met His Ser Leu His Lys Leu
    450                 455                 460

Cys Glu Arg Ile Glu Gly Leu Tyr Pro Pro Arg Ala Lys Leu Val Ile
465                 470                 475                 480

Gln Arg His Leu Ser Ser Leu Thr Asp Asn Glu Gln Ala Asp Ile Phe
                485                 490                 495

Glu Arg Val Gln Lys Met Lys Pro Val Ser Asp Gln Glu Glu Asn Glu
            500                 505                 510

Leu Val Ile Leu His Leu Arg Gln Leu Cys Glu Ala Lys Gln Lys Thr
        515                 520                 525

His Val His Ile Gly Glu Gly Pro Ser Thr Ile Ser Asn Ser Thr Ile
    530                 535                 540

Pro Glu Asn Ala Thr Ser Ser Gly Arg Phe Lys Leu Asp Ile Leu Lys
545                 550                 555                 560

Asn Lys Ala Lys Arg Ser Leu Thr Ser Ser Leu Glu Asn Ile Phe Ser
                565                 570                 575
```

```
Arg Gly Ala Asn Arg Met Arg Gly Arg Leu Gly Ser Val Asp Ser Phe
            580                 585                 590

Glu Arg Ser Asn Ser Leu Ala Ser Glu Lys Asp Tyr Ser Pro Gly Asp
        595                 600                 605

Ser Pro Pro Gly Thr Pro Pro Ala Ser Pro Pro Ser Ser Ala Trp Gln
    610                 615                 620

Thr Phe Pro Glu Glu Asp Ser Asp Ser Pro Gln Phe Arg Arg Arg Ala
625                 630                 635                 640

His Thr Phe Ser His Pro Pro Ser Ser Thr Lys Arg Lys Leu Asn Leu
                645                 650                 655

Gln Asp Gly Arg Ala Gln Gly Val Arg Ser Pro Leu Leu Arg Gln Ser
            660                 665                 670

Ser Ser Glu Gln Cys Ser Asn Leu Ser Ser Val Arg Arg Met Tyr Lys
        675                 680                 685

Glu Ser Asn Ser Ser Ser Leu Pro Ser Leu His Thr Ser Phe Ser
    690                 695                 700

Ala Pro Ser Phe Thr Ala Pro Ser Phe Leu Lys Ser Phe Tyr Gln Asn
705                 710                 715                 720

Ser Gly Arg Leu Ser Pro Gln Tyr Glu Asn Glu Ile Arg Gln Asp Thr
                725                 730                 735

Ala Ser Glu Ser Ser Asp Gly Glu Gly Arg Lys Arg Thr Ser Ser Thr
            740                 745                 750

Cys Ser Asn Glu Ser Leu Ser Val Gly Gly Thr Ser Val Thr Pro Arg
        755                 760                 765

Arg Ile Ser Trp Arg Gln Arg Ile Phe Leu Arg Val Ala Ser Pro Met
    770                 775                 780

Asn Lys Ser Pro Ser Ala Met Gln Gln Gln Asp Gly Leu Asp Arg Asn
785                 790                 795                 800

Glu Leu Leu Pro Leu Ser Pro Leu Ser Pro Thr Met Glu Glu Glu Pro
                805                 810                 815

Leu Val Val Phe Leu Ser Gly Glu Asp Pro Glu Lys Ile Glu Glu
            820                 825                 830

Arg Lys Lys Ser Lys Glu Leu Arg Ser Leu Trp Arg Lys Ala Ile His
        835                 840                 845

Gln Gln Ile Leu Leu Leu Arg Met Glu Lys Glu Asn Gln Lys Leu Glu
    850                 855                 860

Ala Ser Arg Asp Glu Leu Gln Ser Arg Lys Val Lys Leu Asp Tyr Glu
865                 870                 875                 880

Glu Val Gly Ala Cys Gln Lys Glu Val Leu Ile Thr Trp Asp Lys Lys
                885                 890                 895

Leu Leu Asn Cys Arg Ala Lys Ile Arg Cys Asp Met Glu Asp Ile His
            900                 905                 910

Thr Leu Leu Lys Glu Gly Val Pro Lys Ser Arg Arg Gly Glu Ile Trp
        915                 920                 925

Gln Phe Leu Ala Leu Gln Tyr Arg Leu Arg His Arg Leu Pro Asn Lys
    930                 935                 940

Gln Gln Pro Pro Asp Ile Ser Tyr Lys Glu Leu Leu Lys Gln Leu Thr
945                 950                 955                 960

Ala Gln Gln His Ala Ile Leu Val Asp Leu Gly Arg Thr Phe Pro Thr
                965                 970                 975

His Pro Tyr Phe Ser Val Gln Leu Gly Pro Gly Gln Leu Ser Leu Phe
            980                 985                 990

Asn Leu Leu Lys Ala Tyr Ser Leu  Leu Asp Lys Glu Val  Gly Tyr Cys
```

Gln Gly Ile Ser Phe Val Ala Gly Val Leu Leu Leu His Met Ser
    1010                1015                1020

Glu Glu Gln Ala Phe Glu Met Leu Lys Phe Leu Met Tyr Asp Leu
    1025                1030                1035

Gly Phe Arg Lys Gln Tyr Arg Pro Asp Met Met Ser Leu Gln Ile
    1040                1045                1050

Gln Met Tyr Gln Leu Ser Arg Leu Leu His Asp Tyr His Arg Asp
    1055                1060                1065

Leu Tyr Asn His Leu Glu Glu Asn Glu Ile Ser Pro Ser Leu Tyr
    1070                1075                1080

Ala Ala Pro Trp Phe Leu Thr Leu Phe Ala Ser Gln Phe Ser Leu
    1085                1090                1095

Gly Phe Val Ala Arg Val Phe Asp Ile Ile Phe Leu Gln Gly Thr
    1100                1105                1110

Glu Val Ile Phe Lys Val Ala Leu Ser Leu Leu Ser Ser Gln Glu
    1115                1120                1125

Thr Leu Ile Met Glu Cys Glu Ser Phe Glu Asn Ile Val Glu Phe
    1130                1135                1140

Leu Lys Asn Thr Leu Pro Asp Met Asn Thr Ser Glu Met Glu Lys
    1145                1150                1155

Ile Ile Thr Gln Val Phe Glu Met Asp Ile Ser Lys Gln Leu His
    1160                1165                1170

Ala Tyr Glu Val Glu Tyr His Val Leu Gln Asp Glu Leu Gln Glu
    1175                1180                1185

Ser Ser Tyr Ser Cys Glu Asp Ser Glu Thr Leu Glu Lys Leu Glu
    1190                1195                1200

Arg Ala Asn Ser Gln Leu Lys Arg Gln Asn Met Asp Leu Leu Glu
    1205                1210                1215

Lys Leu Gln Val Ala His Thr Lys Ile Gln Ala Leu Glu Ser Asn
    1220                1225                1230

Leu Glu Asn Leu Leu Thr Arg Glu Thr Lys Met Lys Ser Leu Ile
    1235                1240                1245

Arg Thr Leu Glu Gln Glu Lys Met Ala Tyr Gln Lys Thr Val Glu
    1250                1255                1260

Gln Leu Arg Lys Leu Leu Pro Ala Asp Ala Leu Val Asn Cys Asp
    1265                1270                1275

Leu Leu Leu Arg Asp Leu Asn Cys Asn Pro Asn Asn Lys Ala Lys
    1280                1285                1290

Ile Gly Asn Lys Pro
    1295

<210> SEQ ID NO 3
<211> LENGTH: 1235
<212> TYPE: PRT
<213> ORGANISM: homo sapiens

<400> SEQUENCE: 3

Met Glu Pro Pro Ser Cys Ile Gln Asp Glu Pro Phe Pro His Pro Leu
1               5                   10                  15

Glu Pro Glu Pro Gly Val Ser Ala Gln Pro Gly Pro Gly Lys Pro Ser
                20                  25                  30

Asp Lys Arg Phe Arg Leu Trp Tyr Val Gly Gly Ser Cys Leu Asp His
        35                  40                  45

```
Arg Thr Thr Leu Pro Met Leu Pro Trp Leu Met Ala Glu Ile Arg Arg
 50                  55                  60

Arg Ser Gln Lys Pro Glu Ala Gly Gly Cys Gly Ala Pro Ala Ala Arg
 65                  70                  75                  80

Glu Val Ile Leu Val Leu Ser Ala Pro Phe Leu Arg Cys Val Pro Ala
                 85                  90                  95

Pro Gly Ala Gly Ala Ser Gly Gly Thr Ser Pro Ser Ala Thr Gln Pro
            100                 105                 110

Asn Pro Ala Val Phe Ile Phe Glu His Lys Ala Gln His Ile Ser Arg
            115                 120                 125

Phe Ile His Asn Ser His Asp Leu Thr Tyr Phe Ala Tyr Leu Ile Lys
    130                 135                 140

Ala Gln Pro Asp Asp Pro Glu Ser Gln Met Ala Cys His Val Phe Arg
145                 150                 155                 160

Ala Thr Asp Pro Ser Gln Val Pro Asp Val Ile Ser Ser Ile Arg Gln
                165                 170                 175

Leu Ser Lys Ala Ala Met Lys Glu Asp Ala Lys Pro Ser Lys Asp Asn
            180                 185                 190

Glu Asp Ala Phe Tyr Asn Ser Gln Lys Phe Glu Val Leu Tyr Cys Gly
            195                 200                 205

Lys Val Thr Val Thr His Lys Lys Ala Pro Ser Ser Leu Ile Asp Asp
210                 215                 220

Cys Met Glu Lys Phe Ser Leu His Glu Gln Gln Arg Leu Lys Ile Gln
225                 230                 235                 240

Gly Glu Gln Arg Gly Pro Asp Pro Gly Glu Asp Leu Ala Asp Leu Glu
                245                 250                 255

Val Val Val Pro Gly Ser Pro Gly Asp Cys Leu Pro Glu Glu Ala Asp
            260                 265                 270

Gly Thr Asp Thr His Leu Gly Leu Pro Ala Gly Ala Ser Gln Pro Ala
            275                 280                 285

Leu Thr Ser Ser Arg Val Cys Phe Pro Glu Arg Ile Leu Glu Asp Ser
            290                 295                 300

Gly Phe Asp Glu Gln Gln Glu Phe Arg Ser Arg Cys Ser Ser Val Thr
305                 310                 315                 320

Gly Val Gln Arg Arg Val His Glu Gly Ser Gln Lys Ser Gln Pro Arg
                325                 330                 335

Arg Arg His Ala Ser Ala Pro Ser His Val Gln Pro Ser Asp Ser Glu
            340                 345                 350

Lys Asn Arg Thr Met Leu Phe Gln Val Gly Arg Phe Glu Ile Asn Leu
            355                 360                 365

Ile Ser Pro Asp Thr Lys Ser Val Val Leu Glu Lys Asn Phe Lys Asp
    370                 375                 380

Ile Ser Ser Cys Ser Gln Gly Ile Lys His Val Asp His Phe Gly Phe
385                 390                 395                 400

Ile Cys Arg Glu Ser Pro Glu Pro Gly Leu Ser Gln Tyr Ile Cys Tyr
                405                 410                 415

Val Phe Gln Cys Ala Ser Glu Ser Leu Val Asp Glu Val Met Leu Thr
            420                 425                 430

Leu Lys Gln Ala Phe Ser Thr Ala Ala Ala Leu Gln Ser Ala Lys Thr
            435                 440                 445

Gln Ile Lys Leu Cys Glu Ala Cys Pro Met His Ser Leu His Lys Leu
450                 455                 460

Cys Glu Arg Ile Glu Gly Leu Tyr Pro Pro Arg Ala Lys Leu Val Ile
```

```
                465                 470                 475                 480
           Gln Arg His Leu Ser Ser Leu Thr Asp Asn Glu Gln Ala Asp Ile Phe
                           485                 490                 495
           Glu Arg Val Gln Lys Met Lys Pro Val Ser Asp Gln Glu Glu Asn Glu
                           500                 505                 510
           Leu Val Ile Leu His Leu Arg Gln Leu Cys Glu Ala Lys Gln Lys Thr
                           515                 520                 525
           His Val His Ile Gly Glu Gly Pro Ser Thr Ile Ser Asn Ser Thr Ile
                           530                 535                 540
           Pro Glu Asn Ala Thr Ser Ser Gly Arg Phe Lys Leu Asp Ile Leu Lys
           545                 550                 555                 560
           Asn Lys Ala Lys Arg Ser Leu Thr Ser Ser Leu Glu Asn Ile Phe Ser
                           565                 570                 575
           Arg Gly Ala Asn Arg Met Arg Gly Arg Leu Gly Ser Val Asp Ser Phe
                           580                 585                 590
           Glu Arg Ser Asn Ser Leu Ala Ser Glu Lys Asp Tyr Ser Pro Gly Asp
                           595                 600                 605
           Ser Pro Pro Gly Thr Pro Pro Ala Ser Pro Pro Ser Ser Ala Trp Gln
                           610                 615                 620
           Thr Phe Pro Glu Glu Asp Ser Asp Ser Pro Gln Phe Arg Arg Arg Ala
           625                 630                 635                 640
           His Thr Phe Ser His Pro Pro Ser Ser Thr Lys Arg Lys Leu Asn Leu
                           645                 650                 655
           Gln Asp Gly Arg Ala Gln Gly Val Arg Ser Pro Leu Leu Arg Gln Ser
                           660                 665                 670
           Ser Ser Glu Gln Cys Ser Asp Gly Glu Gly Arg Lys Arg Thr Ser Ser
                           675                 680                 685
           Thr Cys Ser Asn Glu Ser Leu Ser Val Gly Gly Thr Ser Val Thr Pro
                           690                 695                 700
           Arg Arg Ile Ser Trp Arg Gln Arg Ile Phe Leu Arg Val Ala Ser Pro
           705                 710                 715                 720
           Met Asn Lys Ser Pro Ser Ala Met Gln Gln Gln Asp Gly Leu Asp Arg
                           725                 730                 735
           Asn Glu Leu Leu Pro Leu Ser Pro Leu Ser Pro Thr Met Glu Glu Glu
                           740                 745                 750
           Pro Leu Val Val Phe Leu Ser Gly Glu Asp Pro Glu Lys Ile Glu
                           755                 760                 765
           Glu Arg Lys Lys Ser Lys Glu Leu Arg Ser Leu Trp Arg Lys Ala Ile
                           770                 775                 780
           His Gln Gln Ile Leu Leu Leu Arg Met Glu Lys Glu Asn Gln Lys Leu
           785                 790                 795                 800
           Glu Ala Ser Arg Asp Glu Leu Gln Ser Arg Lys Val Lys Leu Asp Tyr
                           805                 810                 815
           Glu Glu Val Gly Ala Cys Gln Lys Glu Val Leu Ile Thr Trp Asp Lys
                           820                 825                 830
           Lys Leu Leu Asn Cys Arg Ala Lys Ile Arg Cys Asp Met Glu Asp Ile
                           835                 840                 845
           His Thr Leu Leu Lys Glu Gly Val Pro Lys Ser Arg Arg Gly Glu Ile
                           850                 855                 860
           Trp Gln Phe Leu Ala Leu Gln Tyr Arg Leu Arg His Arg Leu Pro Asn
           865                 870                 875                 880
           Lys Gln Gln Pro Pro Asp Ile Ser Tyr Lys Glu Leu Leu Lys Gln Leu
                           885                 890                 895
```

Thr Ala Gln Gln His Ala Ile Leu Val Asp Leu Gly Arg Thr Phe Pro
            900                 905                 910

Thr His Pro Tyr Phe Ser Val Gln Leu Gly Pro Gly Gln Leu Ser Leu
        915                 920                 925

Phe Asn Leu Leu Lys Ala Tyr Ser Leu Leu Asp Lys Glu Val Gly Tyr
    930                 935                 940

Cys Gln Gly Ile Ser Phe Val Ala Gly Val Leu Leu His Met Ser
945                 950                 955                 960

Glu Glu Gln Ala Phe Glu Met Leu Lys Phe Leu Met Tyr Asp Leu Gly
                965                 970                 975

Phe Arg Lys Gln Tyr Arg Pro Asp Met Met Ser Leu Gln Ile Gln Met
            980                 985                 990

Tyr Gln Leu Ser Arg Leu Leu His Asp Tyr His Arg Asp Leu Tyr Asn
        995                 1000                1005

His Leu Glu Glu Asn Glu Ile Ser Pro Ser Leu Tyr Ala Ala Pro
    1010                1015                1020

Trp Phe Leu Thr Leu Phe Ala Ser Gln Phe Ser Leu Gly Phe Val
    1025                1030                1035

Ala Arg Val Phe Asp Ile Ile Phe Leu Gln Gly Thr Glu Val Ile
    1040                1045                1050

Phe Lys Val Ala Leu Ser Leu Leu Ser Ser Gln Glu Thr Leu Ile
    1055                1060                1065

Met Glu Cys Glu Ser Phe Glu Asn Ile Val Glu Phe Leu Lys Asn
    1070                1075                1080

Thr Leu Pro Asp Met Asn Thr Ser Glu Met Glu Lys Ile Ile Thr
    1085                1090                1095

Gln Val Phe Glu Met Asp Ile Ser Lys Gln Leu His Ala Tyr Glu
    1100                1105                1110

Val Glu Tyr His Val Leu Gln Asp Glu Leu Gln Glu Ser Ser Tyr
    1115                1120                1125

Ser Cys Glu Asp Ser Glu Thr Leu Glu Lys Leu Glu Arg Ala Asn
    1130                1135                1140

Ser Gln Leu Lys Arg Gln Asn Met Asp Leu Leu Glu Lys Leu Gln
    1145                1150                1155

Val Ala His Thr Lys Ile Gln Ala Leu Glu Ser Asn Leu Glu Asn
    1160                1165                1170

Leu Leu Thr Arg Glu Thr Lys Met Lys Ser Leu Ile Arg Thr Leu
    1175                1180                1185

Glu Gln Glu Lys Met Ala Tyr Gln Lys Thr Val Glu Gln Leu Arg
    1190                1195                1200

Lys Leu Leu Pro Ala Asp Ala Leu Val Asn Cys Asp Leu Leu Leu
    1205                1210                1215

Arg Asp Leu Asn Cys Asn Pro Asn Asn Lys Ala Lys Ile Gly Asn
    1220                1225                1230

Lys Pro
    1235

<210> SEQ ID NO 4
<211> LENGTH: 672
<212> TYPE: PRT
<213> ORGANISM: homo sapiens

<400> SEQUENCE: 4

Met Ala Asp Val Phe Pro Gly Asn Asp Ser Thr Ala Ser Gln Asp Val

-continued

```
  1               5                  10                 15
Ala Asn Arg Phe Ala Arg Lys Gly Ala Leu Arg Gln Lys Asn Val His
                 20                 25                 30
Glu Val Lys Asp His Lys Phe Ile Ala Arg Phe Phe Lys Gln Pro Thr
                 35                 40                 45
Phe Cys Ser His Cys Thr Asp Phe Ile Trp Gly Phe Gly Lys Gln Gly
 50                 55                 60
Phe Gln Cys Gln Val Cys Cys Phe Val Val His Lys Arg Cys His Glu
 65                 70                 75                 80
Phe Val Thr Phe Ser Cys Pro Gly Ala Asp Lys Gly Pro Asp Thr Asp
                 85                 90                 95
Asp Pro Arg Ser Lys His Lys Phe Lys Ile His Thr Tyr Gly Ser Pro
                100                105                110
Thr Phe Cys Asp His Cys Gly Ser Leu Leu Tyr Gly Leu Ile His Gln
                115                120                125
Gly Met Lys Cys Asp Thr Cys Asp Met Asn Val His Lys Gln Cys Val
130                135                140
Ile Asn Val Pro Ser Leu Cys Gly Met Asp His Thr Glu Lys Arg Gly
145                150                155                160
Arg Ile Tyr Leu Lys Ala Glu Val Ala Asp Glu Lys Leu His Val Thr
                165                170                175
Val Arg Asp Ala Lys Asn Leu Ile Pro Met Asp Pro Asn Gly Leu Ser
                180                185                190
Asp Pro Tyr Val Lys Leu Lys Leu Ile Pro Asp Pro Lys Asn Glu Ser
                195                200                205
Lys Gln Lys Thr Lys Thr Ile Arg Ser Thr Leu Asn Pro Gln Trp Asn
210                215                220
Glu Ser Phe Thr Phe Lys Leu Lys Pro Ser Asp Lys Asp Arg Arg Leu
225                230                235                240
Ser Val Glu Ile Trp Asp Trp Asp Arg Thr Thr Arg Asn Asp Phe Met
                245                250                255
Gly Ser Leu Ser Phe Gly Val Ser Glu Leu Met Lys Met Pro Ala Ser
                260                265                270
Gly Trp Tyr Lys Leu Leu Asn Gln Glu Glu Gly Glu Tyr Tyr Asn Val
                275                280                285
Pro Ile Pro Glu Gly Asp Glu Glu Gly Asn Met Glu Leu Arg Gln Lys
                290                295                300
Phe Glu Lys Ala Lys Leu Gly Pro Ala Gly Asn Lys Val Ile Ser Pro
305                310                315                320
Ser Glu Asp Arg Lys Gln Pro Ser Asn Asn Leu Asp Arg Val Lys Leu
                325                330                335
Thr Asp Phe Asn Phe Leu Met Val Leu Gly Lys Gly Ser Phe Gly Lys
                340                345                350
Val Met Leu Ala Asp Arg Lys Gly Thr Glu Glu Leu Tyr Ala Ile Lys
                355                360                365
Ile Leu Lys Lys Asp Val Val Ile Gln Asp Asp Asp Val Glu Cys Thr
370                375                380
Met Val Glu Lys Arg Val Leu Ala Leu Leu Asp Lys Pro Pro Phe Leu
385                390                395                400
Thr Gln Leu His Ser Cys Phe Gln Thr Val Asp Arg Leu Tyr Phe Val
                405                410                415
Met Glu Tyr Val Asn Gly Gly Asp Leu Met Tyr His Ile Gln Gln Val
                420                425                430
```

-continued

Gly Lys Phe Lys Glu Pro Gln Ala Val Phe Tyr Ala Ala Glu Ile Ser
            435                 440                 445

Ile Gly Leu Phe Phe Leu His Lys Arg Gly Ile Ile Tyr Arg Asp Leu
    450                 455                 460

Lys Leu Asp Asn Val Met Leu Asp Ser Glu Gly His Ile Lys Ile Ala
465                 470                 475                 480

Asp Phe Gly Met Cys Lys Glu His Met Met Asp Gly Val Thr Thr Arg
                485                 490                 495

Thr Phe Cys Gly Thr Pro Asp Tyr Ile Ala Pro Glu Ile Ile Ala Tyr
            500                 505                 510

Gln Pro Tyr Gly Lys Ser Val Asp Trp Trp Ala Tyr Gly Val Leu Leu
            515                 520                 525

Tyr Glu Met Leu Ala Gly Gln Pro Pro Phe Asp Gly Glu Asp Glu Asp
            530                 535                 540

Glu Leu Phe Gln Ser Ile Met Glu His Asn Val Ser Tyr Pro Lys Ser
545                 550                 555                 560

Leu Ser Lys Glu Ala Val Ser Ile Cys Lys Gly Leu Met Thr Lys His
                565                 570                 575

Pro Ala Lys Arg Leu Gly Cys Gly Pro Glu Gly Glu Arg Asp Val Arg
            580                 585                 590

Glu His Ala Phe Phe Arg Arg Ile Asp Trp Glu Lys Leu Glu Asn Arg
            595                 600                 605

Glu Ile Gln Pro Pro Phe Lys Pro Lys Val Cys Gly Lys Gly Ala Glu
            610                 615                 620

Asn Phe Asp Lys Phe Phe Thr Arg Gly Gln Pro Val Leu Thr Pro Pro
625                 630                 635                 640

Asp Gln Leu Val Ile Ala Asn Ile Asp Gln Ser Asp Phe Glu Gly Phe
                645                 650                 655

Ser Tyr Val Asn Pro Gln Phe Val His Pro Ile Leu Gln Ser Ala Val
            660                 665                 670

<210> SEQ ID NO 5
<211> LENGTH: 17
<212> TYPE: PRT
<213> ORGANISM: artificial sequence
<220> FEATURE:
<223> OTHER INFORMATION: Peptide 1

<400> SEQUENCE: 5

Leu Asp Ser Asp Ser His Tyr Gly Pro Gln His Leu Glu Ser Ile Asp
1               5                   10                  15

Asp

<210> SEQ ID NO 6
<211> LENGTH: 9
<212> TYPE: PRT
<213> ORGANISM: artificial sequence
<220> FEATURE:
<223> OTHER INFORMATION: Peptide 2

<400> SEQUENCE: 6

Asp Ser His Gln Thr Glu Glu Thr Leu
1               5

<210> SEQ ID NO 7
<211> LENGTH: 10
<212> TYPE: PRT
<213> ORGANISM: artificial sequence -continued

```
<220> FEATURE:
<223> OTHER INFORMATION: peptide 3

<400> SEQUENCE: 7

Gln Gln Thr Leu Pro Glu Ser His Leu Pro
1               5                   10

<210> SEQ ID NO 8
<211> LENGTH: 10
<212> TYPE: PRT
<213> ORGANISM: artificial sequence
<220> FEATURE:
<223> OTHER INFORMATION: peptide 4

<400> SEQUENCE: 8

Gln Ala Leu Leu Asp Ser His Leu Pro Glu
1               5                   10

<210> SEQ ID NO 9
<211> LENGTH: 9
<212> TYPE: PRT
<213> ORGANISM: artificial sequence
<220> FEATURE:
<223> OTHER INFORMATION: peptide 5

<400> SEQUENCE: 9

Pro Ala Asp Gln Met Thr Asp Thr Pro
1               5

<210> SEQ ID NO 10
<211> LENGTH: 12
<212> TYPE: PRT
<213> ORGANISM: artificial sequence
<220> FEATURE:
<223> OTHER INFORMATION: peptide 6

<400> SEQUENCE: 10

His Ile Pro Glu Glu Ala Gln Lys Val Ser Ala Val
1               5                   10

<210> SEQ ID NO 11
<211> LENGTH: 7
<212> TYPE: PRT
<213> ORGANISM: artificial sequence
<220> FEATURE:
<223> OTHER INFORMATION: peptide 7

<400> SEQUENCE: 11

Ser Cys Ile Phe Leu Glu Gln
1               5

<210> SEQ ID NO 12
<211> LENGTH: 21
<212> TYPE: DNA
<213> ORGANISM: artificial sequence
<220> FEATURE:
<223> OTHER INFORMATION: primer

<400> SEQUENCE: 12 acaactttc atggctccag t                                        21

<210> SEQ ID NO 13
<211> LENGTH: 21
<212> TYPE: DNA
<213> ORGANISM: artificial sequence
<220> FEATURE:
<223> OTHER INFORMATION: primer
```

<400> SEQUENCE: 13
ttggctcaga gacagttgaa a                                              21

<210> SEQ ID NO 14
<211> LENGTH: 337
<212> TYPE: PRT
<213> ORGANISM: artificial sequence
<220> FEATURE:
<223> OTHER INFORMATION: PKCalpha domain

<400> SEQUENCE: 14

Leu Thr Asp Phe Asn Phe Leu Met Val Leu Gly Lys Gly Ser Phe Gly
1               5                   10                  15

Lys Val Met Leu Ala Asp Arg Lys Gly Thr Glu Glu Leu Tyr Ala Ile
            20                  25                  30

Lys Ile Leu Lys Lys Asp Val Val Ile Gln Asp Asp Val Glu Cys
        35                  40                  45

Thr Met Val Glu Lys Arg Val Leu Ala Leu Leu Asp Lys Pro Pro Phe
    50                  55                  60

Leu Thr Gln Leu His Ser Cys Phe Gln Thr Val Asp Arg Leu Tyr Phe
65                  70                  75                  80

Val Met Glu Tyr Val Asn Gly Gly Asp Leu Met Tyr His Ile Gln Gln
                85                  90                  95

Val Gly Lys Phe Lys Glu Pro Gln Ala Val Phe Tyr Ala Ala Glu Ile
            100                 105                 110

Ser Ile Gly Leu Phe Phe Leu His Lys Arg Gly Ile Ile Tyr Arg Asp
        115                 120                 125

Leu Lys Leu Asp Asn Val Met Leu Asp Ser Glu Gly His Ile Lys Ile
    130                 135                 140

Ala Asp Phe Gly Met Cys Lys Glu His Met Met Asp Gly Val Thr Thr
145                 150                 155                 160

Arg Thr Phe Cys Gly Thr Pro Asp Tyr Ile Ala Pro Glu Ile Ile Ala
                165                 170                 175

Tyr Gln Pro Tyr Gly Lys Ser Val Asp Trp Trp Ala Tyr Gly Val Leu
            180                 185                 190

Leu Tyr Glu Met Leu Ala Gly Gln Pro Pro Phe Asp Gly Glu Asp Glu
        195                 200                 205

Asp Glu Leu Phe Gln Ser Ile Met Glu His Asn Val Ser Tyr Pro Lys
    210                 215                 220

Ser Leu Ser Lys Glu Ala Val Ser Ile Cys Lys Gly Leu Met Thr Lys
225                 230                 235                 240

His Pro Ala Lys Arg Leu Gly Cys Gly Pro Glu Gly Glu Arg Asp Val
                245                 250                 255

Arg Glu His Ala Phe Phe Arg Arg Ile Asp Trp Glu Lys Leu Glu Asn
            260                 265                 270

Arg Glu Ile Gln Pro Pro Phe Lys Pro Lys Val Cys Gly Lys Gly Ala
        275                 280                 285

Glu Asn Phe Asp Lys Phe Phe Thr Arg Gly Gln Pro Val Leu Thr Pro
    290                 295                 300

Pro Asp Gln Leu Val Ile Ala Asn Ile Asp Gln Ser Asp Phe Glu Gly
305                 310                 315                 320

Phe Ser Tyr Val Asn Pro Gln Phe Val His Pro Ile Leu Gln Ser Ala
                325                 330                 335

Val

<210> SEQ ID NO 15
<211> LENGTH: 1014
<212> TYPE: DNA
<213> ORGANISM: artificial sequence
<220> FEATURE:
<223> OTHER INFORMATION: PCKalpha domain

<400> SEQUENCE: 15

```
ctcacggact tcaatttcct catggtgttg ggaaagggga gttttggaaa ggtgatgctt      60
gccgacagga agggcacaga agaactgtat gcaatcaaaa tcctgaagaa ggatgtggtg     120
attcaggatg atgacgtgga gtgcaccatg gtagaaaagc gagtcttggc cctgcttgac     180
aaaccccgt tcttgacgca gctgcactcc tgcttccaga cagtggatcg gctgtacttc     240
gtcatggaat atgtcaacgg tggggacctc atgtaccaca ttcagcaagt aggaaaattt     300
aaggaaccac aagcagtatt ctatgcggca gagatttcca tcggattgtt ctttcttcat     360
aaaagaggaa tcatttatag ggatctgaag ttagataacg tcatgttgga ttcagaagga     420
catatcaaaa ttgctgactt tgggatgtgc aaggaacaca tgatggatgg agtcacgacc     480
aggaccttct gtgggactcc agattatatc gccccagaga taatcgctta tcagccgtat     540
ggaaaatctg tggactggtg ggcctatggc gtcctgttgt atgaaatgct tgccgggcag     600
cctccatttg atggtgaaga tgaagacgag ctatttcagt ctatcatgga gcacaacgtt     660
tcctatccaa atccttgtc caaggaggct gtttctatct gcaaaggact gatgaccaaa     720
cacccagcca agcggctggg ctgtgggcct gaggggagag gggacgtgag agagcatgcc     780
ttcttccgga ggatcgactg gaaaaaactg gagaacaggg agatccagcc accattcaag     840
cccaaagtgt gtggcaaagg agcagagaac tttgacaagt tcttcacacg aggacagccc     900
gtcttaacac cacctgatca gctggttatt gctaacatag accagtctga ttttgaaggg     960
ttctcgtatg tcaacccca gtttgtgcac cccatcttac agagtgcagt atga           1014
```

<210> SEQ ID NO 16
<211> LENGTH: 64
<212> TYPE: DNA
<213> ORGANISM: artificial sequence
<220> FEATURE:
<223> OTHER INFORMATION: Primer

<400> SEQUENCE: 16

```
gtacgaattc gccaccatgg attacaagga tgacgacgat aagctcacgg acttcaattt      60
cctc                                                                   64
```

<210> SEQ ID NO 17
<211> LENGTH: 34
<212> TYPE: DNA
<213> ORGANISM: artificial sequence
<220> FEATURE:
<223> OTHER INFORMATION: primer

<400> SEQUENCE: 17

```
tagcggatcc tcatactgca ctctgtaaga tggg                                  34
```

<210> SEQ ID NO 18
<211> LENGTH: 8
<212> TYPE: PRT
<213> ORGANISM: artificial sequence
<220> FEATURE:
<223> OTHER INFORMATION: arginine rich peptide

```
<400> SEQUENCE: 18

Arg Arg Arg Arg Arg Arg Arg Arg
1               5

<210> SEQ ID NO 19
<211> LENGTH: 15
<212> TYPE: PRT
<213> ORGANISM: artificial sequence
<220> FEATURE:
<223> OTHER INFORMATION: arginine rich peptide

<400> SEQUENCE: 19

Arg Arg Pro Arg Arg Pro Arg Arg Pro Arg Arg Pro Arg Arg Pro
1               5                   10                  15

<210> SEQ ID NO 20
<211> LENGTH: 16
<212> TYPE: PRT
<213> ORGANISM: artificial sequence
<220> FEATURE:
<223> OTHER INFORMATION: antennapedia peptide

<400> SEQUENCE: 20

Arg Gln Ile Lys Ile Trp Phe Gln Asn Arg Arg Met Lys Trp Lys Lys
1               5                   10                  15

<210> SEQ ID NO 21
<211> LENGTH: 11
<212> TYPE: PRT
<213> ORGANISM: artificial sequence
<220> FEATURE:
<223> OTHER INFORMATION: HIV-Tat

<400> SEQUENCE: 21

Tyr Gly Arg Lys Lys Arg Arg Gln Arg Arg Arg
1               5                   10
```

TARGET FOR DIABETES TREATMENT AND PREVENTION

CROSS-REFERENCE TO RELATED APPLICATION

This application is the U.S. national stage application of International Patent Application No. PCT/EP2015/051856, filed Jan. 29, 2015.

The Sequence Listing for this application is labeled "Seq-List.txt" which was created on Jul. 8, 2016 and is 71 KB. The entire content of the sequence listing is incorporated herein by reference in its entirety.

FIELD OF THE INVENTION

The present invention relates to the field of the medicine. More particularly, it relates to diabetes.

BACKGROUND OF THE INVENTION

Diabetes mellitus or diabetes is a group of metabolic diseases in which a person has high blood sugar, either because the pancreas does not produce enough insulin, or because cells do not respond to the insulin that is produced.

There are three main types of diabetes:
Type 1 results from the body's failure to produce insulin, and currently requires the person to inject insulin or wear an insulin pump.
Type 2 results from insulin resistance, a condition in which cells fail to use insulin properly.
The third one is called gestational diabetes and occurs with pregnant women.

Rates of type 2 diabetes have increased markedly since 1960 in parallel with obesity: As of 2010 there are approximately 285 million people with the disease compared to around 30 million in 1985. Long-term complications from high blood sugar can include heart diseases, strokes, diabetic retinopathy, chronic renal failure which may require dialysis and poor circulation in the limbs leading to amputations. Nonketotic hyperosmolar coma may occur.

It has been reported that hyperglycemia participates in the onset and progressive impairment of diabetes mellitus, i.e., glucose toxicity theory. Namely, chronic hyperglycemia leads to decrease insulin secretion and further to decrease insulin sensitivity, and as a result, the blood glucose concentration is increased so that diabetes mellitus is self-exacerbated. Therefore, by treating hyperglycemia, the aforementioned self-exacerbating cycle is interrupted so that the prophylaxis or treatment of diabetes mellitus is made possible.

Unfortunately, existing treatments do not succeed in restoring normoglycaemia in the long term, since beta-cell function declines over time. Moreover, there is presently no single drug able to reverse all aspects of the disease.

The progressive nature of type 2 diabetes means that many patients will eventually require a combination of oral hypoglycaemic medication, possibly together with insulin and/or exenatide injections. Anti-diabetic agents have been developed in order to counteract the main mechanisms involved in type 2 diabetes: insulin resistance (biguanides and thiazolidinediones) and insulin secretion (sulfonylureas, glinides, dipeptidylpeptidase-4 inhibitors, glucagon-like peptide 1 receptor agonists), agents that delay absorption of glucose by gastrointestinal tract or promote weight loss and newer agents that promote renal glucose excretion. However, most of these medications have been shown to have deleterious side effects such as weight gain, peripheral edema or congestive heart failure and there is a major problem with a loss of effectiveness of these agents with long-term use. Thus, despite the increasing number of therapeutic options for glycaemic control, there is a need for alternative and improved medications for the treatment of diabetes and related conditions.

SUMMARY OF THE INVENTION

The inventors identified a new target for treating diabetes, in particular Type 2 diabetes. They made the novel finding that ALMS1 (Alstrom syndrome protein 1) is involved in the regulation by insulin of glucose absorption by mature adipocytes through its binding interactions with key molecules involved in regulation of glucose. Briefly, when insulin binds its receptor, they showed that a protein complex forms around Alms1 (the ALMSome) and is activated, leading to H+ pump activation, GLUT4 receptor translocation and glucose absorption by adipocytes. They also showed that in the absence of Alms1, and thereby prevention of assembly of the ALMSome, glucose cannot be transported into the cells due to a failure of GLUT4 fusion with the cell membrane. Hence, they showed that modulation of ALMS1 complex formation can be used to regulate glucose transport and can thereby be used to circumvent insulin resistance, and treat Type 2 diabetes.

More particularly, the inventors identified two proteins involved in glucose transport regulation by ALMS1, namely TBC1D4 (TBC1 domain family member 4) and αPKC (PKCα or Protein Kinase C alpha type). More particularly, the binding sites of these two glucose regulating proteins on ALMS1 are so close that the simultaneous binding of both proteins is not possible due to steric hindrance. TBC1D4, through its interaction with proteins (i.e., Rab10, Rab14, etc) and ALMS1, regulates the translocation of GLUT4 receptors to the cell membrane. On the other hand, αPKC, when bound to ALMS1, blocks the TBC1D4 binding site and, thereby down-regulates the translocation of GLUT4 receptors to the cell membrane, reducing cellular glucose absorption. They further demonstrated that targeting the interaction of ALMS1 and αPKC is sufficient to trigger glucose absorption in the adipocytes irrespective of the presence of INS. Accordingly, a new therapeutic strategy revealed in this invention is to enhance cellular glucose absorption and reduce hyperglycaemia by blocking the binding of αPKC on ALMS1. Most preferably, the binding of αPKC on ALMS1 is inhibited in such a way that the binding of TBC1D4 on ALMS1 is unaffected or even enhanced.

Accordingly, the present invention relates to a molecule capable of preventing the binding of αPKC to ALMS1 for use for treating or delaying the progression or onset of diabetes mellitus, insulin resistance, diabetic retinopathy, diabetic neuropathy, diabetic nephropathy, insulin resistance, hyperglycemia, obesity, and hyperinsulinaemia. It also relates to the use of such a molecule for the manufacture of a medicament for treating or delaying the progression or onset of diabetes mellitus, insulin resistance, diabetic retinopathy, diabetic neuropathy, diabetic nephropathy, insulin resistance, hyperglycemia, obesity, and hyperinsulinaemia. It also relates to a method for treating or delaying the progression or onset of diabetes mellitus, insulin resistance, diabetic retinopathy, diabetic neuropathy, diabetic nephropathy, insulin resistance, hyperglycemia, obesity, and hyperinsulinaemia, in a subject in need thereof, wherein a therapeutically effective amount of a molecule capable of preventing the binding of αPKC to ALMS1 is administered, thereby increasing the glucose absorption induced by insulin. In a preferred embodiment, the molecule does not interfere with the binding of TBC1D4 to ALMS1. Preferably, the molecule is selected from the group consisting of peptides or polypeptides or peptide mimetics, antibodies, fragments or derivatives thereof, aptamers, Spiegelmers, and chemical compounds. More preferably, the molecule is a peptide less than 50 amino acids, preferably less than 20 amino acids.

In a first preferred embodiment, the molecule is a peptide comprising an amino acid sequence of a fragment of ALMS1 (SEQ ID No 1). Preferably, the molecule is a peptide comprising an amino acid sequence of a fragment of ALMS1 including one or several of the residues which are predicted to mediate the interaction with αPKC, in particular one or several of the residues selected in the list consisting of E17, D58, S59, G62, H65, L66, Q736, T737, E738, D828, 5829, T1088, D1089, A1169, Q1170, F2882, L2883, and E2884. In a very particular embodiment, the molecule is a peptide comprising or consisting of one of the following sequences:

LDSDSHYGPQHLESIDD (SEQ ID No 5);
DSHQTEETL (SEQ ID No 6);
QQTLPESHLP (SEQ ID No 7);
QALLDSHLPE (SEQ ID No 8);
PADQMTDTP (SEQ ID No 9);
HIPEEAQKVSAV (SEQ ID No 10);
SCIFLEQ (SEQ ID No 11), and
a fragment thereof comprising 6 contiguous amino acids.

In a second preferred embodiment, the molecule is a peptide comprising an amino acid sequence of a fragment of αPKC (SEQ ID No 4). Preferably, the molecule is a peptide comprising an amino acid sequence of a fragment of αPKC including one or several of the residues which are predicted to mediate the interaction with ALMS1, in particular one or several of the residues selected in the list consisting of F114, D116, C118, L121, N138, Q142, 1145, P148, G433, E545, S562, S566, F597, D601, W602, K604, E606, G620, T631, V664, and 1667.

The present invention also relates to a method for identifying molecules suitable for use for treating or delaying the progression or onset of diabetes mellitus, insulin resistance, diabetic retinopathy, diabetic neuropathy, diabetic nephropathy, insulin resistance, hyperglycemia, obesity, and hyperinsulinaemia, wherein the capacity of the molecule to prevent the binding of αPKC to ALMS1 is assayed and the molecules capable of preventing this binding are selected. The method may additional comprises a step in which the capacity of the selected molecule to interfere with the binding of TBC1D4 to ALMS1 is tested and wherein the molecules which do not interfere are selected. Preferably, the binding is determined in a cellular system responsive to insulin. Optionally, the binding is determined in presence and/or absence of insulin.

A further therapeutic strategy revealed in this invention is to enhance cellular glucose absorption by enhancing the binding of TBC1D4 on ALMS1. A further therapeutic strategy revealed in this invention is to enhance cellular glucose absorption by upregulating expression of ALMS1.

Accordingly, the present invention further relates to a molecule capable of enhancing the binding of TBC1D4 on ALMS1 or increasing the expression of ALMS1 for use in treating or delaying the progression or onset of diabetes mellitus, insulin resistance, diabetic retinopathy, diabetic neuropathy, diabetic nephropathy, insulin resistance, hyperglycemia, obesity, and hyperinsulinaemia, in particular Type 2 diabetes. It also relates to the use of such a molecule for the manufacture of a medicament for treating or delaying the progression or onset of diabetes mellitus, insulin resistance, diabetic retinopathy, diabetic neuropathy, diabetic nephropathy, insulin resistance, hyperglycemia, obesity, and hyperinsulinaemia, in particular Type 2 diabetes. It also relates to a method for treating or delaying the progression or onset of diabetes mellitus, insulin resistance, diabetic retinopathy, diabetic neuropathy, diabetic nephropathy, insulin resistance, hyperglycemia, obesity, and hyperinsulinaemia, in particular Type 2 diabetes, in a subject in need thereof, wherein a therapeutically effective amount of a molecule capable of enhancing the binding of TBC1D4 on ALMS1 or increasing the expression of ALMS1 is administered, thereby increasing the glucose absorption induced by insulin. In a preferred embodiment, the molecule also inhibits the binding of αPKC on ALMS1.

The present invention also relates to a method for identifying molecules suitable for use for treating diabetes, wherein the capacity of the molecule to increase the expression of ALMS1 is assayed and the molecules capable of upregulating ALMS1 are selected. It further relates to method for identifying molecules suitable for use for treating diabetes, wherein the capacity of the molecule to increase the binding of TBC1D4 to ALMS1 is assayed and the molecules capable of increasing this binding are selected. Optionally, the method further comprises determining the capacity of the molecule to prevent the binding of αPKC to ALMS1 is assayed and selecting the molecules capable of preventing this binding

DETAILED DESCRIPTION OF THE INVENTION

The inventors identified ALMS1 as the missing key player involved in regulation the insulin-mediated glucose uptake through GLUT4 sorting vesicles into adipocytes.

It has been now acknowledged that, even if adipose tissue is responsible of about 20% of the glucose absorption, a dysfunction in this tissue can lead to diabetes occurrence. Therefore, any means capable of regulating the insulin-mediated glucose uptake into adipocytes should be able to delay, reverse, or prevent the occurrence of diabetes mellitus, insulin resistance, diabetic retinopathy, diabetic neuropathy, diabetic nephropathy, insulin resistance, hyperglycemia, obesity, and hyperinsulinaemia.

ALMS1 activity is downregulated by the binding of αPKC whereas it is activated by the binding of TBC1D4. It has also be shown that the binding sites of these two proteins on ALMS1 are so close that the simultaneous binding of both proteins is not allowed due to steric hindrance. Therefore, this regulation mechanism is a new target for treating or delaying the progression or onset of diabetes mellitus, insulin resistance, diabetic retinopathy, diabetic neuropathy, diabetic nephropathy, insulin resistance, hyperglycemia, obesity, and hyperinsulinaemia and the inventors propose to use a molecule capable of preventing the binding of αPKC to ALMS1 for these therapeutic indications.

Definitions

ALMS1, Alstrom syndrome protein 1, is a protein encoded by the ALMS1 gene. Mutations in the ALMS1 gene have been found to be causative for Alström syndrome. It is described in several databases, namely UniProt ID No Q8TCU4; Gene ID No 7840, HGNG ID No 428. Reference sequences are disclosed in Genbank under NM_015120.4 for mRNA and NP_055935.4 for protein. The protein sequence of human ALMS1 is disclosed in SEQ ID No 1.

TBC1D4 (TBC1 domain family member 4), also currently called As160, is supposed to act as a GTPase-activating protein for RAB2A, RAB8A, RAB10 and RAB14. It is described in several databases, namely UniProt ID No O60343, Gene ID No 9882, HGNG ID No 19165. Reference sequences are disclosed in Genbank under NM_014832.3 for mRNA and NP_055647.2 for protein (for isoform 1, chosen as canonical sequences). The isoform 2, which differs from isoform by the missing of the amino acids in positions 678-740 and referenced in UniProt under No O60343-2, promotes insulin-induced glucose transporter SLC2A4/GLUT4 translocation at the plasma membrane, thus increasing glucose uptake. The protein sequence of human TBC1D4 (isoform 1) is disclosed in SEQ ID No 2. The protein sequence of human TBC1D4 (isoform 2) is disclosed in SEQ ID No 3.

Protein kinase C alpha type, also called αPKC, PKC-A or PKC-alpha, belongs to a family of serine- and threonine-specific protein kinases that can be activated by calcium and the second messenger diacylglycerol. It is described in several databases, namely UniProt ID No P17252, Gene ID No 9393, HGNG ID No 5578. Reference sequences are disclosed in Genbank under NM_02737.2 for mRNA and NP_002728.1 for protein. The protein sequence of human αPKC is disclosed in SEQ ID No 4.

Screening Methods

The present invention relates to an in vitro or ex vivo method for identifying, screening or selecting a molecule capable of preventing the binding of αPKC to ALMS1. The method comprises determining the effect of molecule(s) on the binding of αPKC to ALMS1, and selecting the molecule(s) if the binding of αPKC to ALMS1 is decreased or prevented. Preferably, the method further comprises determining the effect of molecule(s) on the binding of TBC1D4 to ALMS1, and eliminating the molecule(s) if the binding of TBC1D4 to ALMS1 is decreased or prevented. Optionally, the method may comprise a step of selecting the molecule(s) if the binding of TBC1D4 to ALMS1 is increased or enhanced.

The present invention also relates to an in vitro or ex vivo method for identifying, screening or selecting a molecule capable of enhancing or increasing the binding of TBC1D4 to ALMS1. The method comprises determining the effect of molecule(s) on the binding of TBC1D4 to ALMS1, and selecting the molecule(s) if the binding of TBC1D4 to ALMS1 is increased or enhanced. Optionally, the method further comprises determining the effect of molecule(s) on the binding of αPKC to ALMS1, and selecting the molecule(s) if the binding of αPKC to ALMS1 is decreased or prevented.

In order to determine the effect of a molecule on the binding of αPKC and/or TBC1D4 to ALMS1, any technology known by the person skilled in the art can be carried out, in particular any method suitable for determining protein interactions. For example, recombinant or purified native ALMS1 or αPKC can be bound to a surface plasmon resonance ship and the other molecule flowed over the chip to assess the binding affinity, for example in a Biacore (General Electric, USA) machine. The same approach can be used to measure the binding affinity of ALMS1 and TBC1D4 or of ALMS1 and αPKC.

The effect of molecule(s) on the binding of αPKC and/or TBC1D4 to ALMS1 is determining by measuring the binding of αPKC and/or TBC1D4 to ALMS1 in absence and in presence of the tested molecule and by comparing the bindings of αPKC and/or TBC1D4 to ALMS1.

In addition, the screening method may comprise a preliminary step for selecting the molecule(s) capable of binding to ALMS1. Indeed, it could be advantageous that the molecule preventing the interaction between ALMS1 and αPKC acts directly on the ALMS1 binding site for αPKC. Alternatively, the screening method may comprise a preliminary step for selecting the molecule(s) capable to bind to αPKC. Indeed, it could also be advantageous that the molecule preventing the interaction between ALMS1 and αPKC acts directly on the αPKC binding site for ALMS1.

In addition, the screening method may comprise a preliminary step for selecting the molecule(s) capable to bind to TBC1D4.

In a preferred embodiment for identifying, screening or selecting a molecule capable of preventing the binding of αPKC to ALMS1, the screening method of the present invention further comprises determining the effect of the molecule(s), in particular the selected molecule(s), on the binding of TBC1D4 to ALMS1 and selecting the molecule(s) if the binding of TBC1D4 to ALMS1 is not decreased or prevented by the molecule(s). Even more, the method may comprise a step of selecting the molecule(s) if TBC1D4 to ALMS1 is increased or enhanced by the molecule(s).

In a preferred embodiment for identifying, screening or selecting a molecule capable of enhancing the binding of TBC1D4 to ALMS1, the screening method of the present invention further comprises determining the effect of the molecule(s), in particular the selected molecule(s), on the binding of αPKC to ALMS1 and selecting the molecule(s) if the binding of αPKC to ALMS1 is decreased or prevented by the molecule(s).

Due to the large size of the binding partners, in particular ALMS1 and TBC1D4, the inventors prefer using cellular systems for the screening methods. Preferably, the cellular system is a cellular system responsive to insulin. For instance, the cellular system could be selected among a mesenchymal cell line, a mesenchymal stem cell, an adipose mesenchymal stem cell, a pre-adipocyte and an adipocyte. Preferably, the cell is a human cell.

Then, the binding determinations can be carried in absence or presence of insulin, preferably in presence of insulin for the binding of αPKC to ALMS1 and in the presence insulin for the binding of TBC1D4 to ALMS1.

In a first aspect, immunoprecipitation assay using ALMS1 as bait can be carried, in particular as detailed in the experimental section. For instance, the assay can be carried out with cells, in particular adipocytes, cultured in absence and/or presence of insulin, preferably in absence of insulin. The molecules to be tested are added in the culture medium. Then, αPKC is immunodetected. Optionally, TBC1D4 can also be immunodetected. This method is disclosed in details in the Examples section.

In a preferred embodiment, the amount of αPKC bound to ALMS1 is determined and compared to the amount in absence of tested molecules, in particular in absence of insulin. If the amount of αPKC bound to ALMS1 decreases in presence of the tested molecule, then the molecule is selected.

The amount of TBC1D4 bound to ALMS1 is determined and compared to the amount in absence of tested molecules, in particular in presence of insulin or both in presence and absence of insulin. If the amount of TBC1D4 bound to ALMS1 decreases in presence of the tested molecule, then the molecule is rejected. If the amount of TBC1D4 bound to ALMS1 increases in presence of the tested molecule, then the molecule is selected.

In a second aspect, affinity purification coupled to mass spectrometry can be carried out, in particular after chemical crosslinking. For instance, cells may be cultured in a medium devoid of methionine and leucine but comprising photo-activable methionine and leucine. Then, cells are UV irradiated in order to stabilize protein complexes and protein complexes are analyzed by mass spectrometry.

Other methods are available to the person skilled in the art, e.g., Bimolecular fluorescence complementation, Tandem affinity purification, and the like. In particular, WO2012/117245 discloses a method for identifying molecules capable of preventing the interaction between two proteins: WO2012/117245 (i.e., for identifying small molecules). WO12174489 also discloses methods for developing molecules suitable for preventing interaction between two proteins.

In addition, suitable molecules can also be designed by molecular modelling. Such methods are for instance detailed in the Example section.

In a particular aspect, the present invention relates to a structural homology model of ALMS1 and its use in an in silico method to identify molecules able to inhibit or stimulate ALMSome function, in particular to inhibit the interaction between ALMS1 and αPKC and/or to increase the interaction between ALMS1 and TBC1D4.

It also relates to a structural homology model of TBC1D4 and its use in an in silico method to identify molecules able to inhibit or stimulate ALMSome function, in particular to increase the interaction between ALMS1 and TBC1D4.

The present invention also relates to a method for identifying, screening or selecting a molecule capable of upregulating ALMS1 at the gene and protein level. The method comprises determining the effect of molecule(s) on the expression of ALMS1, and selecting the molecule(s) if the expression of ALMS1 is increased. In order to determine the effect of a molecule on the expression of ALMS1, any technology known by the person skilled in the art can be carried out. Various techniques known in the art may be used to detect or quantify ALMS1 expression, including sequencing, hybridisation, amplification and/or binding to specific ligands (such as antibodies). Suitable methods include Southern blot (for DNAs), Northern blot (for RNAs), fluorescent in situ hybridization (FISH), gel migration, ELISA, radio-immunoassays (RIA) and immuno-enzymatic assays (IEMA).

By "increased", "increase" or "enhance" is intended to refer to a binding increased by at least 10, 20, 30, 40, 50, 60, 70, 80 or 90% when compared to the binding measured in absence of the tested molecule in the same conditions. By "decreased" or "decrease" is intended to refer to a binding decreased by at least 10, 20, 30, 40, 50, 60, 70, 80 or 90% when compared to the binding measured in absence of the tested molecule in the same conditions.

In addition, the screening methods of the present invention may comprise assay with animal models. Molecules to be tested may be administered to the animal models and the effect of the molecules on the glucose absorption or diabetes could be assessed. For instance, the animal models could be mice or rat with insulin resistance, diabetes, or hyperglycemia. The effect of the molecule can be assessed by measuring the level of blood glucose.

Molecules

The molecules capable of preventing or blocking the binding of αPKC to ALMS1 can be any ligand capable of binding either αPKC or ALMS1 and, thereby preventing or blocking the binding of αPKC to ALMS1.

In a first aspect, the present invention relates to a molecule that prevents or blocks the binding of αPKC to ALMS1 by interacting with one or more of the ALMS1 residues selected in the list consisting of E17, D58, S59, G62, H65, L66, Q736, T737, E738, D828, 5829, T1088, D1089, A1169, Q1170, F2882, L2883, and E2884. In an alternative aspect, the present invention relates to a molecule that prevents or blocks the binding of αPKC to ALMS1 by interacting with one or more of the αPKC residues selected in the list consisting of F114, D116, C118, L121, N138, Q142, 1145, P148, G433, E545, 5562, 5566, F597, D601, W602, K604, E606, G620, T631, V664, and 1667.

The molecules capable of enhancing or increasing the binding of TBC1D4 to ALMS1 can be any ligand capable of binding either TBC1D4 or ALMS1 and, thereby enhancing or increasing the binding of TBC1D4 to ALMS1.

In a first aspect, the present invention relates to a molecule that enhances or increases the binding of TBC1D4 to ALMS1 by interacting with one or more of the ALMS1 residues selected in the list consisting of H65, L66 and 52879. In an alternative aspect, the present invention relates to a molecule that enhances or increases the binding of TBC1D4 to ALMS1 by interacting with one or more of the TBC1D4 residues selected in the list consisting of G75, A76, P77, A78, R80, E81, V82, and 183.

The present invention relates to such molecules, a pharmaceutical composition comprising such molecules, and the use of such molecules as a drug or for the manufacture of a drug.

The molecules can be peptides or polypeptides or peptide mimetics, antibodies, fragments or derivatives thereof, aptamers, Spiegelmers, or chemical compounds. The molecules can be selected by the screening methods known in the art or as detailed above and can be designed by any convenient in silico modeling method.

In a preferred embodiment, the molecule is a peptide or polypeptide. Preferably, the peptide may have between 5 and 50 amino acids. More preferably, it has between 5 and 20 amino acids. More preferably, the peptide or polypeptide comprises less than 50 amino acids, more preferably less than 40, 30, 20, 15 or 10 amino acids.

In a first aspect, the molecule is a peptide or polypeptide comprising an amino acid sequence of a fragment of ALMS1 (SEQ ID No 1). In a preferred embodiment, the molecule is a peptide or polypeptide comprising an amino acid sequence of a fragment of ALMS1 including one or several of the residues which are predicted to mediate the interaction with αPKC. In particular, these residues are selected in the list consisting of E17, D58, S59, G62, H65, L66, Q736, T737, E738, D828, 5829, T1088, D1089, A1169, Q1170, F2882, L2883, and E2884. More preferably, these residues are selected in the list consisting of D58, S59, G62, H65, L66, Q736, T737, E738, D828, S829, T1088, D1089, A1169, Q1170, F2882, L2883, and E2884. D58, S59, G62, H65 and L66 define a first interaction segment. T737 and E738 define a second interaction segment. D828 and S829 define a third interaction segment. T1088 and D1089 define a fourth interaction segment. A1169 and Q1170 define a fifth interaction segment. F2882, L2883 and E2884 define a sixth interaction segment.

In a very particular aspect, the peptide or polypeptide comprises or consists of one of the following sequences:
LDSDSHYGPQHLESIDD (SEQ ID No 5), targeting the first interaction segment;

DSHQTEETL (SEQ ID No 6), targeting the second interaction segment;
QQTLPESHLP (SEQ ID No 7);
QALLDSHLPE (SEQ ID No 8), targeting the third interaction segment;
PADQMTDTP (SEQ ID No 9), targeting the fourth interaction segment;
HIPEEAQKVSAV (SEQ ID No 10), targeting the fifth interaction segment;
SCIFLEQ (SEQ ID No 11), targeting the sixth interaction segment, and
a fragment thereof comprising 6 contiguous amino acids.

In a second aspect, the molecule is a peptide or polypeptide comprising an amino acid sequence of a fragment of αPKC (SEQ ID No 4). In a preferred embodiment, the molecule is a peptide or polypeptide comprising an amino acid sequence of a fragment of αPKC including one or several of the residues which are predicted to mediate the interaction with ALMS1. In particular, these residues are selected in the list consisting of F114, D116, C118, L121, N138, Q142, 1145, P148, G433, E545, 5562, 5566, F597, D601, W602, K604, E606, G620, T631, V664, and 1667. F114, D116, C118 and L121 may define a first interaction segment. N138, Q142, 1145 and P148 may define a second interaction segment. E545, S562 and S566 may define a third interaction segment. F597, D601, W602, K604, and E606 define a fourth interaction segment. V664 and I667 may define a fifth interaction segment.

Optionally, the peptide or polypeptide may comprise one, two, three, four or five amino acid substitution in comparison to the reference sequence, i.e., SEQ ID No 1 for peptides derived from ALMS1, SEQ ID No 4 for peptides derived from αPKC, and SEQ ID No 2 or 3 for peptides derived from TBC1D4.

The peptide or polypeptide may further comprise a moiety facilitating its cellular uptake or entry, in particular a PTD (protein transduction domain). PTD generally comprises a certain amino acid 10 sequence of 10 to 20 amino acids (Matsushita and Matsui, (2005), J Mol Med 83, 324-328; Vives et al, Biochimic et Biophysica Acta, 2008, 1786, 126-138). PTD is mainly composed of basic amino acids such as arginine or lysine, and representative examples of the PTD include arginine rich peptides such as poly Rs (RRRRRRRR) (SEQ ID NO: 18) or (RRPRRPRRPRRPRRP) (SEQ ID NO: 19), antennapedia or penetratin peptide such as (RQIKIWFQNRRMKWKK) (SEQ ID NO: 20) or HIV-Tat (YGRKKRRQRRR) (SEQ ID NO: 21).

In a particular aspect, the molecule is an antibody, fragment or derivative thereof.

The peptide or polypeptide can be made of natural amino acids and/or unnatural amino acids. By "unnatural amino acids" is intended an analog or derivative of a natural amino acid (i.e., Ala, Val, Gly, Leu, Ile, Lys, Arg, Glu, GLn, Asp, Asn, His, Tyr, Phe, Trp, Ser, Pro, Thr, Cys, Met). They present a modified side chain, e.g. shorter, longer or with different functional groups. Isomers D and L are contemplated, in particular because isomers D are not sensible to proteases. In addition, modifications in some or all peptide bounds are also contemplated in order to increase the proteolysis resistance, in particular by (—CO—NH—) by (—CH$_2$—NH—), (—NH—CO—), (—CH$_2$—O—), (—CH$_2$—S—), (—CH$_2$—CH$_2$—), (—CO—CH$_2$—), (—CHOH—CH$_2$—), (—N═N—), and/or (—CH═CH—). The peptide can present a carboxylic C terminal end (—COO—) and an amide one (—CONH$_2$). The peptide can also be D-retro-inverso sequence of a peptide as disclosed herein. The N terminal can be modified, especially with an acetyl radical. Optionally, the peptide or polypeptide can be PEGylated in order to increase the stability. Alternatively, the peptide can be modified to become a stapled peptide. The term "stapled peptide" as used herein refers to artificially modified peptide in which the structure is stabilized with one or more artificial molecular bridging (cross links) that connects adjacent turns of α-helices in the peptide. The modalities for preparing stapled peptides have been reviewed extensively for instance in Verdine & Hilinski (2012, Methods Enzymol, 503, 3-33), WO10033617 and WO10011313, the disclosure of which being incorporated herein by reference).

The present invention further relates to a pharmaceutical composition comprising a peptide as defined above and a pharmaceutically acceptable carrier/excipient. It also relates to a peptide as defined above for use as a drug or to the use of a peptide as defined above for the manufacture of a medicament.

In an alternative embodiment, the molecule is an antibody, a fragment thereof or a derivative thereof. As used herein, the terms "antibody" and "immunoglobulin" have the same meaning and are used indifferently in the present invention. The term "antibody" refers to immunoglobulin molecules and immunologically active portions of immunoglobulin molecules, i.e., molecules that contain an antigen-binding site that immunospecifically binds an antigen. Antibodies include any kind of antibodies, preferably monoclonal. They can be for instance IgG (immunoglobulin G) or VHH (heavy chain variable domain antibody from camelids). Antibodies fragments or derivatives thereof include Fab, Fab', F(ab')2, scFv, (scFv)2, dAb, complementarity determining region (CDR) fragments, linear antibodies, single-chain antibody molecules, minibodies, diabodies, and multispecific antibodies formed from antibody fragments.

Antibodies, fragments or derivatives can block the interaction between ALMS1 and αPKC. Preferably, they have no effect on the interaction between ALMS1 and TBC1D4 or have an enhancing effect on the interaction.

In a first embodiment, the antibody is specific for ALMS1. In particular, the epitope of the antibody comprises one or several of the ALMS1 residues involved in the interaction with αPKC, in particular one or several residues selected in the list consisting of E17, D58, S59, G62, H65, L66, Q736, T737, E738, D828, 5829, T1088, D1089, A1169, Q1170, F2882, L2883, and E2884.

Alternatively, the antibody is specific for αPKC. In particular, the epitope of the antibody comprises one or several of the αPKC residues involved in the interaction with ALMS1, in particular one or several residues selected in the list consisting of F114, D116, C118, L121, N138, Q142, 1145, P148, G433, E545, 5562, 5566, F597, D601, W602, K604, E606, G620, T631, V664, and 1667.

Such antibodies can be produced by immunizing non-human mammals with immunogenic peptides or proteins comprising one or several residues identified as involved in the interaction between ALMS1 and αPKC. Alternatively, library of antibodies can be provided and screened. Produced antibodies, fragments or derivatives are then screened for their capacity to bind one of the interacting partners and/or their capacity to prevent, inhibit or block the interaction between ALMS1 and αPKC. In addition, as previously specified, antibodies, fragments or derivatives can be further screened for their capacity to modulate the interaction between TBC1D4 and ALMS1, and selected if they increase or enhance the interaction.

Antibodies, fragments or derivatives can enhance the interaction between ALMS1 and TBC1D4. Preferably, they have a blocking effect on the interaction between ALMS1 and αPKC.

In a first embodiment, the antibody is specific for ALMS1. In particular, the epitope of the antibody comprises one or several of the ALMS1 residues involved in the interaction with TBC1D4, in particular one or several residues selected in the list consisting of H65, L66 and S2879.

Alternatively, the antibody is specific for TBC1D4. In particular, the epitope of the antibody comprises one or several of the TBC1D4 residues involved in the interaction with ALMS1, in particular one or several residues selected in the list consisting of G75, A76, P77, A78, R80, E81, V82, and I83.

Such antibodies can be produced by immunizing non-human mammals with immunogenic peptides or proteins comprising one or several residues identified as involved in the interaction between ALMS1 and TBC1D4. Alternatively, library of antibodies can be provided and screened. Produced antibodies, fragments or derivatives are then screened for their capacity to bind one of the interacting partners and/or their capacity to enhance or increase the interaction between ALMS1 and TBC1D4. In addition, as previously specified, antibodies, fragments or derivatives can be further screened for their capacity to modulate the interaction between αPKC and ALMS1, and selected if they decrease or block the interaction.

The preparation of monoclonal or polyclonal antibodies is well known in the art, and any of a large number of available techniques can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy (1985)). Techniques for the production of single chain antibodies (U.S. Pat. No. 4,946,778) can be adapted to produce antibodies to desired polypeptides. Also, transgenic mice, or other organisms such as other mammals, may be used to express humanized, chimeric, or similarly-modified antibodies. Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)).

For aptamers and Spiegelmers, similar methods can be used in order to select aptamers and Spiegelmers. These methods are well-known by the person skilled in the art.

As used here, the term "aptamer" means a molecule of nucleic acid or a peptide able to bind ALMS1, αPKC or TBC1D4. It refers to a class of molecule that represents an alternative to antibodies in term of molecular recognition. Aptamers are oligonucleotide or oligopeptide sequences with the capacity to recognize virtually any class of target molecules with high affinity and specificity.

Such ligands may be isolated through Systematic Evolution of Ligands by EXponential enrichment (SELEX) of a random sequence library, as described in Tuerk C. and Gold L., Science, 1990, 249(4968):505-10. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., Clin. Chem., 1999, 45(9):1628-50. Peptide aptamers consist of a conformationally constrained antibody variable region displayed by a platform protein, such as E. coli Thioredoxin A that are selected from combinatorial libraries by two hybrid methods (Colas et al., Nature, 1996, 380, 548-50).

Spiegelmers have been disclosed for instance in WO 98/08856. They are molecules similar to aptamers. However, spiegelmers consist either completely or mostly of L-nucleotides rather than D-nucleotides in contrast to aptamers. Otherwise, particularly with regard to possible lengths of spiegelmers, the same applies to spiegelmers as outlined in connection with aptamers.

Chemical compounds refers to a molecule of less than about 1500 Daltons, 1000 Daltons, 800 Daltons, or even less than about 500 Daltons, in particular organic or inorganic compounds. Structural design in chemistry should help to find such a molecule. The molecule may have been identified by a screening method disclosed in the present invention.

Synthetic compound libraries are commercially available from a number of companies including Maybridge Chemical Co. (Trevillet, Cornwall, UK), Comgenex (Princeton, N. J.), Brandon Associates (Merrimack, N.H.), and Microsource (New Milford, Conn.). Combinatorial libraries are available or can be prepared according to known synthetic techniques. Alternatively, libraries of natural compounds in the form of bacterial, fungal, plant and animal extracts are available from e.g., Pan Laboratories (Bothell, Wash.) and MycoSearch (NC), or are readily producible by methods well known in the art.

Additionally, natural and synthetically produced libraries and compounds can be further modified through conventional chemical and biochemical techniques.

The molecule can be linked, covalently or not, to a moiety targeting the relevant tissues, preferably the adipose or to a moiety facilitating the entrance of the molecule into cells.

Therapeutic Indications

The inventors propose to use the molecules as disclosed herein for increasing the glucose uptake, in particular by adipocytes, thereby regulating or controlling the blood glucose level. Then, the molecules are suitable for treating or delaying the progression or onset of diabetes mellitus, insulin resistance, diabetic retinopathy, diabetic neuropathy, diabetic nephropathy, insulin resistance, hyperglycemia, obesity, and hyperinsulinaemia.

Diabetes mellitus is characterized by hyperglycemia. More particularly, type 2 diabetes is characterized by hyperglycemia and insulin resistance. Obesity is thought to be the primary cause of type 2 diabetes in people who are genetically predisposed to the disease. Diabetic retinopathy, diabetic neuropathy, diabetic nephropathy are well-known disorders associated with diabetes and insulin resistance.

Then, decreasing the glycemia by increasing the glucose uptake could treat or delay the progression or onset of these diseases.

The present invention also relates to the molecules according to the invention for use for reducing the dose of insulin or stopping the insulin treatment when used for treating diabetes in a subject, to the use of the molecules according to the invention for the manufacture of a medicament for reducing the dose of insulin or stopping the insulin treatment when used for treating diabetes in a subject, or to a method for treating diabetes in a subject, wherein a therapeutically effective amount of a molecule according to the invention is administered to a subject with a decreased dose of insulin or in absence of insulin treatment. More generally, it can be use to lower the doses of anti-diabetic drugs.

By "treat" or "treatment" is intended that the disease is cured, alleviated or delayed. It includes the preventive or curative treatment. The term treatment designates in particular the correction, retardation, or reduction of an impaired glucose homeostasis. The term "treatment" also designates an improvement in glucose uptake (e.g., capture of glucose by adipocytes). Within the context of the invention, the terms "controlling the blood glucose level" or "the control of blood glucose level" refer to the normalization or the regulation of the blood or plasma glucose level in a mammalian subject having abnormal levels (i.e., levels that are below or above a known reference, median, or average value for a corresponding mammalian subject with a normal glucose homeostasis).

The present invention relates to the pharmaceutical or veterinary use of the molecule. Accordingly, the subject may be any mammal, preferably a human subject, such as an adult or a children. In a particular embodiment, the subject is a subject suffering of obesity. Optionally, the subject has no detectable anti-islet antibodies, and ultrasonography revealed no pancreatic abnormalities. In the context of a veterinary application, the subject can be an animal, preferably a mammal, in particular a pet animal such as a dog, a cat or a horse.

The molecules according to the invention can be used in combination with one or more additional active drugs, preferably anti-diabetic drugs, in particular for treating or delaying the progression or onset of diabetes mellitus, insulin resistance, diabetic retinopathy, diabetic neuropathy, diabetic nephropathy, insulin resistance, hyperglycemia, obesity, and hyperinsulinaemia.

Therefore, the present invention also relates to a pharmaceutical composition comprising a molecule according to the present invention and one or more additional active drugs, preferably an anti-diabetic drug.

It further relates to a product or kit containing a molecule according to the invention and one or more additional active drugs, preferably anti-diabetic drugs, as a combined preparation for simultaneous, separate or sequential use, or a combined preparation which comprises a molecule according to the invention and one or more additional active drugs, preferably anti-diabetic drugs, for simultaneous, separate or sequential use, in particular for treating or delaying the progression or onset of diabetes mellitus, insulin resistance, diabetic retinopathy, diabetic neuropathy, diabetic nephropathy, insulin resistance, hyperglycemia, obesity, and hyperinsulinaemia.

It relates to a molecule according to the invention for use for treating or delaying the progression or onset of diabetes mellitus, insulin resistance, diabetic retinopathy, diabetic neuropathy, diabetic nephropathy, insulin resistance, hyperglycemia, obesity, and hyperinsulinaemia in combination with one or more additional active drugs, preferably anti-diabetic drugs.

It further relates to the use of a molecule according to the invention and one or more additional active drugs, preferably anti-diabetic drugs, for the manufacture of a medicament, in particular treating or delaying the progression or onset of diabetes mellitus, insulin resistance, diabetic retinopathy, diabetic neuropathy, diabetic nephropathy, insulin resistance, hyperglycemia, obesity, and hyperinsulinaemia.

Finally, it relates a method for treating or delaying the progression or onset of diabetes mellitus, insulin resistance, diabetic retinopathy, diabetic neuropathy, diabetic nephropathy, insulin resistance, hyperglycemia, obesity, and hyperinsulinaemia, wherein a therapeutic effective amount of a molecule according to the invention is administered in combination with a therapeutic or sub-therapeutic effective amount of one or more additional active drugs, preferably anti-diabetic drugs. By "sub-therapeutic" is intended to refer to an amount can be for instance 90, 80, 70, 60, 50, 40, 30, 20 or 10% of the conventional therapeutic dosage (in particular for the same indication and the same administration route).

In particular, the additional active drug is a drug used for treating or delaying the progression or onset of diabetes mellitus, insulin resistance, diabetic retinopathy, diabetic neuropathy, diabetic nephropathy, insulin resistance, hyperglycemia, obesity, and hyperinsulinaemia. For instance, the additional drug can be an anti-diabetic drug such as a hypoglycemic agent or an antihyperglycemic agent. It may be selected in the non-exhaustive list comprising insulin, metformin, sulfonylureas such as tolbutamide, acetohexamide, tolazamide, chlorpropamide, glyburide (also called glibenclamide), glimepiride, glipizide, glicazide, glycopyramide and gliquidone, alpha-glucosidase inhibitors such as acarbose, miglitol and voglibose, thiazolidinediones such as pioglitazone and rosiglitazone, a meglitinide such as repaglinide and nateglinide, incretin mimetics, glucagon-like peptide analogs and agonists such as exenotide, taspoglutide and liraglutide, dipeptidyl peptidase-4 inhibitors such as vildagliptin, sitagliptin, saxagliptin, linagliptin, allogliptin, and septagliptin, amylin analogs such as pamlintide, glycourics such as canagliflozin and dapagliflozin, or any combination thereof.

The form of the pharmaceutical compositions, the route of administration, the dosage and the regimen naturally depend upon the condition to be treated, the severity of the illness, the age, weight, and sex of the patient, etc.

The pharmaceutical or therapeutic compositions of the invention can be formulated for a topical, oral, parenteral, intranasal, intravenous, intramuscular, subcutaneous or intraocular administration and the like.

The molecule used in the pharmaceutical composition of the invention is present in a therapeutically effective amount. The term "therapeutically effective amount" as used in the present application is intended an amount of therapeutic agent, administered to a patient that is sufficient to constitute a treatment of diabetes mellitus, insulin resistance, diabetic retinopathy, diabetic neuropathy, diabetic nephropathy, insulin resistance, hyperglycemia, obesity, and hyperinsulinaemia as defined above.

The pharmaceutical composition comprising the molecule is formulated in accordance with standard pharmaceutical practice (Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art.

For oral administration, the composition can be formulated into conventional oral dosage forms such as tablets, capsules, powders, granules and liquid preparations such as syrups, elixirs, and concentrated drops. Non toxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials, are also necessary. For example, starch, gelatine, sugars such as lactose or dextrose, and natural or synthetic gums can be used as binders. Disintegrants are also necessary in the tablets to facilitate break-up of the tablet. Disintegrants include starches, clays, celluloses, algins, gums and crosslinked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

For transdermal administration, the composition can be formulated into ointment, cream or gel form and appropriate penetrants or detergents could be used to facilitate permeation, such as dimethyl sulfoxide, dimethyl acetamide and dimethylformamide.

For transmucosal administration, nasal sprays, rectal or vaginal suppositories can be used. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate.

Pharmaceutical compositions according to the invention may be formulated to release the active drug substantially immediately upon administration or at any predetermined time or time period after administration.

Pharmaceutical compositions according to the invention can comprise one or more molecule of the present invention associated with pharmaceutically acceptable excipients and/or carriers.

These excipients and/or carriers are chosen according to the form of administration as described above.

In a particular embodiment, the pharmaceutical composition according to the invention comprises 0.001 mg to 10 g of the molecule of the invention. Preferably, pharmaceutical composition according to the invention comprises 0.01 mg to 1 g of the molecule of the invention.

BRIEF DESCRIPTION OF THE DRAWINGS

FIG. 4. ALMS1 is required for TBC1D4 cellular trafficking (A) In silico predicted 3D structure showing spatial interaction between ALMS1 and TBC1D4 with an enlarged view of the interaction site highlighting the predicted interacting amino acids residues (L66, Y61 and 52879) of the ALMS1 protein. (B) 3D image from immunostained mature adipocytes depicting co-localization of TBC1D4 (green) and ALMS1 (red). Nuclei were counterstained with DAPI (blue). (C-D) Immunoblots for the indicated proteins on cell lysates (50 µg total protein loaded per lane) for CTRLshRNA and ALMS1shRNA mature adipocytes treated with or without insulin. 3D images of immunofluorescence experiments performed on either CTRLshRNA or ALMS1 shRNA or TBC1D4shRNA mature adipocytes depicting cellular localization of GLUT4 in absence of Insulin (-INS) (E) or in the presence of INS. (F). PM: Plasma membrane and nuclei counterstained with DAPI. 3D images of immunofluorescence experiments performed on either CTRLshRNA or ALMS adipocytes showing cellular localization of GLUT4 (green) and TBC1D4 in absence of INS (G) or when treated 30 min. with INS. (H). Scale bars: 10 µm.

FIG. 5. TBC1D4 is not the sole interacting partner of ALMS1 playing a role in the adipocyte biology (A-C) Photographs showing absorption of 2-NBDG in either CTRLshRNA or ALMS1shRNA or TBC1D4shRNA deprived adipocytes after 30 min Ins. stimulation. (D-F) 3D images obtained using non-permeablized fixated mature adipocytes stimulated with INS. following immunodetection of GLUT4 membrane bound (green). Plasma membrane (PM) was stained with Image-iT (red) and nuclei were counterstained with DAPI. (G) Immunoblots of 2 proton pumps subunits (ATP6V0D1 and ATP6V1A) identified by mass spectrometry in the IP experiments using ALMS1 as bait (FIG. S4), αPKC, GLUT4 and β-Tubulin in cellular extracts from white adipose tissue (WAT) and kidney. 50 µg total protein loaded per lane. (H) Photograph of Duolink positive signal detected in adipocytes using antibodies against ALMS1 and ATP6. (I) Immunofluorescence pictures showing cellular localizations of ATP6V0D1 and ALMS1 and merged in mature adipocytes upon INS. stimulation. (J) In silico predicted binding sites of TBC1D4 (red) and PKC (yellow) which are only 20 Angstroms away from each other in the ALMS1 3D structure. (K-L) Immunodetections of αPKC, TBC1D4 and α-Actinin in immunoprecipitates using ALMS1 as bait in adipocytes cultured in absence or presence of INS.

FIG. 7. GLUT4 trafficking requires ALMSome protein complex (A) 3D images obtained using non-permeablized fixated mature adipocytes stimulated with NIG. following immunodetection of GLUT4 membrane bound (green). Plasma membrane (PM) was stained with Image-iT (red) and nuclei were counterstained with DAPI. (B) Photographs showing intracellular TG content 24 hrs. after NIG. treatment. (C) Schematic representation of ALMS1 cellular localization and protein partner in absence of INS. stimulation in mature adipocyte. (D) Schematic representation of ALMS1 dynamics and protein partners after INS. stimulation in mature adipocyte.

Figure 1:
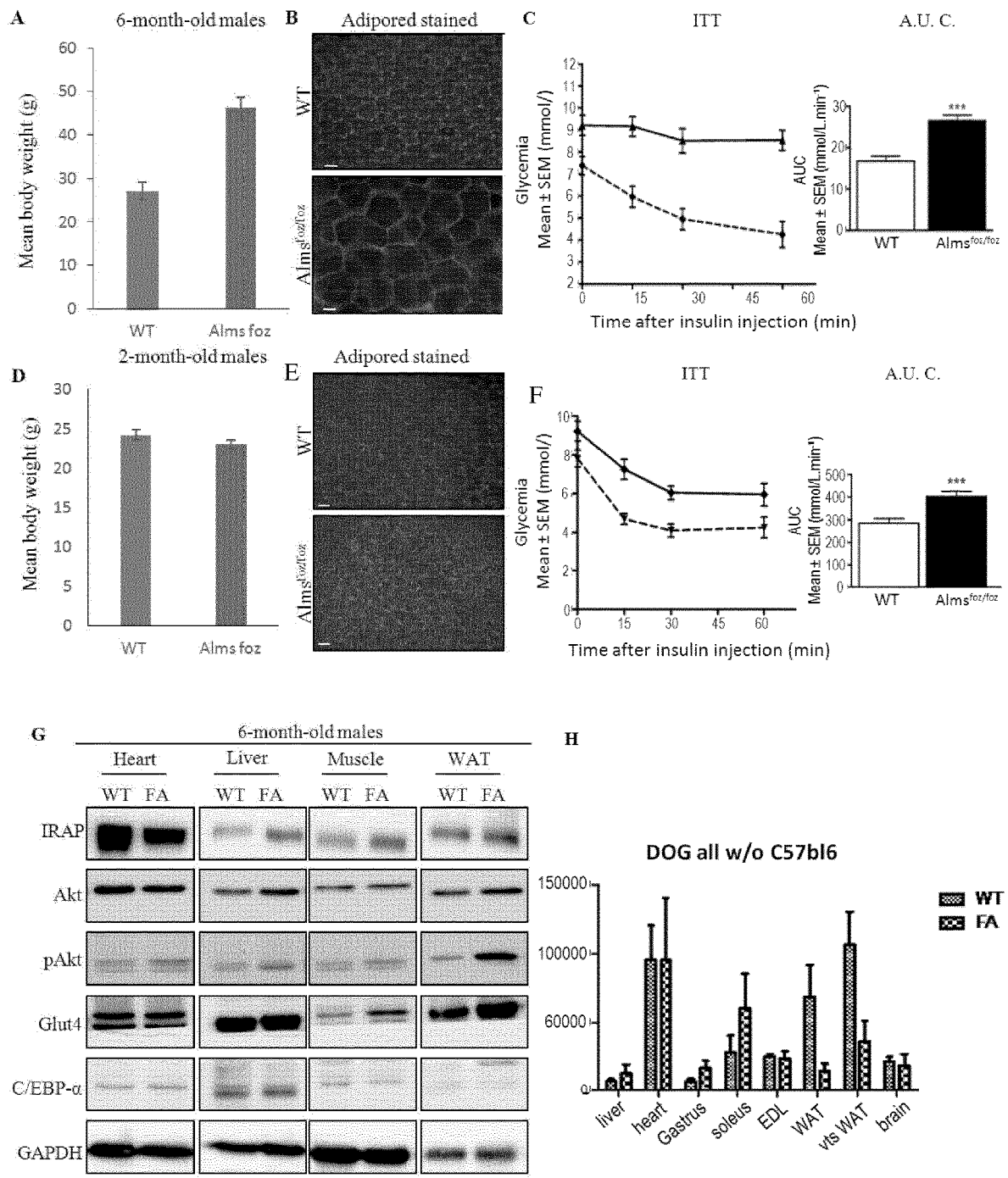
FIG. 1. Metabolic characterization of the Alms$^{foz/foz}$ mice (A) Mean body weight of WT and Alms$^{foz/foz}$ male mice (n=6-8 mice per genotype). (B) Photograph of visceral adipose tissue from WT and Alms$^{foz/foz}$. Scale bar: 25 µM. (C) Insulin tolerance test (I.T.T.) performed on WT and Alms$^{foz/foz}$ mice and the corresponding histogram showing the Area under the curve (A.U.C.) for each genotype (n=6-8 mice per group). p<0.001). (D) Mean body weight of WT and Alms$^{foz/foz}$ male mice (n=6-8 mice per genotype). (E) Photograph of visceral adipose tissue from corresponding WT and Alms$^{foz/foz}$ Scale bar: 25 µM. (F) Insulin tolerance test performed on WT and Alms$^{foz/foz}$ mice and the corresponding histogram showing the A.U.C. for each genotype (n=6-8 mice per group). *** stands for p-value<0.001. (G) Immunoblots for the indicated proteins in insulin sensitive tissues from non-obese WT and Alms$^{foz/foz}$ mice. (H) Results of radioactive counts in different target tissues after injection of radioactive deoxyglucose to WT and Alms$^{foz/foz}$ mice (n=5 mice per genotype). * stands for p-value=0.05.

Top panel: Immunodetection of min-αPKC-FLAG using an anti-FLAG antibody in mature adipocytes 48 hours post lentiviral infection. $2^{nd}$ and $3^{rd}$ panels: 3D image of the adipocyte showing the perinuclear localization of min-αPKC-FLAG. Last panel: Schematic representation of the experimental approaches used to assess the effect of min-αPKC-FLAG on glucose absorption.

EXAMPLES

Alström syndrome (ALMS) is a rare autosomal recessive disorder characterized by several clinical features including obesity and early-onset diabetes. It originates due to mutations in the ALMS1 gene coding for a protein of 460 kDa.

The function of the ALMS1 gene and how it causes the Alström syndrome phenotype has hitherto been unknown, with studies into its function being impeded by the extremely large size of the encoded protein and its low levels of expression.

Alström syndrome (ALMS) is a rare monogenic childhood obesity syndrome for which there is only one causative mutated gene identified to date, the ALMS1 gene. ALMS is classified as a member of the ciliopathy disorders that includes Bardet Biedl syndrome, a group of syndromic disorders originating from mutations in the large number of different proteins that together play a critical role in primary cilium function. Alms1 encodes the 461 kDa ALMS1 protein that was originally described to bear a purely centriolar localization, although more recent data has also suggested a cytoplasmic localization of ALMS1.

ALMS is clinically identified by collective multisystem phenotype thought to reflect the ubiquitous tissue expression of ALMS1, closely mimicking many of the phenotypic features of BBS. Common clinical features of ALMS include retinal degeneration, hearing loss, childhood obesity, early-onset type 2 diabetes mellitus (T2DM) dilated cardiomyopathy, renal and hepatic dysfunction, hypothyroidism, short stature, hyperlipidemia, and organ fibrosis. Children with ALMS develop obesity in early childhood that is associated with early onset of T2DM at around 16 years of age with a much higher overall prevalence of early onset T2DM in ALMS than seen with other childhood obesity syndromes resulting in a similar body mass index (BMI) including BBS. The reason for this predilection for T2DM in children with ALMS that is out of proportion to their degree of obesity has remained elusive.

The inventors investigated the role of the ALMS1 protein during the adipogenic differentiation process and found that the ALMS1 protein expression levels increased during adipogenesis. ALMS1 suppression, in adipogenic differentiating mesenchymal stem cells, inhibited the anti-adipogenic cascades but surprisingly was not favoring adipogenesis.

In addition, the inventors showed the ALMS1 protein complex is also required in mature adipocytes for efficient GLUT4 retention in its insulin-responsive compartment and its ability to fuse with the plasma membrane in response to insulin stimulation. Inactivation of ALMS1 decreased the amount of glucose able to be absorbed by mature adipocytes upon insulin stimulation, therefore contributing to hyperglycaemia and the onset of diabetes.

Previous studies in the spontaneous mutant $Alms^{foz/foz}$ and genetrapped Alms1 knockout murine ALMS models confirmed that these mice, similarly to affected human children, develop obesity in early adolescence due to hyperphagia, and also exhibit impaired glucose tolerance, hyperinsulinemia and islet hypetrophy, consistent with severe insulin resistance, although the tissue origin or mechanism for this insulin resistance has previously not been characterised. Previously published studies of in vitro studies on the murine 3T3-L1 fibroblast cell line showed that inhibition of ALMS1 gene expression resulted in mild impairment of adipogenesis but was reported to have no effect on the insulin signaling pathway in the resulting mature adipocytes as measured by insulin-mediated AKT phosphorylation. This data led directly away from the invention presented here that Alms1 does indeed play a critical hitherto unrecognized role in the insulin signaling pathway and in GLUT4 mediated glucose transport.

Indeed, despite the previously published contrary data, the inventors when carefully studying the phenotype of the Fat Aussie murine ALMS model ($Alms1^{foz/foz}$) identified that insulin resistance in this model preceded rather than followed the development of obesity. They further identified the adipose tissue as the specific site driving the insulin resistance and subsequent development of glucose intolerance and T2DM in ALMS. They confirmed that insulin signaling in Alms1$^{foz/foz}$ adipocytes was intact all the way down to phosphorylation of TBC1D4, the last known member of the insulin-mediated glucose uptake pathway but then through a subsequent series of investigations identified a protein complex they termed the Almsome, composed of several key proteins that associate with ALMS1 and which together are required for the tethering and fusion of the GLUT4 vesicles to the adipocyte plasma membrane (PM) in response to insulin signaling. The Almsome thereby represents the hitherto unidentified ultimate step in insulin-mediated glucose uptake into adipocytes, with insulin resistance in ALMS due to disruption of Almsome function leading to failure of GLUT4 membrane fusion and thereby a block to adipocyte glucose transport.

Example 1

Alms1$^{foz/foz}$ Mice Display Severe Specific Adipose Tissue Insulin Resistance Even in the Absence of Obesity Animal Husbandry Alms1 foz/foz mice and Alms1+/+ (WT) littermates were maintained on a C57BL/6J background in the animal facility on a 12 hourly light/dark cycle. Mice had free access ad libitum to water and either normal chow containing 5.4% fat, energy content 12 MJ/kg (Gordon's rat and mouse maintenance pellets, Gordon's specialty stockfeeds, Australia) or high fat diet (HFD) containing 23% Fat, High Simple carbohydrate, 0.19% cholesterol, energy content 20 MJ/kg (SF03-020, Specialty feeds, Australia). Primers flanking the foz mutation were used for PCR genotyping: forward ACA ACT TTT CAT GGC TCC AGT (SEQ ID NO: 12); reverse TTG GCT CAG AGA 15 CAG TTG AAA (SEQ ID No NO: 13).

Six month old obese and young (<60 days old) nonobese Alms1$^{foz/foz}$ mice and wildtype (WT) littermates were used to investigate what primary metabolic impairment leads Alms1$^{foz/foz}$ mice to develop T2DM. Six month old Alms$^{foz/foz}$ mice were obese with an average body weight of 45.5 g±1.7 g compared to 26.4 g±1.3 g for WT littermates (FIG. 1A) and as previously shown had fasting hyperglycaemia and impaired glucose tolerance with elevated HOMA scores. An insulin tolerance test (ITT) showed that unlike WT (FIG. 1B) and heterozygous littermates, glycaemia in obese Alms1foz$^{/foz}$ mice was unresponsive to insulin administration (FIG. 1B), even when doses of insulin as high as 20 U/kg were administered. (FIG. 1C). Obesity of Alms1$^{foz/foz}$ mice was due to severe adipocyte hypertrophy (FIG. 1B) rather than the adipocyte hyperplasia more typically seen in obese BBS mice. To determine what the primary defect was that was causing the glucose intolerance in Alms1$^{foz/foz}$ mice, young lean Alms1$^{foz/foz}$ mice were studied to remove the confounding effect of obesity on insulin responsiveness. At 2 months of age, WT and Alms1$^{foz/foz}$ males had a similar average body weight of ~24 g (FIG. 1D). ITT in these mice showed that nevertheless the young nonobese Alms1$^{foz/foz}$ males already exhibited significantly reduced insulin responsiveness (FIG. 1E), consistent with insulin resistance preceding obesity in this model. Immunodetection of RAP, Akt, p-AKT, GLUT4, C/EBP-α and GAPDH performed on insulin sensitive tissues namely, heart, liver, skeletal muscles and white adipose tissue (WAT) of 6-month-old non-fasted Alms1$^{foz/foz}$ and WT showed no major differences in protein levels except for a consistent increase in the p-AKT to total AKT ratio in WAT, consistent with a paradoxical increase rather than reduction in activation of upstream members of the insulin signaling pathway in glucose intolerant Alms1$^{foz/foz}$ mice (FIG. 1G). To identify which tissues alone or together might be the primary source of the insulin resistance observed in Alms1$^{foz/foz}$ mice, the tissue distribution of insulin-mediated deoxyglucose (DOG) uptake was compared in WT and Alms1$^{foz/foz}$ mice. This confirmed that severely impaired DOG uptake was limited to the WAT of Alms1$^{foz/foz}$ mice with a compensatory increase in DOG uptake into the insulin-responsive gastrocnemius and soleus muscles when compared to WT mice.

These studies demonstrate that although Alms1$^{foz/foz}$ mice become obese and develop progressive T2DM with age, the major initial defect contributing to insulin resistance and hyperglycaemia is a failure in the absence if functional ALMS1 of adipose tissue glucose uptake in response to insulin signaling, with this defect predating the development of obesity.

Example 2

Silencing of Alms1 in Human Adipocytes Blocks Glucose Uptake Through Impaired GLUT4 Cellular Sorting Materials.

From Molecular Probes, Invitrogen: Acridine Orange, Image-iT® LIVE Plasma Membrane and Nuclear Staining Labeling Kit, 2-NBDG (2-(N-7-nitrobenz-2-oxa-1, 3-diazol-4-yl)amino)-2-deoxyglucose), Hoechst 33258 and Cell Light™ Early Endosomes-RFP* BacMam 2.0*; Catalog #: A3568, 134406, N13195, H3569 and C10587. From Lonza: AdipoRed™ Assay Reagent (Catalog #: PT-7009). Lentiviral particles from Santa Cruz Biotechnology, INC.: ALMS1 shRNA (h) Lentiviral Particles, TBC1D4 shRNA (h) Lentiviral Particles and Control shRNA Lentiviral Particles-A; Catalog #: sc-72345-V, sc-61654-V and sc-108080 respectively. From Tocris Biosciences: Nigericin Sodium Salt (Catalog #: 4312).

Biochemical Tests.

Mice were tested for insulin resistance by the insulin tolerance test (ITT) and intraperitoneal glucose tolerance test (IPGTT). For the ITT, mice were fasted 4 hours with no access to food but free access to water. Mice were weighed and insulin (Humulin R, Eli Lilly, USA) was injected ip at 0.75 U/kg body weight in 0.9% saline for injection (Pfizer, USA). Tail blood was obtained and the plasma glucose was determined for each mouse using a glucometer (Optium Xceed, Abbott, USA) and blood glucose test strips (Optium point of care, Abbott, USA) at 0, 15, 30 and 60 min after insulin injection. For the IPGTT, mice were fasted 18 hours and injected at 2 mg/g body weight with D-glucose (Analar, VWR, USA) in 0.9% saline for injection. Plasma glucose was determined for each mouse using a glucometer with sampling via tail vein at 0, 15, 30, 60 and 120 min after glucose injection. For plasma insulin measurement, blood was collected on conscious animals via cheek bleeding. After collection, blood samples were kept on ice and spun at 17000 g, 10 min at 4° C. Insulin levels were assayed using a commercial ultrasensitive mouse insulin ELISA kit (Crystal Chem Inc., USA). The homeostasis model assessment of insulin resistance (HOMA-IR) index was calculated using individual mouse fasting insulin and fasting glucose levels.

The following formula was used: HOMA−IR=[fasting glucose (mg/dL)×fasting insulin (μU/mL)]/405.

Cell Culture.

Human white visceral preadipocytes (Catalog #: C-12732; PromoCell) and human mesenchymal stem cells (Catalog #: C-12974; PromoCell) derived from healthy bone marrow were purchased. The preadipocytes were seeded according to manufacturer's protocol and cultured in the Preadipocyte growth medium (Catalog #: C-27410; Promo-Cell) to confluence. One day before inducing terminal adipogenesis, the cells were infected with specific lentiviral particles consisted of a pool of 3 shRNAs target-specific constructs purchased from Santa Cruz Biotechnology and on the next day, adipogenic differentiation was induced by changing the medium to the Preadipocyte Differentiation Medium (Catalog #: C-27436; PromoCell) for 2 days. After the differentiation phase, the medium was finally changed to the Adipocyte Nutrition medium (Catalog #: C-27438; PromoCell). For the culture without insulin, Adipocyte Basal Medium (Catalog #: C-2431; PromoCell) without insulin was complemented with 5 g/L of deoxyglucose, 8 μg/mL d-Biotin, 400 ng/mL Dexamethasone. For the hMSCs, they were cultured in Mesenchymal Stem Cell Growth Medium (Catalog #: C-28010; PromoCell) to confluence. hMSCs were transfected with specific siRNAs as described above and on the next day adipogenic differentiation was induced by changing the medium to the MSC Adipogenic Differentiation Medium (Catalog #: C28011; Promocell).

RNA Extraction, cDNA Synthesis, q-PCR and Taqman.

Total RNA was prepared from the different tissues and cells using a RiboPure™ kit (Catalog #: AM1924; Ambion) followed by a DNAse treatment with the TURBO DNA-Free™ (Catalog #: AM1907; Ambion). RNA integrity was assessed by gel electrophoresis and RNA concentration by Eppendorf Biophotometer Plus with the Hellma® Tray Cell (Catalog #: 105.810-uvs; Hellma). Reverse transcription of 1 μg total RNA to cDNA was performed using the BioRad iScript™ cDNA synthesis kit (Catalog #: 170-8891; Bio-Rad). Real-time quantitative polymerase chain reaction amplification was performed in a BioRad CFX96™ Real-Time System using the iQ™ SYBR® Green Supermix (Catalog #: 170-8886; BioRAd) and primer sets optimized for tested targets for SYBR Green-based real-time PCR for the real-time PCR. Taqman analysis was carried out with the specific gene assay with the Taqman® Fast Advanced Master Mix (Catalog #: 4444557; Applied Biosystems). The normalized fold expression of the target gene was calculated using the comparative cycle threshold (CO method by normalizing target mRNA $C_t$ to those for GAPDH using the CFX Manager Software Version 1.5 and was verified using the Lin-Reg program.

Western Blots and Immunofluorescence Microscopy.

Male Alms1$^{foz/foz}$ and WT littermates were anaesthetized. The following insulin sensitive tissues: liver, heart, muscle and adipose tissue were harvested and directly placed in RIPA buffer (Tris 50 mM, NaCl 150 mM, 0.1% SDS, 1% Triton-X100) supplemented with Complete mini protease inhibitor cocktail and PhosSTOP phosphatase inhibitor cocktail (Roche, Switzerland). Samples were sonicated and centrifuged 30 min at 17 000 g, 4° C. 30 min. Protein concentration assayed with BCA assay (Thermo Fisher Scientific, USA). Cellular proteins from cells were obtained by trichloroacetic acid precipitation and immunoblot analyses were performed using 30-50 μg total protein. Specific antibody binding was visualized using the SuperSignal® West Femto Maximum Sensitivity Substrate (catalog #: Lf145954, Pierce) on a BioRad Versadoc™ Imaging System or ImageQuant LAS 4000 imager (GE Healthcare, UK). Nonspecific proteins stained with Ponceau S were used as loading controls to normalize the signal obtained after specific immunodetection of the protein of interest using the Bio-Rad Quantity One program. For immunofluorescence experiments, the cells were seeded on permanox 8-wells Lab-Tek II Chamber Slide (Catalog #: 177445; NUNC). Cells were treated as indicated. Then both cells and tissues cryosections were processed for protein detection after methanol fixation and permeabilized with 0.1% Triton X-100. The microscopy slides were mounted for detection with Vectashield Mounting Medium (Catalog #: H-1200; Vector Laboratories). To view membrane-associated proteins, cells were formalin fixated for 15 min and were directly blocked, followed by immunostaining and acquisition using an upright Zeiss Axiolmager Z2 microscope. Image analysis, 3D reconstitution and Time Lapse experiments and endosomes tracking experiments were performed using either the Zeiss AxioVision program with the corresponding 3D and Tracking Zeiss modules or the Zeiss Zen 2012 imaging platform.

Fluorescence Measurement.

The preadipocytes were cultured in a 96 well plate and 12 wells infected with the either ALMS1 shRNA lentivral particles or CTRL shRNA lentivral particles and differentiated the next day into mature adipocytes. 3 weeks later, the intracellular trigylcerides were stained with AdipoRed staining following the manufacturer's procedure and the fluorescence was measured on a Tecan Infinite 200 quad4 monochromator (Tecan, Lyon, France) at a wavelength of 520 nm. The generated data were then analyzed using the Tecan Magellan Data Analysis software using as blank unstained adipocytes.

Co-Immunoprecipitation Experiments.

For the co-immunoprecipitation experiments, we used the Dynabeads® Antibody Coupling kit (Catalog #: 143.11D, Invitrogen) in combination with the Dynabeads® co-immunprecipitation kit (Catalog #: 143.21D, Invitrogen). The hMSCs were cultured to confluence and adipogenic differentiation was triggered by medium change. 7 days after adipogenic differentiation was initiated by medium change, the adipocytes, cultured with our without Ins. 24 hours prior to lysis, were lysed under native conditions and used according the kit. After immunoprecipitation and release from the beads, the samples were loaded on a NuPage 3-8% TrisAcetate Gel (Catalog #: EA0375BOX, Invitrogen) with a Hi Mark™ Prestained HMW Protein Standard (Catalog #: LC5699, Invitrogen).

Protein Preparation and Identification by Mass Spectrometry.

In gel digestion: The gel digestion procedure was carried out as described by Rabilloud et al. (ref). Preparation of the gel pieces before trypsin digestion was performed by a liquid handler robot (QuadZ215, Gilson International, France). Briefly, gel bands were washed alternately with 100 μl of 25 mM $NH_4HCO_3$ and then 100 μl of 50% acetonitrile (ACN) (3 min wash under shaking and the liquid was discarded before addition of the next solvent). This hydrating/dehydrating cycle was repeated twice and the pieces of gel were dried for 20 min before reduction (10 mM DTT/25 mM $NH_4HCO_3$ buffer at 56° C. for 45 min) and alkylation (25 mM iodoacetamide/25 mM $NH_4HCO_3$ buffer for 45 min, room temperature). Afterwards, gel spots were again washed with 3 cycles of 25 mM $NH_4HCO_3$/ACN alternately. Following 20 min drying step, the gel pieces were rehydrated by three volumes of trypsin (Promega, V5111), 12.5 ng/μl/in 25 mM $NH_4HCO_3$ buffer (freshly diluted) and incubated overnight at room temperature. Tryptic peptides were extracted from gel by vigorous shaking for 30 min in adapted volume of 35% H2O/60% ACN/5% HCOOH and a 15 min sonication step.

MALDI-TOF (/TOF) Mass Spectrometry and Database Search.

MALDI mass measurement was carried out on an Autoflex III Smartbeam (Bruker-Daltonik GmbH, Bremen, Germany) matrix-assisted laser desorption/ionization time-of-flight mass spectrometer (MALDI-TOF TOF) used in reflector positive mode. A prespotted anchorchip target (PAC system from Bruker Daltonik, technical note TN011) with HCCA matrix was used to analyse tryptic digests. The resulting peptide mass fingerprinting data (PMF) and peptide fragment fingerprinting data (PFF) were combined by Biotools 3.2 software (Bruker Daltonik) and transferred to an intranet version of the search engine MASCOT (Matrix Science, London, UK). Variable modifications (N-term protein acetylation, methionine oxidation and cysteine carbamidomethylation) and one tryptic missed cleavage were taken into account and the peptide mass error was limited to 50 ppm. Proteins were identified by searching data against a NCBI non-redundant protein sequence database and then submit to the human restricted database. In all results, the probability scores were greater than the score fixed as significant with a p-value of 0.05. NanoLC-MSMS mass spectrometry and database search: For nanoLC-MS/MS analysis, peptides were transferred in glass inserts, compatible with the LC autosampler system (nanoLC-U3000, Dionex, US). The LC system was coupled to an ESI-Q-TOF mass spectrometer (MicroTOFQ-II, Bruker, Germany). The method consisted in a 60 min run at a flow rate of 300 nL/min using a gradient from two solvents: A (99.9% water: 0.1% formic acid) and B (99.92% acetonitrile: 0.08% formic acid). The system includes: a 300 μm×5 mm PepMap C18 used for peptides preconcentration and a 75 μm×150 mm C18 column used for peptides elution. The TOF analyzer was calibrated each day: data were acquired and processed automayically using Hystar 2.8 and DataAnalysis 2.6 softwares. Consecutive searches against the NCBInr database first and then against the human sub-database were performed for each sample using local versions of Mascot 2.2 (MatrixScience, UK) and Proteinscape 2.0 (Bruker, Germany). False-positive rate (FPR) for protein identification was estimated using a reverse decoy database: protein validation was done using a FPR below 1%. Moreover, proteins identified by only 1 peptide were checked manually: MS/MS spectra were inspected according to conventional fragmentation rules.

In Situ Proximity Ligation Assay (PLA).

Duolink in situ PLA kit with antimouse PLUS probe and anti-rabbit MINUS probe (catalog #: 90701 and 90602; OLINK Bioscience) were used in combination with the appropriate primary antibodies according to the manufacturer's procedure. Human primary preadipocytes and mature adipocytes were cultured on 8-well Lab-Tek II chamber slide (Nunc) and treated as for immunofluorescence microscopy until the primary antibody incubation step. After washing, cells were decorated with PLA PLUS and MINUS probes (1:20 dilution) for 2 hrs at 37° C. Hybridization and ligation of probes, amplification, and final SSC washing were performed according to the manufacturer's procedure. Fluorescence transfer based on protein-protein interaction was visualized using the Duolink Detection kit 613 (OLINK Bioscience) and images were acquired.

Statistics.

Statistical analyses were performed using GraphPad Prism 5 software (GraphPad Software, Inc., USA). Results are shown as means±standard deviation. Significance of the results was determined by paired t tests or the non-parametric Mann-Whitney U test was used for statistical comparison of BMI and AUC data. A value of $P<0.05$ was considered to denote statistical significance and was marked with an asterisk.

Using primary human preadipocytes as an in vitro model, the inventors localized ALMS1 primarily in a cytoplasmic rather than the previously reported centrosomal pool. ALMS1 was silenced during adipogenesis and although a significant decrease in the anti-adipogenic factor Pref-1 was observed, no major differences could be detected in expression levels of pro-adipogenic transcription factors such as the cEBPs and PPARγ.

Figure 2:
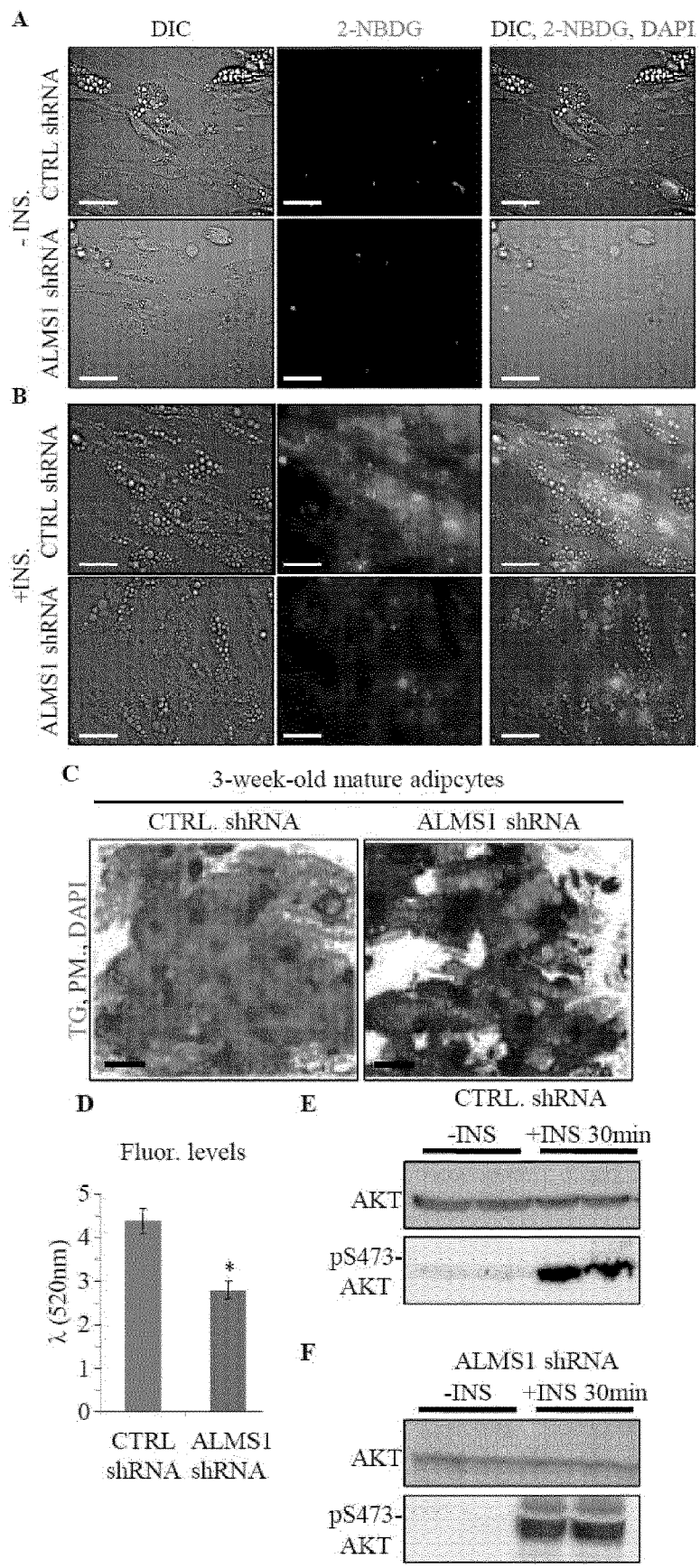
FIG. 2. ALMS1 silencing effect in human mature adipocytes (A) Photographs showing the lack of absorption of 2-NBDG (green) in control (shCTRL shRNA) or ALMS1-deprived adipocytes (ALMS1 shRNA) silenced mature adipocytes in absence of INS. (B) Photographs depicting lack of absorption of 2-NBDG in ALMS1 shRNA compared to CTRLshRNA. Nuclei were counterstained with DAPI, DIC: Differential Interference Contrast pictures. (C) 3D images of CTRLshRNA or ALMS mature adipocytes stained for intracellular Triglycerides (TG), plasma membrane in red (PM) and nuclei in blue (DAPI). (D) Measurements of fluorescent levels correlating with amounts of intracellular TG in mature adipocytes (n=16 wells per condition measured) * p-value=0.05. (E-F) Immunodetection of AKT and pS473-AKT in CTRLshRNA and ALMS1 shRNA treated mature adipocytes in presence and absence of INS. (G) 3D images of CTRLshRNA and ALMS1shRNA mature adipocytes showing cellular localization of Insulin receptor (IR in red) and GLUT4 (in green) in absence of Ins. Cut-view images displaying the dynamics of GLUT4 localization in absence of Ins. (H), after 30 min. INS. stimulation (I) and with 30 min INS. stimulation followed by 2 hours of absence of INS. (J) in CTRLshRNA and ALMS1shRNA mature adipocytes. Scale bars: 25 µm in A, B, C and 5 µm in G-J.

Following ALMS1 silencing in 2-week-old mature adipocytes, glucose absorption capacity was assessed using labelled glucose analogue (2-NBDG). In the absence of insulin stimulation, no 2-NBDG uptake could be detected in ALMS1-silenced and control mature adipocytes (FIG. 2A). On the other hand, insulin stimulation resulted in increased 2-NBDG uptake in the control human mature adipocytes (FIG. 2B, top panel) but not ALMS1-silenced cells (FIG. 2B, bottom panel). Further to reduced glucose absorption in ALMS1-silenced adipocytes, the inventors observed a reduction in intracellular triglycerides (TG) in these cells a week later (FIG. 2C-D). Of note, this reduced glucose absorption in ALMS1-deficient adipocytes was not associated with decreased phosphorylation of AKT, the downstream signaling target of insulin, as pS473-AKT levels after 30 minutes incubation with insulin were similar in both control and ALMS1-silenced human adipocyes (FIG. 2E-F), consistent with the normal to increased levels of AKT phosphorylation previously observed in Alms1$^{foz/foz}$ murine adipocytes (FIG. 1G).

The inventors next investigated the dynamics of GLUT4 in human adipocytes in the absence of ALMS1. Insulin receptor (IR) cellular localization to the plasma membrane was not impaired following ALMS1 silencing being detected in the vicinity of the plasma membrane (PM) in the absence of insulin. (FIG. 2G, top panel). By contrast, in ALMS1-deficient adipocytes in the absence of insulin GLUT4 lost its perinuclear localization and was detected dispersed throughout the cell cytoplasm rather than assuming its usual perinuclear localisation. (FIG. 2G, middle and bottom panels and 2H). Upon insulin stimulation, GLUT4 was observed to move to the PM within the actin mesh (FIG. 2I) in both control and ALMS1-silenced adipocytes. Two hours post insulin stimulation in the absence of insulin, GLUT4 was still detected dispersed throughout the cytoplasm of the ALMS1-silenced adipocytes whereas control adipocytes had their GLUT4 appropriately re-localized to the perinuclear region (FIG. 2J). As there is an equilibrium between exocytosis and endocytosis of GLUT4 vesicles to and from the PM, the inventors checked to exclude that the impaired GLUT4 sorting in Alms1-silenced adipocytes was not due to defective GLUT4 endocytosis. Examination of dynamin, a key molecule in endocytosis, demonstrated no difference in protein levels nor cellular localization following ALMS1 silencing in adipocytes. Furthermore, the mean velocities of labelled endosomes were similar between ALMS1-silenced and control adipocytes, arguing against a defect in endocytosis being the cause of reduced GLUT4 presence in the PM in response to insulin signaling.

Example 3

ALMS1 is Required for TBC1D4 Targeting to the PM in Response to Insulin Signaling To understand the molecular mechanism underlying the effect of ALMS1 inactivation on GLUT4 localisation, the inventors identified interacting partners of ALMS1 in human adipocytes. Immunoprecipitation (IP) using ALMS1 as the bait was performed using young mature human adipocytes (4 days after differentiation trigger) followed by identification of ALMS1 interacting partners by mass spectrometry. Amongst proteins were immunoprecipitated with ALMS1, was TBC1D4, a known AKT substrate GTPase required for proper retention of GLUT4 in the GLUT4 sorting vesicles (GSVs) and for the translocation of GLUT4 to the cell membrane for intracellular glucose uptake.

Example 4

Development of Structural Homology Models of ALMS1, TBC1D4 and αPKC

Figure 3:
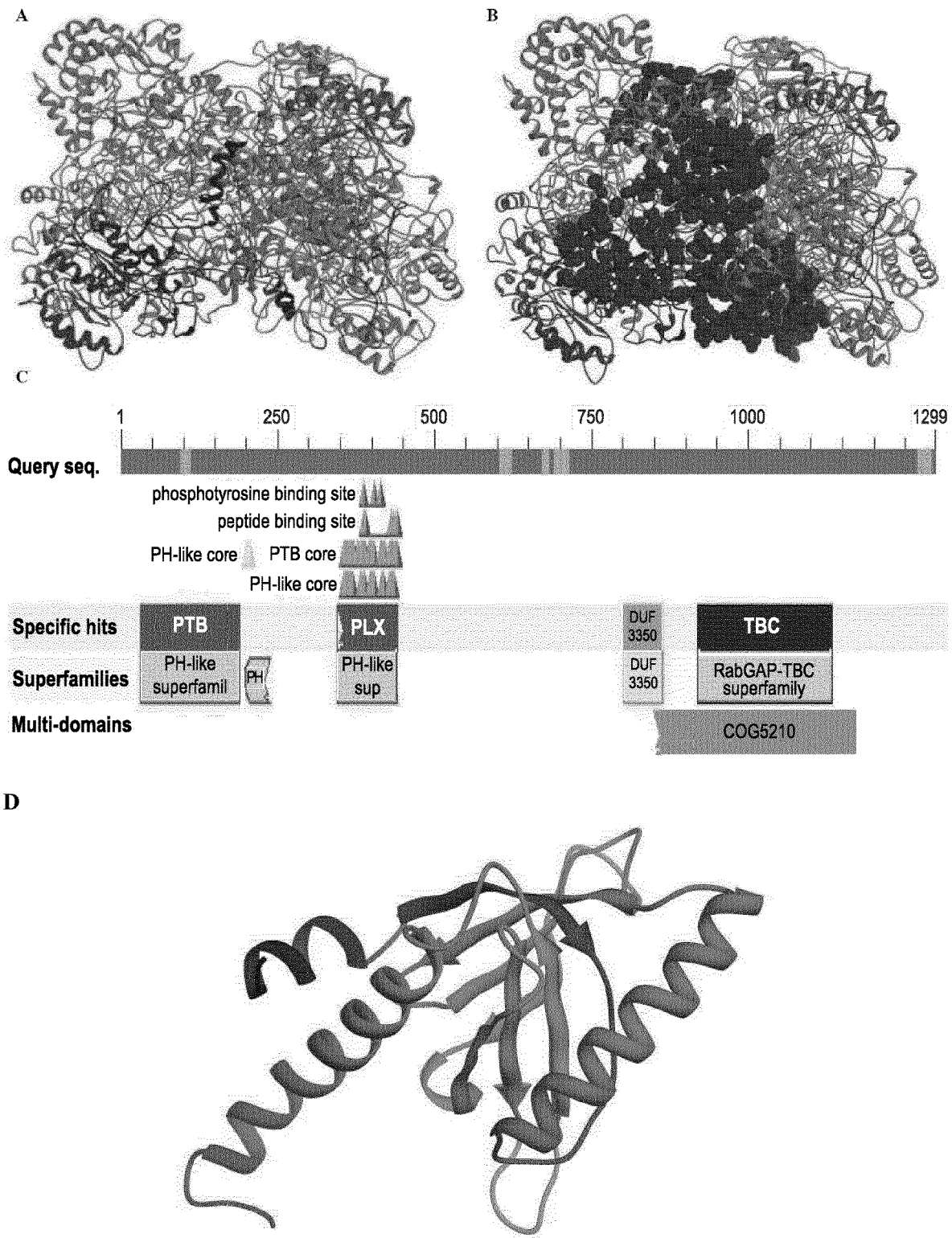
FIG. 3. Predicted interaction sites on ALMS1 protein and modelling of its partner TBC1D4. (A) Predicted 3D structure of the ALMS1 protein with helices and loops. (B) Predicted 3D structure of the ALMS1 protein with the potential interacting sites represented by red dots. (C) Primary sequence of TBC1D4 protein with indicated localization of binding sites or interacting domains. (D) Predicted 3D structure of the TBC1D4 protein.

As the crystal structure of Alms1 has not yet been solved, in silico structural homology modeling was used to predict the 3D structure of ALMS1 and identify structural motifs that could bind potential interacting ligands (FIG. 3A-C).

Structural Model of ALMS1.

The model of ALMS1 was constructed using fragment modeling method with the homology modelling program, Modeller. The amino acid sequence for each exon of ALMS1 was submitted to profile-based threading algorithm available at PISRED server and suitable templates were identified. Then those identified template proteins were aligned with the respective exon sequences and each exon was modeled separately using Modeller. The energy optimization and selection of models were conducted based on discrete optimized protein energy score. Finally, models were assembled to construct the structure of full length ALMS1 and the full-length protein was relaxed and minimized using the molecular dynamics simulation program NAMD.

Structural Model of the PTP Binding Domain of TBC1D4.

The PTP binding domain of TBC1D4 is located within the first 160 residues. No reliable homologues structure was identified to model the structure in between the PTP binding domain and the Rab binding domain. Crystal structure of the PTP domain of murine Disabled-1(Dab-1), 1NU2 (E-value=5.2e-17), which was identified by HMM based template search at Swiss model was used as the template for constructing the PTP binding domain of TBC1D4.

The PTP Domain of TBC1D4 Interacting with ALMS-1.

The macromolecular docking was performed by using the ClusPro 2.0 algorithm. Residues located in the interaction surface with >=0.4 angstrom overlap were considered as interacting residues. Interproscan revealed that the ALMS-1 contained a WD40-like domain within the first 3871 residues. WD40 domain containing proteins are a family of proteins functioning as scaffolds for macro-molecular interactions.

The PTP Binding Domain of TBC1D4 Interacting with ALMS1.

Initially, the PTP binding domain and the RabGTP binding domain of TBC1D4 were docked to the ALMS1 model using the Cluspro 2 server to determine the most probable site of interaction. Then both domains were docked to their respective interacting sites on ALMS1 using Autodock 4.2 and their binding affinities were calculated. Based on the affinities, the PTP binding domain of TBC1D4 binds ALMS1 with ~100 fold higher affinity compared to the RabGTP binding domain. Hence, the inventors predict that the PTP binding domain may have a higher probability to interact with the ALMS1 molecule compared to the RabGTP binding domain.

Modelling the PTP Domain of TBC1D4.

The phospho-tyrosine binding domain of TBC1D4 was modeled after identifying a suitable template from the Swiss model template identification algorithm.

Docking TBC1D4 PTP Domain and RabGTP Binding Domain to ALMS1.

Initially, the PTP binding domain and the RabGTP binding domain of TBC1D4 were docked to ALMS1 using the Cluspro 2 server and the site of interaction was identified. Then both domains were docked to their respective interacting sites using Autodock 4.2 and their binding affinities were calculated.

| | |
|---|---|
| Predicted ALSM-1 residue numbers, with the potential to interact with another ligand | 65, 66, 69, 72, 73, 74, 75, 76, 77, 78, 80, 87, 2875, 2876, 2877, 2878, 2879, 2880, 2881, 2882, 2883, 2884, 2885, 2887, 2888, 2889, 2890, 2892, 2893, 2894, 2895, 2897, 2909, 2910, 2912, 2929, 2931, 2932, 2933, 2934, 2935, 3557, 3558, 4131, 144, 145, 146, 147, 148, 149, 150, 151, 193, 194, 195, 198, 199, 200, 201, 205, 208, 211, 214, 226, 227, 229, 233, 234, 235, 236, 239, 242, 243, 246, 248, 249, 250, 251, 252, 314, 319, 321, 986, 1341, 1344, 2269, 113, 114, 115, 116, 123, 126, 127, 128, 1340, 1438, 1439, 1440, 1441, 1442, 1443, 1444, 1446, 1447, 1448, 1449, 1450, 1451, 1452, 1453, 1454, 1457, 1458, 1459, 1478, 1915, 1918, 1919, 1920, 1922, 1923, 1930, 2041, 2042, 2043, 2257, 2267, 2483, 2484, 3866, 218, 219, 220, 221, 222, 223, 224, 277, 278, 279, 282, 285, 286, 287, 288, 686, 688, 689, 690, 691, 699, 1856, 1858, 1859, 1861, 1862, 1863, 1864, 1865, 1866, 1867, 1868, 1869, 1870, 1871, 1872, 1949, 1968, 1969, 1971, 1974, 1979, 1980, 1981, 1982, 1983, 1984, 2104, 2107, 2111, 2870, 2872, 2874, 2915, 3285, 3286, 3287, 793, 795, 796, 797, 1285, 1314, 1408, 1409, 1422, 1423, 1425, 1426, 1427, 1430, 1431, 1671, 1672, 1794, 1797, 2538, 2539, 2540, 2555, 2556, 2557, 2563, 2564, 2565, 2567, 2568, 2588, 2591, 2599, 2603, 2699, 2701, 2702, 3108 |
| Predicted residues from ALMS1 mediating the interaction with aPKC | E17, D58, S59, G62, H65, L66, Q736, T737, E738, D828, S829, T1088, D1089, A1169, Q1170, F2882, L2883, E2884 |

| | |
|---|---|
| Predicted residues from aPKC mediating the interaction with ALMS1 | F114, D116, C118, L121, N138, Q142, I145, P148, G433, E545, S562, S566, F597, D601, W602, K604, E606, G620, T631, V664, I667 |
| Predicted residues from TBC1D4 mediating the interaction with ALMS1 | G75, A76, P77, A78, R80, E81, V82, I83 |
| Predicted residues from ALMS1 mediating the interaction with TBC1D4 | H65, L66, S2879 |

The homology model revealed that Alms1 assumes an apple core type structure with a large number of bindings sites of potential ligands centered around the core. The TBC1D4 crystal structure was similarly not solved and hence the inventors used a homology modeling approach to predict the structure of the PTP binding domain of TBC1D4 (FIG. 3C-D). Subsequently, in silico docking studies were performed which predicted high affinity binding of TBC1D4 with ALMS1 through hydrogen bonding of TBC1D4 residues G75, A76, P77, A78, R80, E81, V82, I83 with interacting residues H65, L66, S2879 on Alms1 (FIG. 4A). Co-localization of ALMS1 and TBC1D4 was then confirmed in human adipocytes by immunofluorescence studies (FIG. 4B). The expression levels of GLUT4, TBC1D4, and RAP were next tested in ALMS1-silenced adipocyte with or without insulin stimulation but no significant differences were found (FIG. 4C). Upon phosphorylation by activated AKT, phosphorylated TBC1D4 (p-TBC1D4) in adipocytes targets RAB proteins such as RAB14 and RAB10 prior to GSVs being targeted to the PM. However, upon insulin stimulation of Alms1-silenced adipocytes, no difference could be detected in the levels of TBC1D4, p-TBC1D4, RAB14 and RAB10 (FIG. 4D). The inventors next focused on GLUT4 cellular localization. In the absence of insulin stimulation, TBC1D4 silencing reproduced the ALMS1 silencing effect seen in mature adipocytes, i.e. a mislocalization of GLUT4 throughout the cytoplasm (FIG. 4E). In response to insulin stimulation, GLUT4 was released from the perinuclear region in control adipocytes spreading-out throughout the adipocyte cytoplasm (FIG. 4F) thereby reproducing the GLUT4 distribution pattern seen in in ALMS1 and TBC1D4-silenced adipocytes in the absence (FIG. 4E) and presence (FIG. 4F), of insulin. The inventors subsequently investigated the effect of ALMS1 silencing on the cellular dynamics of TBC1D4 in response to insulin. In the absence of insulin, TBC1D4 was localized to the perinuclear region in both control and ALMS1-silenced adipocytes (FIG. 4G) but notably, in response to insulin, TBC1D4 was only transported to the PM in control but not ALMS1-silenced adipocytes (FIG. 4H).

Example 5

ALMS1 Forms a Dynamic Protein Complex, the ALMSome, Required for Insulin-Stimulated Glucose Transport in Human Mature Adipocytes Although the inventors showed that ALMS1 silencing prevented TBC1D4 targeting to the PM, it remained to be seen whether this impairment on its own explained the major reduction in glucose uptake observed in ALMS1-deficient adipocytes. The inventors therefore compared the cellular uptake of 2-NBDG upon insulin stimulation in ALMS1 or TBC1D4-silenced or control adipocytes and found almost no 2-NBDG absorbed in the ALMS1-silenced adipocytes compared to control adipocytes (FIG. 5A-B), whereas whilst reduced compared to controls a substantial amount of 2-NBDG was still absorbed by TBC1D4-silenced adipocytes (FIG. 5C). Subsequent GLUT4-antibody binding assays on either ALMS1 or TBC1D4-silenced or control adipocytes following 30 minutes insulin stimulation showed a high proportion of GLUT4 in the PM in control and TBC1D4-silenced adipocytes but not in ALMS1-silenced cells (FIG. 5D-F), indicating that the secondary defect in TBC1D4 targeting to the PM in Alms1-silenced cells did not, in itself, explain the very severe defect in glucose transport and GLUT4 PM expression in ALMS1-deficient cells. A further examination of the Alms1 IP data revealed several subunits of V type ATPase proton (H±) pumps (A, B, D1 and G2) that the inventors then showed to be expressed in mature adipocytes (FIG. 5G) together with αPKC, the activating kinase of the $H^+$ pumps under insulin control. The inventors confirmed that ALMS1 was in close vicinity with the V-ATPase $H^+$ pumps in mature adipocytes in the presence of insulin both by an in situ PLA Duolink approach targeting ALMS1 and the proton pumps subunits A1 and D1 (FIG. 5H) and also by co-immunostaining ALMS1, VATPase A1 and D1 and αPKC (FIG. 5H, I). ALMS1 co-localized with the proton pump subunit V0D1 (FIG. 5I) that is integrated into the GSV membrane indicating that ALMS1 is transported in the adipocyte together with the proton pumps localized within the GSVs. Using their in silico-based structural model of ALMS1 interacting partners the inventors identified a binding motif for PKC on Alms1. The binding sites for TBC1D4 and αPKC on Alms1 were in such close proximity that the model showed that simultaneous docking of both proteins to Alms1 was not possible due to steric hindrance (FIG. 5J). The inventors thus hypothesized. To test their hypothesis that ALMS1 binding of αPKC or alternatively TBC1D4 was under the reciprocal control of insulin signaling in the adipocytes the inventors performed further IPs again using ALMS1 as bait but this time using human mature adipocytes cultured in the presence or absence of insulin with IPs being immunoblotted for both αPKC and TBC1D4. The results revealed that αPKC could only be pulled down by Alms1 and detected by immunoblotting in extracts of adipocytes incubated in the absence of insulin (FIG. 5K) whereas TBC1D4 was only pulled down by ALMS1 and detected in extracts of adipocytes incubated in the presence of insulin, consistent with the inventors model of reciprocal insulin-regulated Alms1 binding (FIG. 5L).

Example 6

The ALMSome is Required for the Acidification of GSVs Prior to GLUT4 Delivery to the Plasma Membrane While AKT-phosphorylation of TBC1D4 has been known to in some way lead to GLUT4 trafficking, the ultimate GSV-PM fusion step is an insulin regulated non-AKT dependent event that requires osmotic swelling of the GSVs under the action of the vATPase H$^+$ pump. However, knowledge of the actual signal and mechanism for activation of the H$^+$ pump by insulin was missing. The inventors tested if ALMS1 inactivation could prevent the acidification of the GSVs and therefore the chemo-osmotic-mediated release of GLUT4 to the PM using the acidotrophic dye, acridine orange, which emits a green fluorescence at low concentration and an orange-red fluorescence at high concentrations in the lysosomes in which acridine orange is protonated and sequestered. In absence of insulin, no orange-red fluorescence was detected in the adipocytes. By contrast, insulin induced a rapid appearance of red color in control human mature adipocytes (FIG. 6A) but not in ALMS1-silenced adipocytes (FIG. 6B) indicating loss of insulin-mediated acidification of lysosomes in ALMS1-silenced adipocytes.

Figure 6:
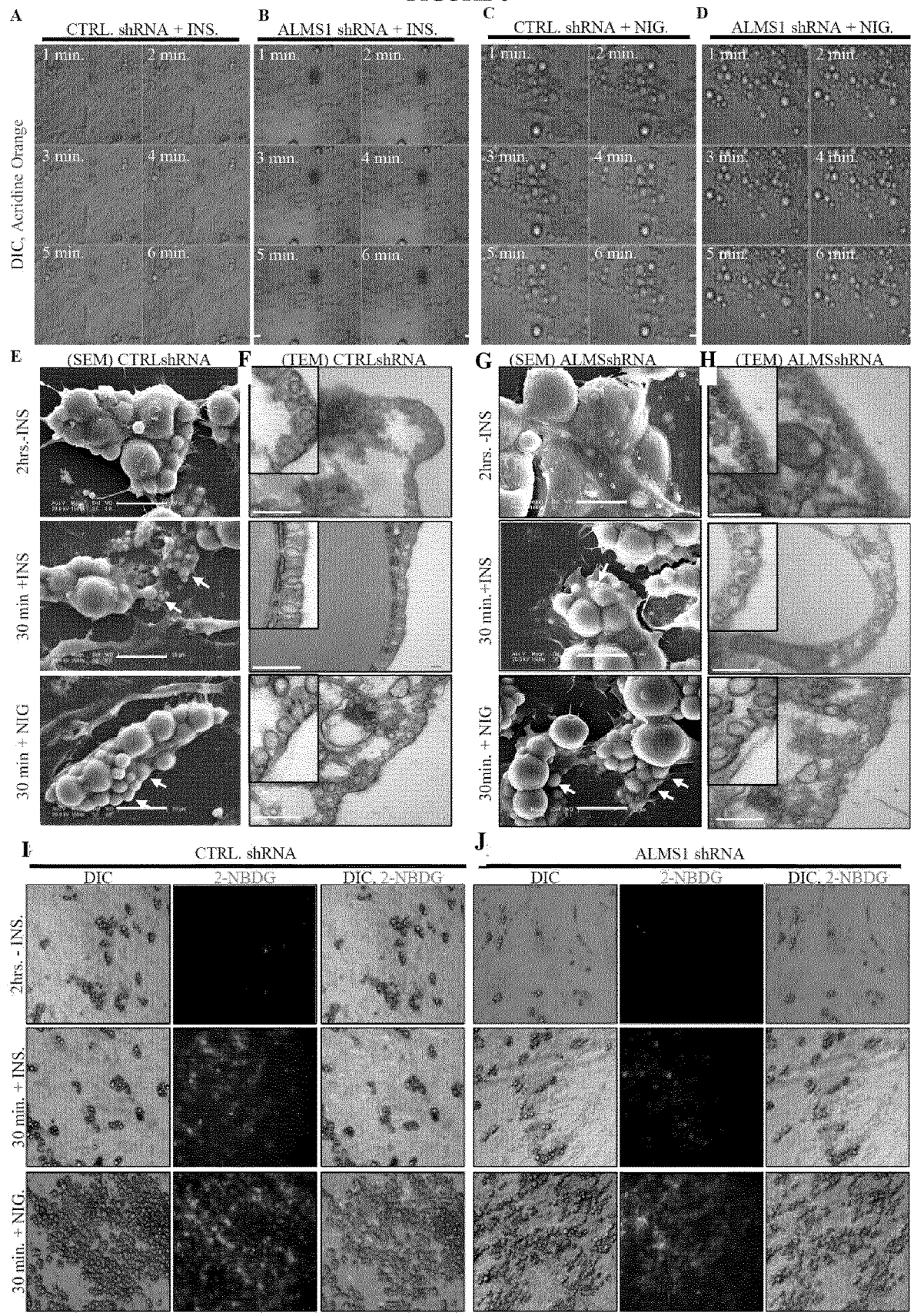
FIG. 6. Restoring acidification in ALMS1-deprived adipocytes reinstate glucose absorption (A-B) Time lapse pictures were performed on either control or ALMS1-deprived Acridine orange stained adipocytes stimulated with INS. (C-D) Time lapse pictures were performed on either control or ALMS1-deprived Acridine orange stained adipocytes stimulated with an electroneutral $K^+/H^+$ exchange ionophore, Nigericin (NIG.). (E) Top to bottom: Scanning electron microscopy (SEM) pictures of control adipocytes stimulated either without Ins. or with INS. or with NIG. White arrows show swelled vesicles. (F) Corresponding Transmitted Electron microscopy (TEM) pictures shown in (E) showing vesicles fusion with the plasma membrane in presence of INS. and NIG. (G) Top to bottom: SEM pictures of ALMS1-deprived adipocytes stimulated either without INS or with INS. or with NIG. (H) Corresponding TEM pictures shown in (G) showing vesicles fusion with the plasma membrane only in presence of NIG. (I) Photographs showing the intracellular content of 2-NBDG (green) in control mature adipocytes either in absence of INS. (top panel) or after 30 minutes INS. stimulation (middle panel) or after 30 min. NIG. Stimulation (bottom panel). (J) Photographs showing the intracellular content of 2-NBDG (green) in ALMS1-deprived mature adipocytes either in absence of INS. (top panel) or after 30 minutes INS. stimulation (middle panel) or after 30 min. NIG. stimulation (bottom panel). Scale bars: 20 µm except for F and H: 500 nm.

The inventors next tested whether acidifying ALMS1-silenced adipocytes using Nigericin (NIG.), an electroneutral K$^+$/H$^+$ exchange ionophore known to cause osmotic swelling of the GSVs would bypass the Alms1-associated defect in GLUT4 fusion and glucose absorption. NIG. treatment resulted in a rapid acidification of both control and ALMS1-silenced adipocytes (FIG. 6C-D), thereby activating the swelling and fusion of the intracellular vesicles. In parallel, electron microscopy analysis showed vesicles sitting next to the PM without fusion in absence of insulin in both control and ALMS1-silenced adipocytes (FIG. 6E-F, top panels). Insulin treatment caused a swelling of the vesicles (FIG. 6E, middle panels) associated with fusion of vesicles with the PM for glucose absorption only in the control adipocytes (FIG. 6E, middle panels) but not in ALMS1-silenced adipocytes (FIG. 6F, middle panels). However, NIG. induced vesicular swelling and fusion with the PM in both control and ALMS1-silenced adipocytes (FIG. 6E-F, bottom panels). The NIG treatment restored glucose absorption in ALMS1-silenced adipocytes. While insulin had little effect in inducing 2-NBDG absorption in ALMS1-silenced adipocytes (FIG. 6G-H, top and middle panels), NIG not only restored vesicle fusion but could also be shown to restore 2-NBDG absorption in the ALMS1-silenced adipocytes to levels seen in control cells (FIG. 6G-H, bottom panels) This restored glucose transport in NIG-treated ALMS1-silenced adipocytes correlated with restored GLUT4 fusion with the PM (FIG. 7A) but not with TBC1D4 targeting to the PM (FIG. 7B); and led to restoration of TG-filling of ALMS1-silenced adipocytes 24-hours post NIG treatment.

Example 7

Identification of Peptide Inhibitors of PKC Binding to Alms1

Once the site of binding interaction between two proteins is known, as known in the art it is possible using knowledge of the conformation and amino acids of each protein involved in mediating the interaction, to use computational models to design peptides or small molecule drugs which by binding in the region of the interaction site are able to sterically or otherwise hinder the binding interaction. The inventors therefore sought to identify peptides that would inhibit the interaction of ALMS1 and αPKC or TBC1D4 using their previously described ALMS1, TBC1D4 and αPKC structural models described in Example 4. Peptides predicted using this method to block the interaction between αPKC and ALMS1 included the sequences LDSDSHYG-PQHLESIDD (SEQ ID No 5), DSHQTEETL (SEQ ID No 6), QQTLPESHLP (SEQ ID No 7), QALLDSHLPE (SEQ ID No 8). PADQMTDTP (SEQ ID No 9), HIPEEAQK-VSAV (SEQ ID No 10) or SCIFLEQ (SEQ ID No 11). A peptide identified using this method to block the interaction between TBC1D4 and ALMS1 was the sequence GCGA-PAAREVILVL (SEQ ID No 12).

Example 8

Figure 8A:
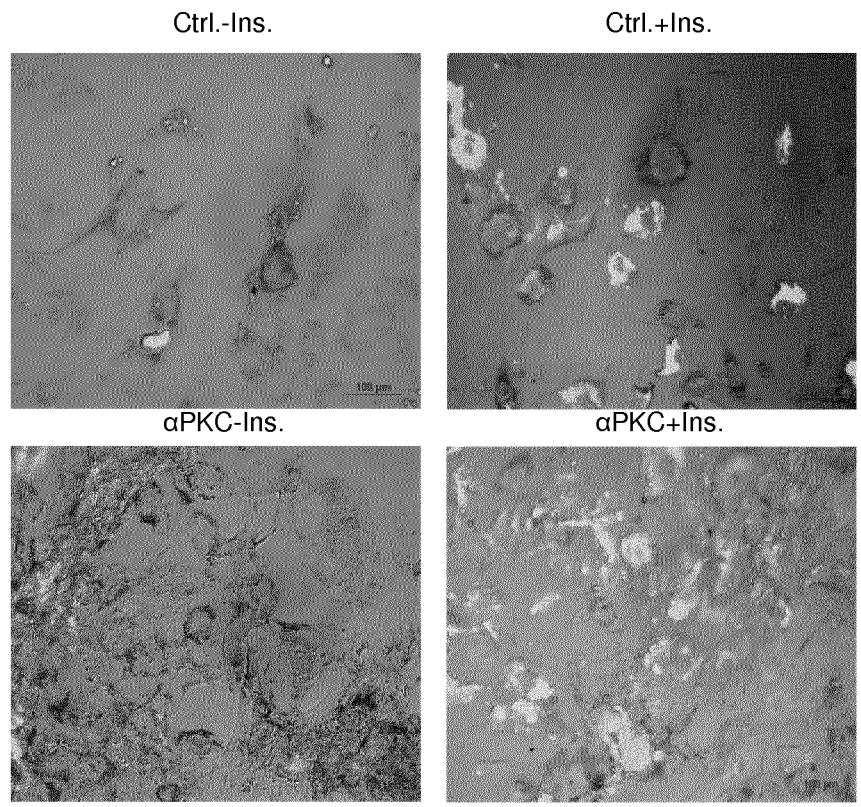
FIG. 8. Glucose absorption is triggered in absence of INS through specific interference of αPKC binding site in the ALMSome (A) Photographs showing absorption of 2-NBDG in presence or absence of INS in adipocytes infected with either CTRL lentiviral particles or αPKC domain carrying lentiviral particles. (B) Quantification of intracellular glucose analogue 2-NB in presence or absence of INS in adipocytes infected with either CTRL lentiviral particles or αPKC domain carrying lentiviral particles. (n=8 per group).
Figure 8B:
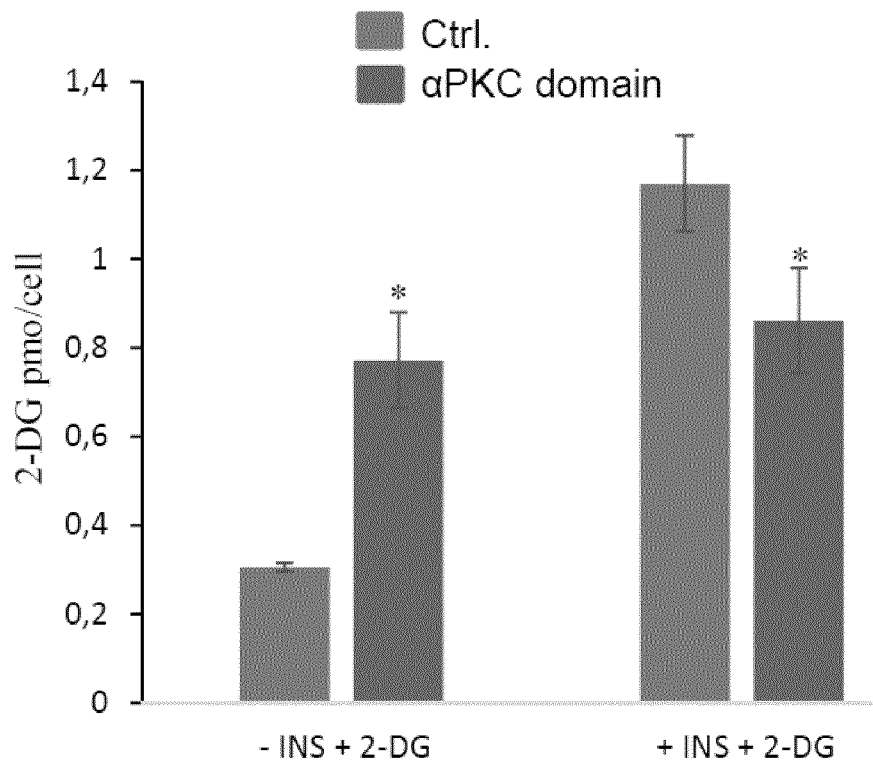
Figure 9:
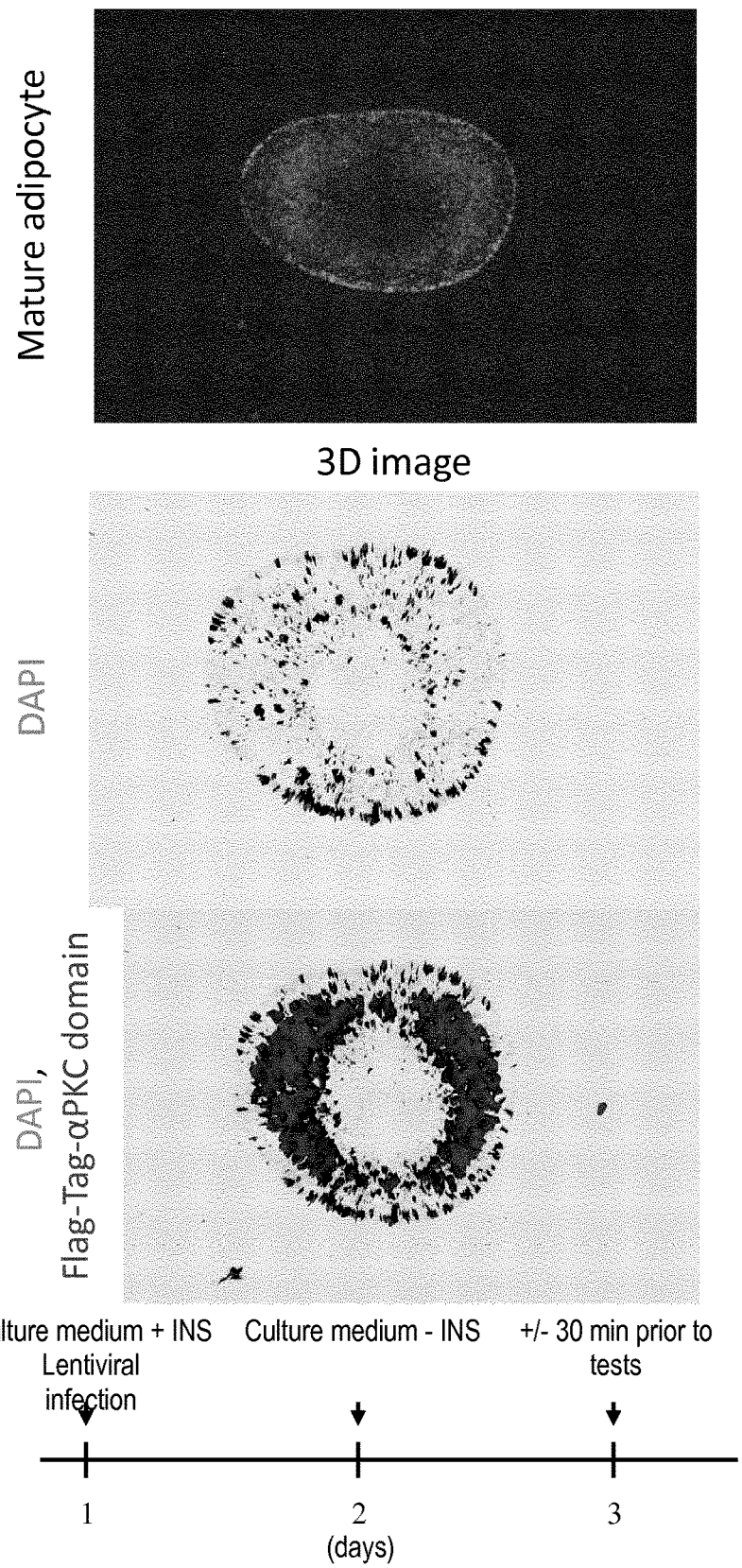
FIG. 9. min-αPKC-FLAG construct characterization in adipocytes

Expression of the Specific ALMS1-Interacting αPKC Interacting Domain in Mature Adipocytes Triggers Glucose Absorption in Absence of Insulin Next, the inventors verified the hypothesis that insulin mediates the release of αPKC from the ALMSome complex in order to induce glucose absorption. For that, they cloned the interacting domain of αPKC (SEQ ID Nos 14 and 15) in a lentiviral vector together with a Flag-TAG. The selected sequence was the minimum sequence of αPKC (min-αPKC-FLAG) so as to prevent sterical hindrance with the TBC1D4 interaction site on ALMS1. The expressed min-αPKC-FLAG in the adipocytes competes with the endogenous αPKC to prevent it from binding Almsome and hence favor the insulin-mediated TBC1D4 binding to Almsome. Mature adipocytes were then infected with either control or min-αPKC lentiviral particles to assess the impact of min-αPKC-FLAG on glucose absorption. 48 hours post-infection, min-αPKC-FLAG was immunodetected using an antibody against the FLAG-Tag (FIG. 9). For the in vitro proof of concept, we treated mature adipocytes as described (FIG. 9) and then incubated the treated mature adipocytes with 2-NBDG to assess the effect of min-αPKC-FLAG on glucose absorption. Of interest, 2-NBDG was absorbed in min-αPKC-FLAG treated adipocytes in absence of INS (FIG. 8A, left column) which corresponded to a 3.5 times increase compare to control (FIG. 8B). On the other hand, no significant difference was observed in presence of INS (FIG. 8A, right column and 8B). These data demonstrate that targeting the interaction of ALMS1 and αPKC is sufficient to trigger glucose absorption in the adipocytes irrespective of the presence of INS.

Production of Lentiviral Vector Carrying the αPKC Domain

The ALMS1-interacting domain of human PKCα was amplified from human HEK293 cell cDNA with N-terminal FLAG tag using Forward 5'-gtacGAATTCGCCACCATG-GATTACAAGGATGACGACGATAAGCTCACGGACT-TCAAT TTCCTC-3' (SEQ ID No 16) and Reverse 5'-tagcG-GATCCTCATACTGCACTCTGTAAGATGGG-3' (SEQ ID No 17) primers and cloned into lentiviral vector pCDH-EF1-MCS-IRES-puro (System Biosciences). For virus production, PKCα lentiviral vectors were transfected into 293TN cells (System Biosciences) along with packaging plasmids psPAX2 and pMD2.G (Addgene) with the weight ratio of 3:2:1 respectively by using Lipofectamine 2000 (Life Technologies). Forty-eight hours after transfection, the culture supernatant was harvested by centrifugation at 500×g for 10 min, followed by filtration through 0.45 µm syringe filter with PES membrane (Sartorius). The virus solution was then concentrated by adding ½ volume of cold 30% (wt/vol) PEG6000 dissolved in 0.5M NaCl and incubated overnight at 4° C. with occasional mixing. The mixture was then centrifuged at 3000×g for 15 min at 4° C. Then the pellet containing lentiviral particles was resuspended in 1 mL DMEM medium and stored at −80° C. before infection of target cells.

The invention claimed is:

1. A method of treating or delaying the progression or onset of diabetes mellitus, insulin resistance, diabetic retinopathy, diabetic neuropathy, diabetic nephropathy, hyperglycemia, obesity, or hyperinsulinaemia in a subject in need thereof, comprising administering a peptide that inhibits the binding of αPKC (Protein Kinase C alpha type) to ALMS1 (Alstrom syndrome protein 1), wherein the peptide consists of SEQ ID NO: 14 or is a stapled peptide consisting of SEQ ID NO: 14.

2. The method according to claim 1, wherein the method treats or delays the progression or onset of type 2 diabetes mellitus in the subject.

3. The method according to claim 1, wherein the peptide consists of SEQ. ID NO: 14 and is stapled.

4. The method of claim 1, wherein the peptide consists of SEQ ID NO: 14.

5. A method of stimulating glucose uptake by adipocytes in a subject in need thereof, comprising administering a peptide that inhibits the binding of αPKC (Protein Kinase C alpha type) to ALMS1 (Alstrom syndrome protein 1), wherein the peptide consists of SEQ ID NO: 14 or is a stapled peptide consisting of SEQ ID NO: 14.

6. The method according to claim 5, wherein the method treats or delays the progression or onset of type 2 diabetes mellitus in the subject.

7. The method according to claim 5, wherein the peptide consists of SEQ ID NO: 14 and is stapled.

8. The method of claim 5, wherein the peptide consists of SEQ ID NO: 14.

* * * * *

UNITED STATES PATENT AND TRADEMARK OFFICE
CERTIFICATE OF CORRECTION

PATENT NO. : 10,821,159 B2  
APPLICATION NO. : 15/114080  
DATED : November 3, 2020  
INVENTOR(S) : Vincent Marion and Nikolai Petrovsky Page 1 of 1

It is certified that error appears in the above-identified patent and that said Letters Patent is hereby corrected as shown below:

In the Specification

Column 8,  
Line 13, "5562, 5566," should read --S562, S566,--.  
Line 24, "52879." should read --S2879.--.

Column 9,  
Line 21, "5562, 5566," should read --S562, S566,--.

Column 10,  
Line 46, "5829," should read --S829,--.  
Line 53, "5562, 5566," should read --S562, S566,--.

Column 15,  
Line 62, "ALMS" should read --ALMS1shRNA--.

Column 16,  
Line 25, "(L66, Y61 and 52879)" should read --(L66, Y61 and S2879)--.

Column 19,  
Line 66, "RAP," should read --IRAP,--.

Column 21,  
Line 48, "(CO method" should read --($C_t$) method--.

Column 27,  
Line 23, "52879" should read --S2879--.  
Line 27, "RAP" should read --IRAP--.

Signed and Sealed this  
Twenty-sixth Day of October, 2021

Drew Hirshfeld  
*Performing the Functions and Duties of the*  
*Under Secretary of Commerce for Intellectual Property and*  
*Director of the United States Patent and Trademark Office*